United States Patent
Hill et al.

(10) Patent No.: US 9,908,927 B2
(45) Date of Patent: Mar. 6, 2018

(54) SINGLE-CHAIN TRAIL-RECEPTOR AGONIST PROTEINS

(71) Applicants: AbbVie Inc., North Chicago, IL (US); Apogenix AG, Heidelberg (DE)

(72) Inventors: Oliver Hill, Neckarsteinach (DE); Christian Gieffers, Dossenheim (DE); Meinolf Thiemann, Schriesheim (DE); Fritz G. Buchanan, Salem, WI (US); Darren C. Phillips, Glenview, IL (US); Susan E. Lappe, Riverwoods, IL (US)

(73) Assignees: AbbVie Inc., North Chicago, IL (US); Apogenix AG, Heidelberg (DE)

( * ) Notice: Subject to any disclaimer, the term of this patent is extended or adjusted under 35 U.S.C. 154(b) by 0 days.

(21) Appl. No.: 14/694,358

(22) Filed: Apr. 23, 2015

(65) Prior Publication Data

US 2015/0337027 A1 Nov. 26, 2015

Related U.S. Application Data

(60) Provisional application No. 61/983,152, filed on Apr. 23, 2014.

(51) Int. Cl.
| | |
|---|---|
| *C07K 19/00* | (2006.01) |
| *C12N 15/62* | (2006.01) |
| *C12N 5/10* | (2006.01) |
| *A61K 38/19* | (2006.01) |
| *C07K 14/705* | (2006.01) |
| *C07K 14/52* | (2006.01) |
| *A61K 38/00* | (2006.01) |

(52) U.S. Cl.
CPC ........ *C07K 14/70575* (2013.01); *A61K 38/00* (2013.01); *C07K 2319/00* (2013.01); *C07K 2319/30* (2013.01)

(58) Field of Classification Search
None
See application file for complete search history.

(56) References Cited

U.S. PATENT DOCUMENTS 7,271,149 B2 † 9/2007 Glaesner
7,317,091 B2 † 1/2008 Lazar
(Continued)

FOREIGN PATENT DOCUMENTS

| WO | 2010010051 A1 | 1/2010 |
|---|---|---|
| WO | WO-2011076781 A1 | 6/2011 |

(Continued)

OTHER PUBLICATIONS

Khamlichi et al., Structure of abnormal heavy chains in human heavy-chain-deposition disease, Eur. J. Biochem. 229:54-60, 1995.*

(Continued)

*Primary Examiner* — Claire Kaufman

(57) ABSTRACT

Provided herein are specific TRAIL receptor agonist proteins, nucleic acids encoding the same, and methods of treating a subject having a TRAIL-associated disease or disorder. The TRAIL receptor agonist proteins provided herein comprise three soluble TRAIL domains and an Fc fragment. The TRAIL receptor agonist proteins are substantially non-aggregating and suitable for therapeutic, diagnostic and/or research applications.

27 Claims, 25 Drawing Sheets

(56) References Cited

U.S. PATENT DOCUMENTS

| | | | |
|---|---|---|---|
| 8,008,443 B2 † | 8/2011 | Dall'Acqua | |
| 8,147,843 B2 | 4/2012 | Hill et al. | |
| 8,450,460 B2 | 5/2013 | Hill et al. | |
| 8,921,519 B2 * | 12/2014 | Hill ..................... | C07K 14/525 |
| 9,212,211 B2 | 12/2015 | Hill et al. | |
| 9,359,420 B2 † | 6/2016 | Hill | |
| 2004/0120955 A1 | 6/2004 | Anderson et al. | |
| 2011/0033521 A1 | 2/2011 | Karin et al. | |
| 2012/0100140 A1 * | 4/2012 | Reyes ................... | C07K 16/00 |
| 2013/0079280 A1 | 3/2013 | Baca et al. | |
| 2015/0126710 A1 | 5/2015 | Hill et al. | |

FOREIGN PATENT DOCUMENTS

| WO | 2013092983 A2 | 6/2013 |
|---|---|---|
| WO | WO-2014013037 A1 | 1/2014 |

OTHER PUBLICATIONS

InvivoGen, Engineered Fc Regions-Review, {Retrieved online Dec. 20, 2016]URL<http://www.invivogen.com/review-engineered-pfuse-chig>, 2011.*

Cummins et al., The TRAIL to viral pathogenesis: The good, the bad and the ugly, Curr. Mol. Med. 9(4):495-505, May 2009.*

Gieffers C., et al., "APG350 Induces Superior Clustering of TRAIL Receptors and Shows Therapeutic Antitumor Efficacy Independent of Cross-Linking via Fc Receptors," Molecular Cancer Therapeutics, 2013, vol. 12 (12), pp. 2735-2747.

Holland P.M., "Death Receptor agonist Therapies for Cancer, which is the Right TRAIL?," Cytokine & Growth Factor Reviews, 2014, vol. 25 (2), pp. 185-193.

International Search Report and Written Opinion for Application No. PCT/US2015/27270, mailed on August 5, 2015, 10 pages.

Lemke J., et al., "Getting TRAIL back on track for cancer therapy," Cell Death & Differentiation, 2014, vol. 21 (9), pp. 1350-1364.

Wang H., et al., "Immunoglobulin Fc Domain Fusion to TRAIL Significantly Prolongs Its Plasma Half-Life and Enhances Its Antitumor Activity," Molecular Cancer Therapeutics, 2014, vol. 13 (3), pp. 643-650.

"International Preliminary Report on Patentability PCT/US2015/027270 Oct. 25, 2016".

Annotated Amino Acid Sequence of Seq ID No. 19, as cited in Third Party Observations dated Jul. 3, 2017 for European Application No. EP15721089 filed Apr. 23, 2015.

Fathimunisa Begum., Immunology, PHI Learning Pvt. Ltd., Jul. 11, 2014, 3 pages.

Fusion Proteins Comprising a Human IgG1 Fc Region, and Alignment Thereof, as cited in Third Party Observations dated Jul. 3, 2017 for European Application No. EP15721089 filed Apr. 23, 2015.

Hamour C.K., et al., "World Antibody-Drug Conjugate Summit, Oct. 15-16, 2013, San Francisco, CA," mAbs, Jan.-Feb. 2014, vol. 6 (1), pp. 18-29.

Klohn P.C., et al., "IBC's 23rd Annual Antibody Engineering, 10th Annual Antibody Therapeutics International Conferences and the 2012 Annual Meeting of the Antibody Society: Dec. 3-6, 2012, San Diego, CA," mAbs, Mar.-Apr. 2013, vol. 5 (2), pp. 178-201.

Supplementary Materials to Gieffers C., et al., "APG350 Induces Superior Clustering of TRAIL Receptors and Shows Therapeutic Antitumor Efficacy Independent of Cross-Linking via Fc Receptors," Molecular Cancer Therapeutics, 2013, vol. 12 (12), pp. 2735-2747, 18 pages.

Third Party Observations mailed Jul. 3, 2017 for European Application No. EP15721089 filed Apr. 23, 2015.

* cited by examiner
† cited by third party

*Fig. 1*
A.
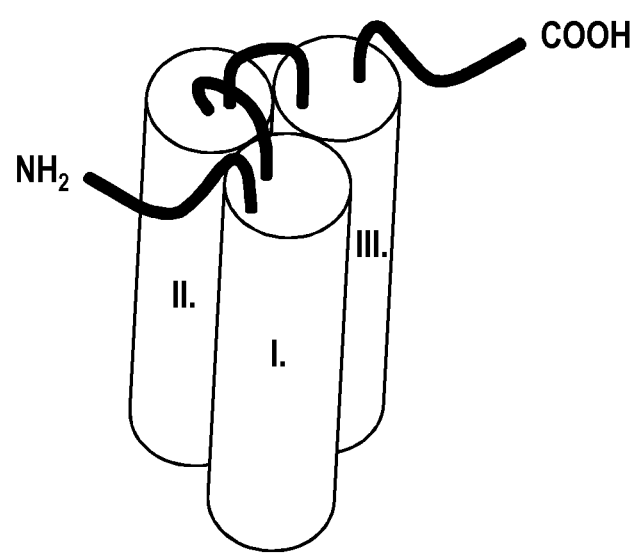
B.

Signal peptide is displayed in bolded and underlined text (not present in the mature protein): SEQ ID NO: 12
TRAIL receptor binding domain monomer modules in plain text: as 120-281 and 121-281 of SEQ ID NO:1, respectively
linkers between the TRAIL monomers in bolded text: SEQ ID NO:2
Fc-domain of human IgG1 in *italicized and underlined text*: *SEQ ID NO: 10*
Hinge-linker between the scTRAIL –RBD and Fc is displayed in *bolded and italicized text*: *SEQ ID NO: 11*

METDTLLVFVLLVWVPAGNGQRVAAHITGTRGRSNTLSSPNSKNEKALGRKINSWESSRSGH
SFLSNLHLRNGELVIHEKGFYYIYSQTYFRFQEEIKENTKNDKQMVQIYKYTSYPDPILLM
KSARNSCWSKDAEYGLYSIYQGGIFELKENDRIFVSVTNEHLIDMDHEASFFGAFLVGGSGS
GNGSRVAAHITGTRGRSNTLSSPNSKNEKALGRKINSWESSRSGHSFLSNLHLRNGELVIHE
KGFYYIYSQTYFRFQEEIKENTKNDKQMVQIYKYTSYPDPILLMKSARNSCWSKDAEYGLY
SIYQGGIFELKENDRIFVSVTNEHLIDMDHEASFFGAFLVGGSGSGNGSRVAAHITGTRGRS
NTLSSPNSKNEKALGRKINSWESSRSGHSFLSNLHLRNGELVIHEKGFYYIYSQTYFRFQEE
IKENTKNDKQMVQIYKYTSYPDPILLMKSARNSCWSKDAEYGLYSIYQGGIFELKENDRIF
VSVTNEHLIDMDHEASFFGAFLVG*GPGSSSSSSGSCDKTHTCPPC**CPAPELLGGPSVFLFPP*
*KPKDTLMISRTPEVTCVVVDVSHEDPEVKFNWYVDGVEVHNAKTKPREEQYSSTYRVVSVLT*
*VLHQDWLNGKEYKCKVSNKALPAPIEKTISKAKGQPREPQVYTLPPSREEMTKNQVSLTCLV*
*KGFYPSDIAVEWESNGQPENNYKTTPPVLDSDGSFFLYSKLTVDKSRWQQGNVFSCSVMHEA*
*LHNHYTQKSLSLSPGK\**

*Fig. 17A*

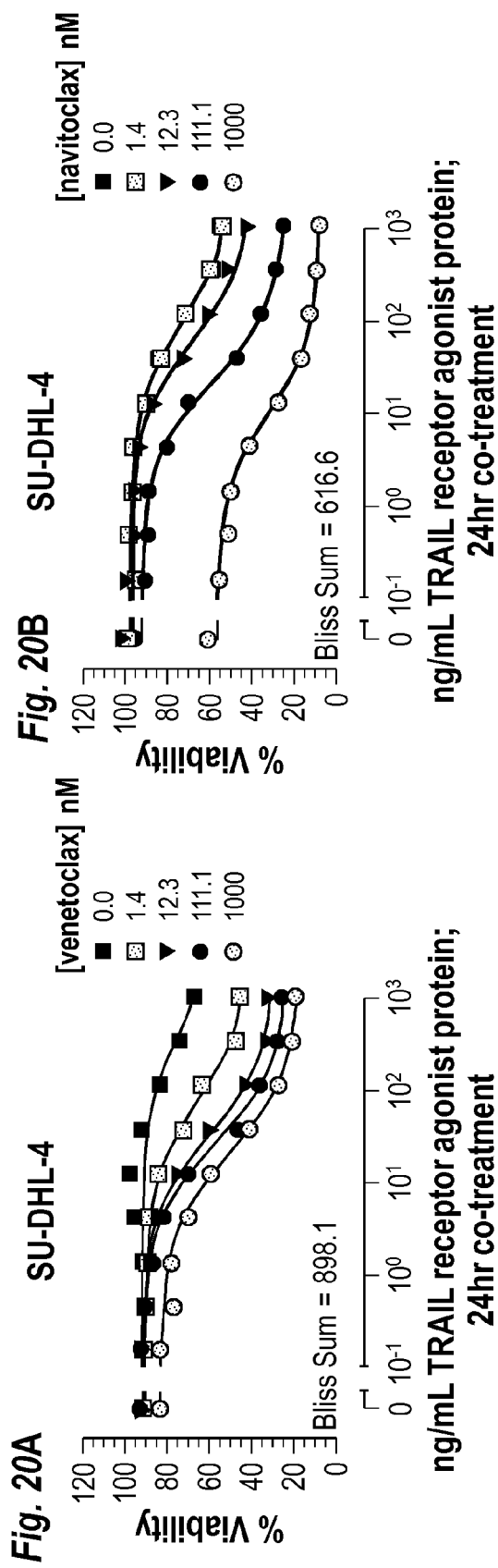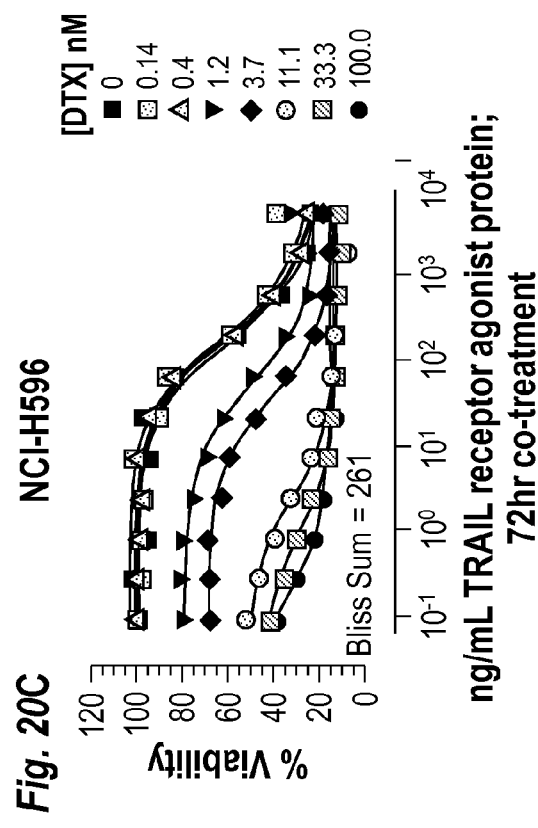
Fig. 20A, Fig. 20B, Fig. 20C

Treatment regimens shown refer to amounts of TRAIL receptor agonist protein

Treatment regimens shown refer to amounts of TRAIL receptor agonist protein

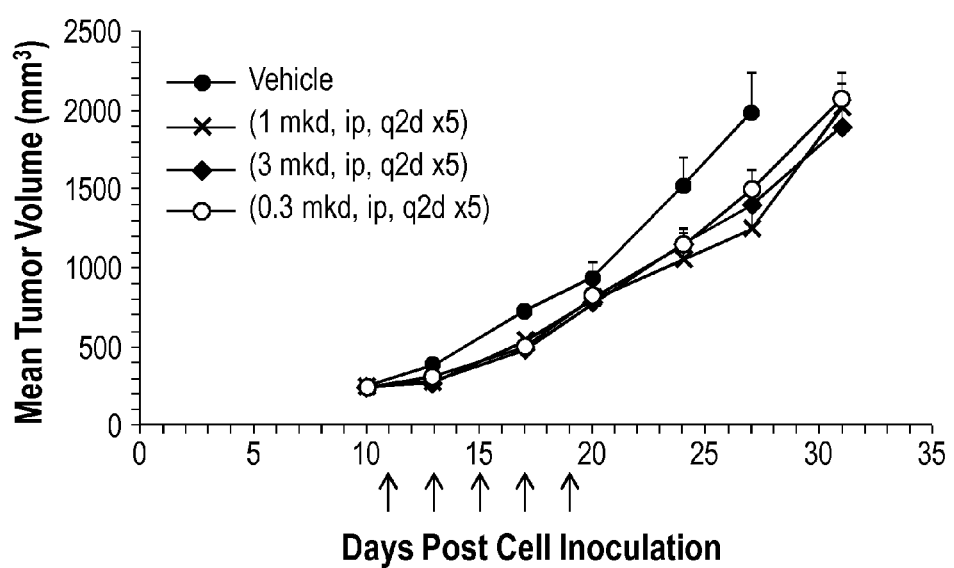
Fig. 23 Treatment regimens shown refer to amounts of TRAIL receptor agonist protein

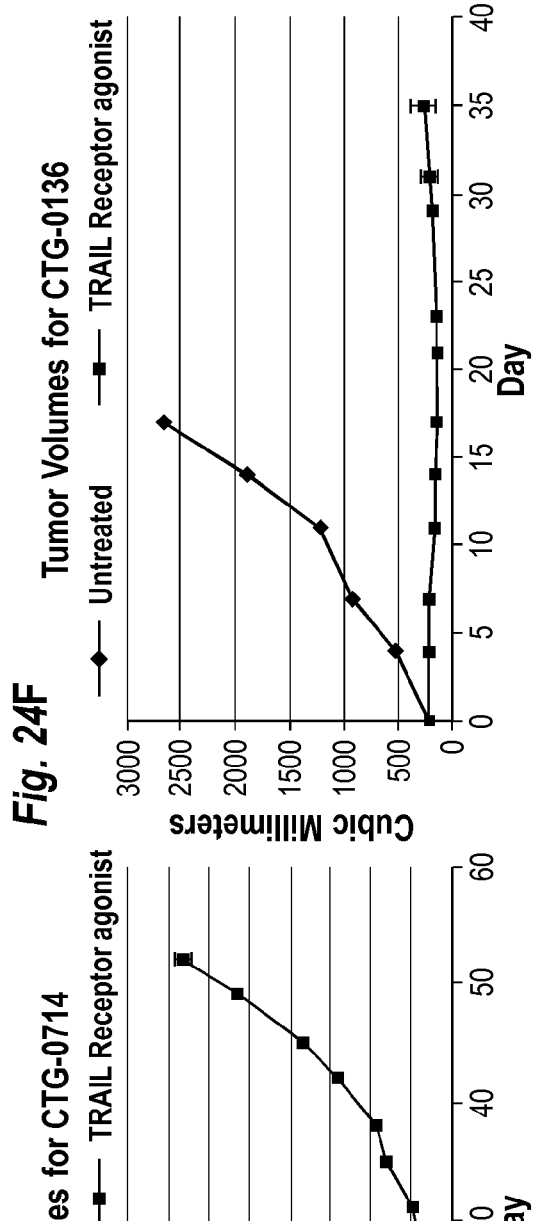
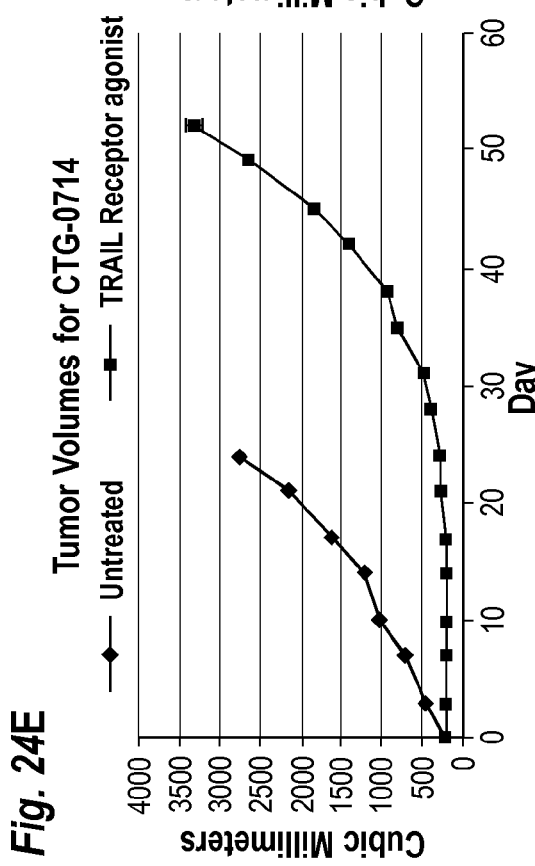
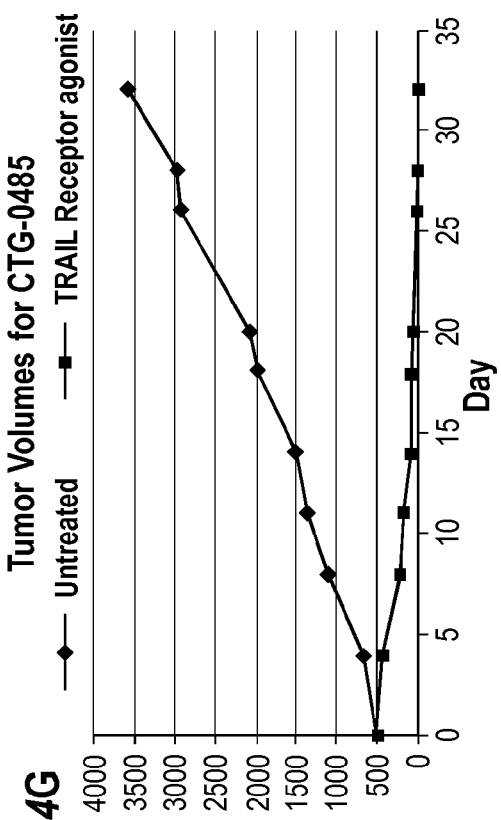

SINGLE-CHAIN TRAIL-RECEPTOR AGONIST PROTEINS

RELATED APPLICATIONS

The instant application claims the benefit of priority to U.S. Provisional Patent Application No. 61/983,152, filed Apr. 23, 2014, which is incorporated by reference herein in its entirety.

FIELD OF THE INVENTION

The present invention provides specific TRAIL receptor agonist proteins comprising three soluble TRAIL domains and an Fc fragment, nucleic acid molecules encoding the TRAIL receptor agonist proteins, and uses thereof. The TRAIL receptor agonist proteins are substantially non-aggregating and suitable for therapeutic, diagnostic and/or research applications.

BACKGROUND OF THE INVENTION

It is known that trimerization of TNF superfamily (TNFSF) cytokines is required for efficient receptor binding and activation. Trimeric complexes of TNF superfamily cytokines, however, are difficult to prepare from recombinant monomeric units.

WO 01/49866 and WO 02/09055 disclose recombinant fusion proteins comprising a TNF cytokine and a multimerization component, particularly a protein from the C1q protein family or a collectin. A disadvantage of these fusion proteins is, however, that the trimerization domain usually has a large molecular weight and/or that the trimerization is rather inefficient.

Schneider et al. (J Exp Med 187 (1989), 1205-1213) describe that trimers of TNF cytokines are stabilized by N-terminally positioned stabilization motifs. In CD95L, the stabilization of the receptor binding domain trimer is presumably caused by N-terminal amino acid domains which are located near the cytoplasmic membrane.

Shiraishi et al. (Biochem Biophys Res Commun 322 (2004), 197-202) describe that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of heptad-repeats in the coiled-coil zipper motif are difficult to determine. In addition, coiled-coil structures have the tendency to form macromolecular aggregates after alteration of pH and/or ionic strength.

WO 01/25277 relates to single-chain oligomeric polypeptides which bind to an extracellular ligand binding domain of a cellular receptor, wherein the polypeptide comprises at least three receptor binding sites of which at least one is capable of binding to a ligand binding domain of the cellular receptor and at least one is incapable of effectively binding to a ligand binding domain of the cellular receptor, whereby the single-chain oligomeric polypeptides are capable of binding to the receptor, but incapable of activating the receptor. For example, the monomers are derived from cytokine ligands of the TNF family, particularly from TNF-α.

WO 2005/103077 discloses single-chain fusion polypeptides comprising at least three monomers of a TNF family ligand member and at least two peptide linkers that link the monomers of the TNF ligand family members to one another. Recent experiments, however, have shown that these single-chain fusion polypeptides show undesired aggregation.

WO 2010/010051 discloses single-chain fusion polypeptides comprising three soluble TNF family cytokine domains and at least two peptide linkers. The described fusion polypeptides are substantially non-aggregating.

Moreover, previous work, including that of Papadopoulos et al. (Cancer Chemother Pharmacol, 2015, DOI 10.1007/s00280-015-2712-0), has demonstrated that TRAIL receptor superclustering can result in toxicity.

Accordingly, there is a need in the art for novel TRAIL receptor agonists that exhibit high biological activity, high stability, low toxicity, and allow for efficient recombinant manufacturing.

SUMMARY OF THE INVENTION

The present invention provides specific TRAIL receptor agonist proteins that exhibit low proteolytic degradation, long half-life, and low TRAIL receptor superclustering in vivo (along with concomitant toxicity).

The TRAIL receptor agonist proteins of the instant invention generally comprise: (i) a first soluble TRAIL cytokine domain; (ii) a first peptide linker; (iii) a second soluble TRAIL domain; (iv) a second peptide linker; (v) a third soluble TRAIL domain; and (vi) an antibody Fc fragment.

In one aspect, the present invention provides a single-chain fusion polypeptide comprising: (i) a first soluble TRAIL domain, (ii) a first peptide linker, (iii) a second soluble TRAIL domain, (iv) a second peptide linker, (v) a third soluble TRAIL domain, and (vi) an antibody Fc fragment. In one embodiment, the antibody Fc fragment (vi) is located N terminal to the first TRAIL domain (i) and/or C-terminal to the third TRAIL domain (v). In another embodiment the antibody Fc fragment is located C-terminally to the third TRAIL domain (v). In one embodiment, the polypeptide is substantially non aggregating. In another embodiment, the second and/or third soluble TRAIL domain is an N-terminally shortened domain which optionally comprises amino acid sequence mutations.

In one embodiment, at least one of the soluble TRAIL domains, particularly at least one of the soluble TRAIL domains (iii) and (v), is a soluble TRAIL domain with an N-terminal sequence which starts between amino acid Gln120 and Val122 of human TRAIL and wherein Arg121 may be replaced by a neutral amino acid, e.g., Ser or Gly. In another embodiment, at least one of the soluble TRAIL domains, particularly at least one of the soluble TRAIL domains (iii) and (v), is a soluble TRAIL domain with an N-terminal sequence selected from (a) Arg121-Val122-Ala123 and (b) (Gly/Ser)121-Val122-Ala123. In one embodiment, the soluble TRAIL domain ends with amino acid Gly281 of human TRAIL and/or optionally comprises a mutation at positions R130, G160, H168, R170, H177, Y189, R191, Q193, E195, N199, K201, Y213, T214, S215, H264, I266, D267 or D269 or at two or more of said positions. In one embodiment, the soluble TRAIL domain (i) consists of amino acids Gln120-Gly281 of human TRAIL according to SEQ ID NO: 1 and the soluble TRAIL domains (iii) and (v) consist of amino acids Arg121-Gly281 of human TRAIL according to SEQ ID NO: 1.

In one embodiment, the first and second peptide linkers (ii) and (iv) independently have a length of 3-8 amino acids, particularly a length of 3, 4, 5, 6, 7, or 8 amino acids, and preferably are glycine/serine linkers, optionally comprising an asparagine residue which may be glycosylated. In one embodiment, the first and the second peptide linkers (ii) and (iv) consist of the amino acid sequence according to SEQ ID NO: 2. In another embodiment, the polypeptide additionally comprises an N-terminal signal peptide domain, e.g., of SEQ ID NO: 12, which may comprise a protease cleavage site, and/or which additionally comprises a C-terminal element which may comprise and/or connect to a recognition/purification domain, e.g., a Strep-tag according to SEQ ID NO: 13.

In one embodiment, the antibody Fc fragment (vi) is fused to the soluble TRAIL domain (i) and/or (v) via a hinge-linker, preferably of SEQ ID NO: 11. In another embodiment, the antibody Fc fragment (vi) consists of the amino acid sequence as shown in SEQ ID NO: 10 or 17. In one embodiment, the polypeptide comprises the amino acid sequence of SEQ ID NO: 14, 15 or 18.

In another aspect, the present invention provides a TRAIL receptor agonist protein comprising a polypeptide having the amino acid sequence set forth in SEQ ID NO: 19, 20 or 21.

In another aspect, the present invention provides a TRAIL receptor agonist protein comprising a polypeptide having the amino acid sequence set forth in SEQ ID NO: 26, 27, 28, 29, or 30.

In another aspect, the present invention provides a TRAIL receptor agonist protein comprising two polypeptides having the amino acid sequence set forth in SEQ ID NO: 19. In one embodiment, the two polypeptides are covalently linked through three interchain disulfide bonds formed between cysteine residues 513, 519, and 522 of each polypeptide.

In one embodiment, one or more of the asparagine residues at positions 168 and 337 of the polypeptide(s) are N-glycosylated. In another embodiment, the asparagine residues at positions 168 and 337 of the polypeptide(s) are both N-glycosylated.

In another embodiment, the polypeptide(s) are further post-translationally modified. In another embodiment, the post-translational modification comprises the N-terminal glutamine modified to pyroglutamate.

In another aspect, the present invention provides a pharmaceutical composition comprising a TRAIL receptor agonist protein disclosed herein and one or more pharmaceutically acceptable carriers, diluents, excipients, and/or adjuvants. In another aspect, the present invention provides a nucleic acid molecule encoding the TRAIL receptor agonist protein. In another embodiment, the present invention provides an expression vector comprising the nucleic acid molecule. In another embodiment, the present invention provides a cell comprising the nucleic acid molecule. In a further embodiment, the cell is a eukaryotic cell. In another embodiment, the cell is a mammalian cell. In another embodiment, the cell is a Chinese Hamster Ovary (CHO) cell. In other embodiments, the cell is selected from the group consisting of CHO-DBX11, CHO-DG44, CHO-S, and CHO-K1 cells. In other embodiments, the cell is selected from the group consisting of Vero, BHK, HeLa, COS, MDCK, HEK-293, NIH-3T3, W138, BT483, Hs578T, HTB2, BT20, T47D, NS0, CRL7030, HsS78Bst, PER.C6, SP2/0-Agl4, and hybridoma cells.

In another aspect, the present invention provides a method of treating a subject having a TRAIL-associated disease or disorder, the method comprising administering to the subject an effective amount of the TRAIL receptor agonist protein. In one embodiment, the TRAIL receptor agonist protein is administered alone. In another embodiment, the TRAIL receptor agonist protein is administered before, concurrently, or after the administration of a second agent. In another embodiment, the disease or disorder is selected from the group consisting of: tumors, infectious diseases, inflammatory diseases, metabolic diseases, autoimmune disorders, degenerative diseases, apoptosis-associated diseases, and transplant rejections. In one embodiment, the tumors are solid tumors. In one embodiment, the tumors arise from the group of cancers consisting of sarcoma, esophageal cancer, and gastric cancer. In another embodiment, the tumors arise from Ewing's sarcoma or fibrosarcoma, In another embodiment, the tumors arise from the group of cancers consisting of Non-Small Cell Lung Carcinoma (NSCLC), pancreatic cancer, colorectal cancer, breast cancer, ovarian cancer, head and neck cancers, and Small Cell Lung Cancer (SCLC). In another embodiment, the tumors are lymphatic tumors. In one embodiment, the tumors are hematologic tumors. In another embodiment, the tumors arise from non-Hodgkin's lymphoma, leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), or hairy cell leukemia. In another embodiment, the autoimmune disorders are rheumatoid diseases, arthritic diseases, or rheumatoid and arthritic diseases. In a further embodiment, the disease or disorder is rheumatoid arthritis. In another embodiment, the degenerative disease is a neurodegenerative disease. In a further embodiment, the neurodegenerative disease is multiple sclerosis.

In one embodiment, the second agent is a chemotherapeutic, radiotherapeutic, or biological agent. In one embodiment, the second agent is selected from the group consisting of Duvelisib, Ibrutinib, Navitoclax, and Venetoclax, In another embodiment, the second agent is an apoptotic agent. In one embodiment, the apoptotic second agent is selected from the group consisting of Bortezomib, Azacitidine, Dasatinib, and Gefitinib. In a particular embodiment, the pharmaceutical compositions disclosed herein are administered to a patient by intravenous or subcutaneous administration. In other embodiments, the disclosed pharmaceutical compositions are administered to a patient byoral, parenteral, intramuscular, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

In one embodiment, the TRAIL receptor agonist protein is administered as a single bolus. In another embodiment, TRAIL receptor agonist protein may be administered over several divided doses. The TRAIL receptor agonist protein can be administered at about 0.1-100 mg/kg. In one embodiment, the TRAIL receptor agonist protein can be administered at a dosage selected from the group consisting of: about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, and 10-100 mg/kg. In other embodiments, the TRAIL receptor agonist protein is present in pharmaceutical compositions at about 0.1-100 mg/ml. In one embodiment, the TRAIL receptor agonist protein is present in pharmaceutical compositions at an amount selected from the group consisting of: about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml. In other embodiments, a therapeutically effective amount of TRAIL receptor agonist protein is administered to a subject. In another embodiment, a prophylactically effective amount of TRAIL receptor agonist protein is administered to a subject.

BRIEF DESCRIPTION OF THE DRAWINGS

FIG. 1 Domain structure of a single-chain fusion polypeptide comprising three TRAIL domains. I., II., III. Soluble TRAIL domains.

FIG. 17A The exemplary TRAIL receptor agonist protein as shown with the N-terminal signal peptide domain is set forth in SEQ ID NO: 14. The mature protein (which does not include the N-terminal signal peptide domain) is set forth in SEQ ID NO: 19.

FIGS. 20A-20C A TRAIL receptor agonist protein comprising two polypeptides having the amino acid sequence set forth in SEQ ID NO: 19 synergizes with anti-tumorigenic agents in vitro. SU-DHL-4 cells were incubated with increasing concentrations of the TRAIL receptor agonist protein in the presence or absence of the indicated concentrations of venetoclax (FIG. 20A) or navitoclax (FIG. 20B) for 24 hours. Alternatively, (FIG. 20C) NCI-H596 cells were treated with increasing concentrations of the TRAIL receptor agonist protein in the presence or absence of the indicated concentrations of docetaxel (DTX) for 72 hours. Cell viability was assessed and synergy determined by Bliss sum.

FIG. 23 Effect of TRAIL receptor agonist protein comprising two polypeptides having the amino acid sequence set forth in SEQ ID NO: 19 on tumor growth in the H460LM non-small cell lung xenograft model.

FIGS. 24A-24G Effect of TRAIL receptor agonist protein comprising two polypeptides having the amino acid sequence set forth in SEQ ID NO: 19 on tumor growth in PDX models. Diamonds, TRAIL receptor agonist protein-treated; Squares, untreated. Tumor volumes are shown for (FIG. 24A) CTG-0069, (FIG. 24B) CTG-0167, (FIG. 24C) CTG-0293, (FIG. 24D) CTG-0785, (FIG. 24E) CTG-0714, (FIG. 24F) CTG-0136, and (FIG. 24G) CTG-0485.

DETAILED DESCRIPTION OF THE INVENTION

According to the present invention, it was found that fusing a single-chain TRAIL receptor-binding domain to an Fc domain results in a hexavalent TRAIL receptor agonist providing high biological activity combined with good stability. Accordingly, a single-chain fusion polypeptide comprising at least three soluble TRAIL domains connected by two peptide linkers and N-terminally and/or C-terminally an antibody Fc fragment, is provided.

Preferably, the single-chain fusion polypeptide is non-aggregating. The term "non-aggregating" refers to a monomer content of the preparation of ≥50%, preferably ≥70% and more preferably ≥90%. The ratio of monomer content to aggregate content may be determined by examining the amount of aggregate formation using size-exclusion chromatography (SEC). The stability concerning aggregation may be determined by SEC after defined time periods, e.g. from a few to several days, to weeks and months under different storage conditions, e.g. at 4° C. or 25° C. For the fusion protein, in order to be classified as substantially non-aggregating, it is preferred that the monomer content is as defined above after a time period of several days, e.g. 10 days, more preferably after several weeks, e.g. 2, 3 or 4 weeks, and most preferably after several months, e.g. 2 or 3 months of storage at 4° C., or 25° C.

The single-chain fusion polypeptide may comprise additional domains which may be located at the N- and/or C-termini thereof. Examples for additional fusion domains are e.g. an N-terminal signal peptide domain which may comprise a protease cleave site or a C-terminal element which may comprise and/or connect to a recognition/purification domain. According to a preferred embodiment, the fusion polypeptide comprises a Strep-tag at its C-terminus that is fused via a linker. An exemplary Strep-tag including a short serine linker is shown in SEQ ID NO: 13.

The TRAIL receptor agonist protein of the present invention comprises three soluble domains derived from TRAIL. Preferably, those soluble domains are derived from a mammalian, particularly human TRAIL including allelic variants and/or derivatives thereof. The soluble domains comprise the extracellular portion of TRAIL including the receptor binding domain without membrane located domains. Like other proteins of the TNF superfamily, TRAIL is anchored to the membrane via an N-terminal portion of 15-30 amino acids, the so-called stalk-region. The stalk region contributes to trimerization and provides a certain distance to the cell membrane. However, the stalk region is not part of the receptor binding domain (RBD).

Figure 2:
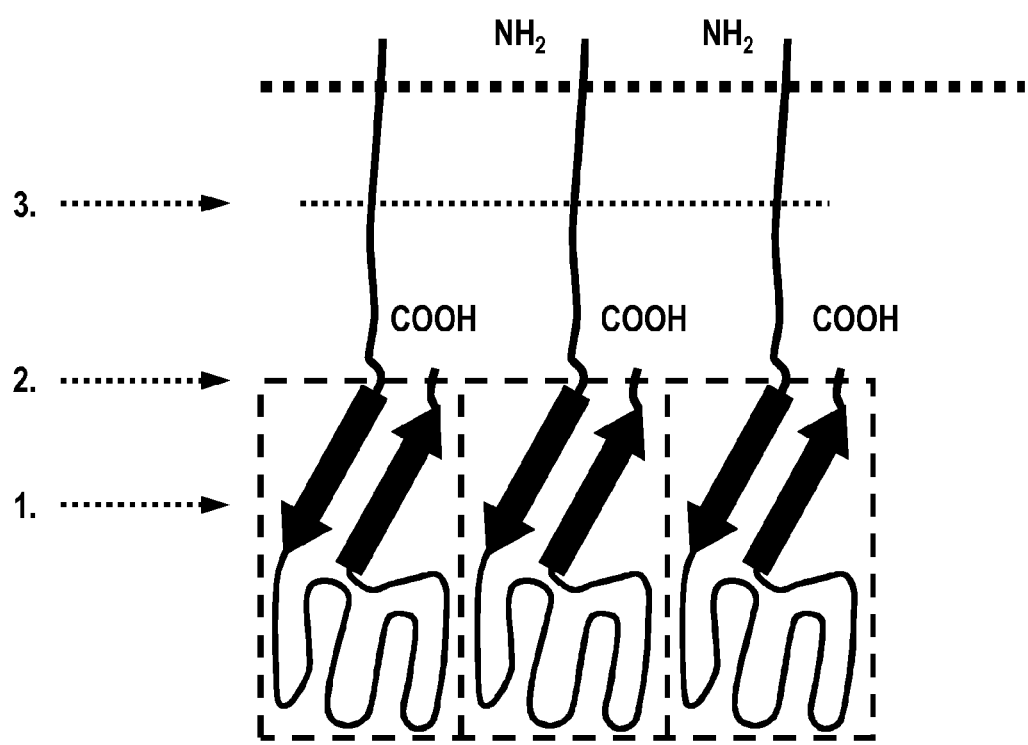
FIG. 2 Schematic picture representing the general structure of TRAIL.
Cell membrane, N-terminus located within the cell,
1. anti-parallel β-fold of receptor-binding domain (RBD),
2. interface of RBD and cell membrane,
3. protease cleavage site.
Figure 3:
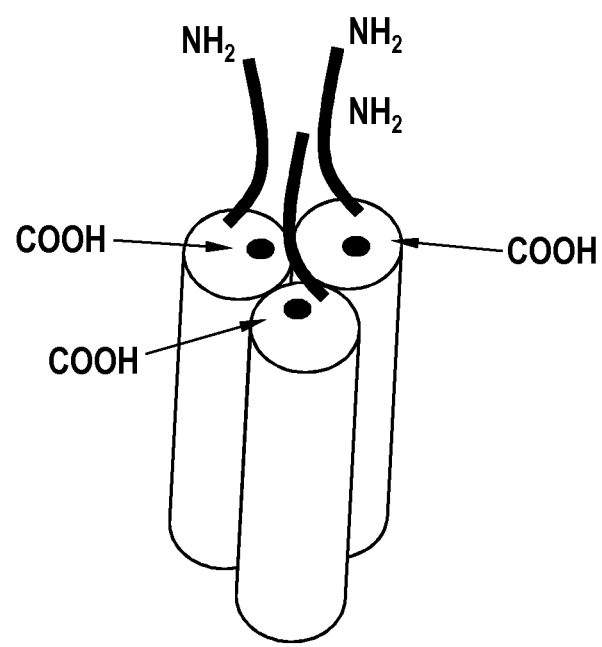
FIG. 3 Schematic picture representing the structure of the native TRAIL trimer. Cylindric structures represent RBDs. N-termini connect RBDs with the cell membrane.

Importantly, the RBD is characterized by a particular localization of its N- and C-terminal amino acids. Said amino acids are immediately adjacent and are located centrally to the axis of the trimer. The first N-terminal amino acids of the RBD form an anti-parallel beta-strand with the C-terminal amino acids of the RBD (FIGS. 2 and 3).

Figure 4:
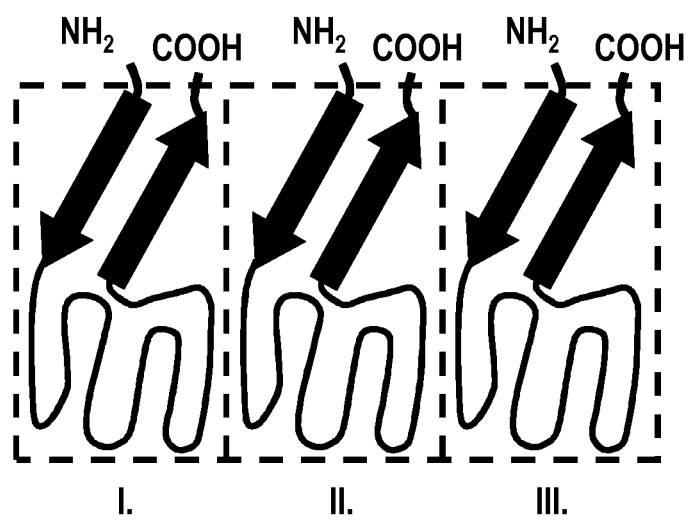
FIG. 4 Schematic picture representing the structure of three soluble domains comprising the receptor-binding domain of a TRAIL. I., II., III. soluble TRAIL domains.
Figure 5:
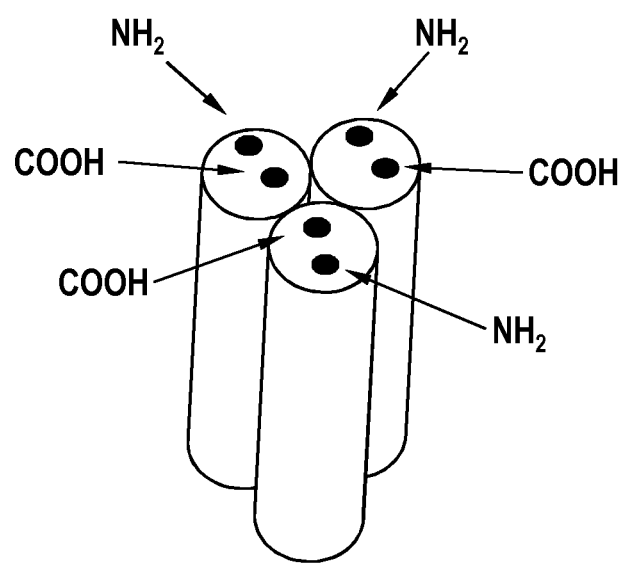
FIG. 5 Trimerization of the soluble domains comprising the RBD of TRAIL, characterized in that the N- and C-termini of the three soluble domains form a surface.
Figure 6:
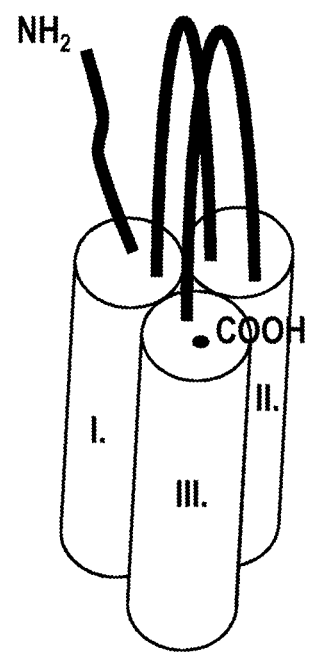
FIG. 6 Schematic picture representing the structure of the single-chain TRAIL comprising all or a part of the stalk-region illustrating the requirement of longer linkers to compensate for the distance to the N-terminus of the next FIG. 7 scFv-TRAIL fusion protein known from the art.
Figure 7:
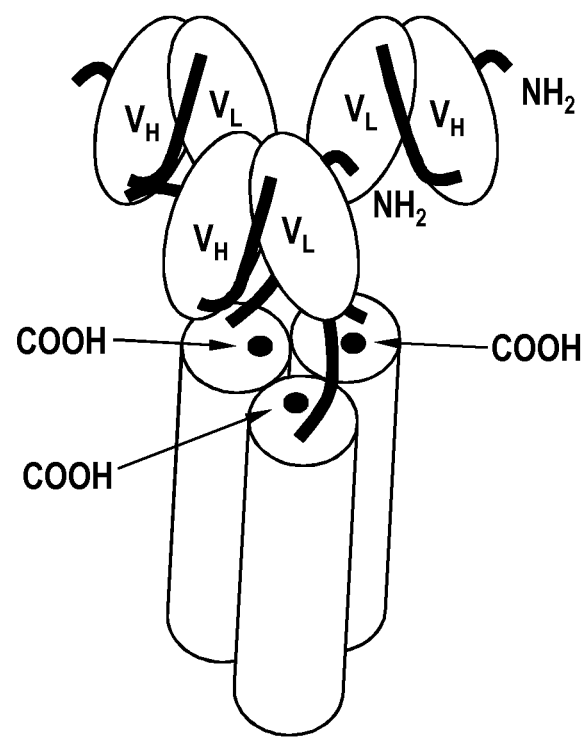
Figure 8:
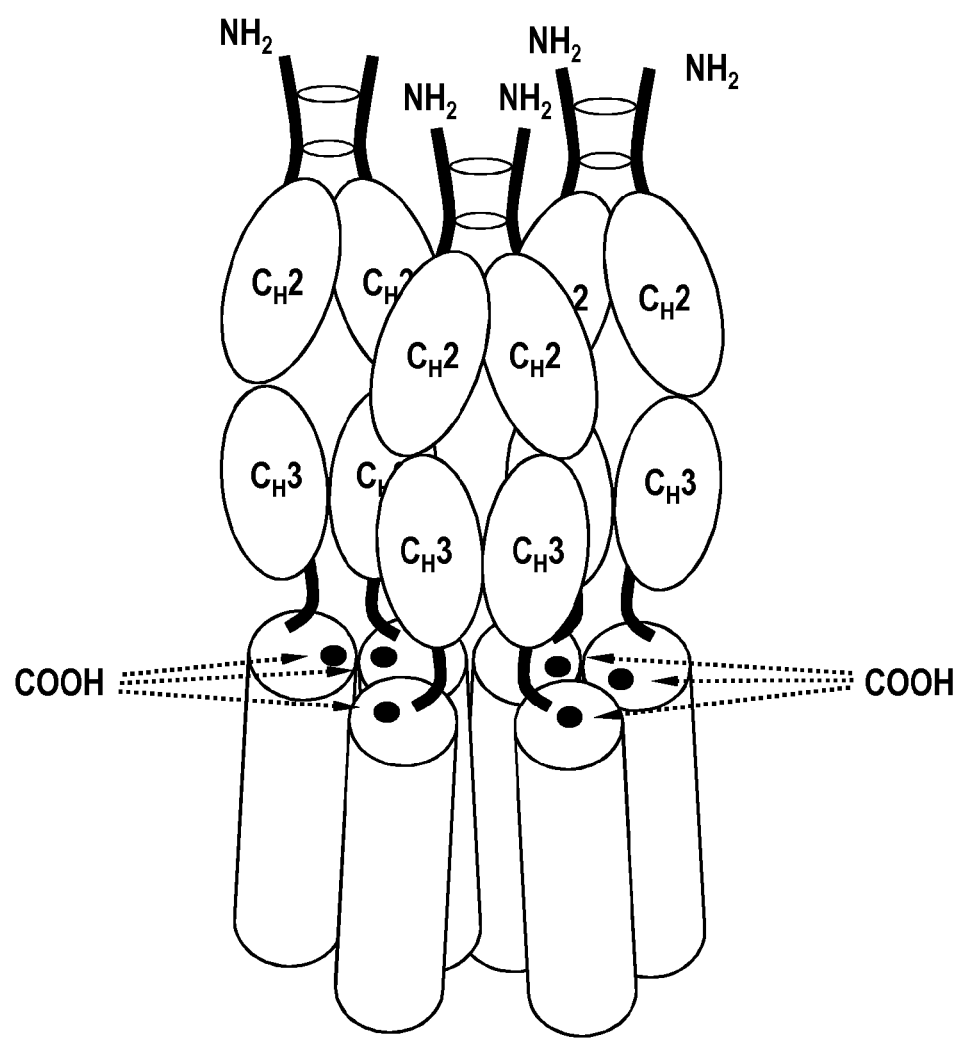
FIG. 8 Fc-TRAIL fusion protein known from the art.
Figures 9A, 9B:
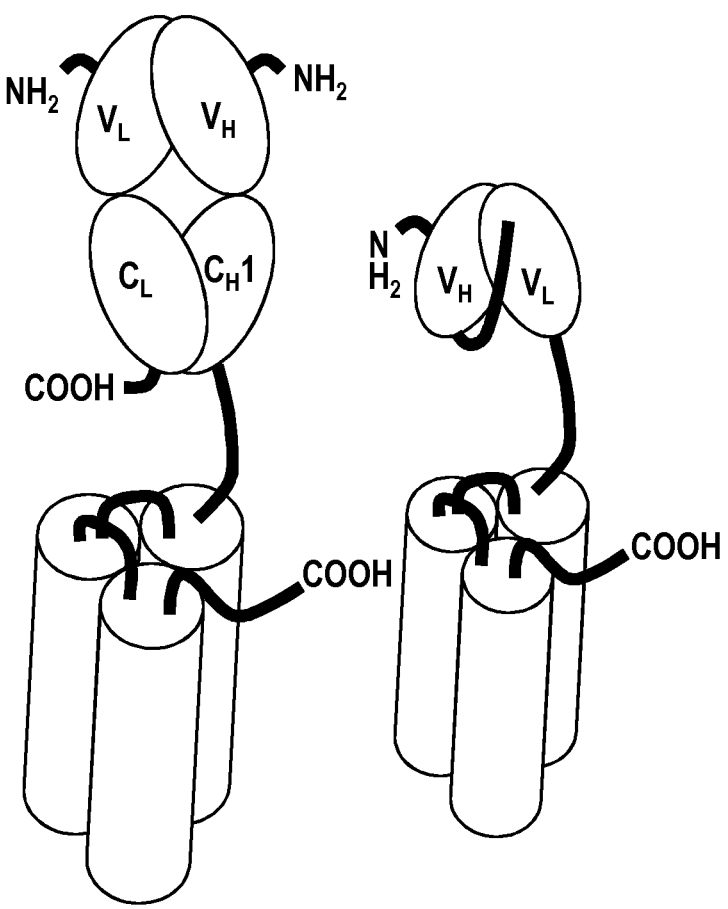
FIG. 9A Single-chain fusion polypeptide comprising an additional Fab antibody fragment.
FIG. 9B Single-chain fusion polypeptide comprising an additional scFv antibody fragment.
Figure 10:
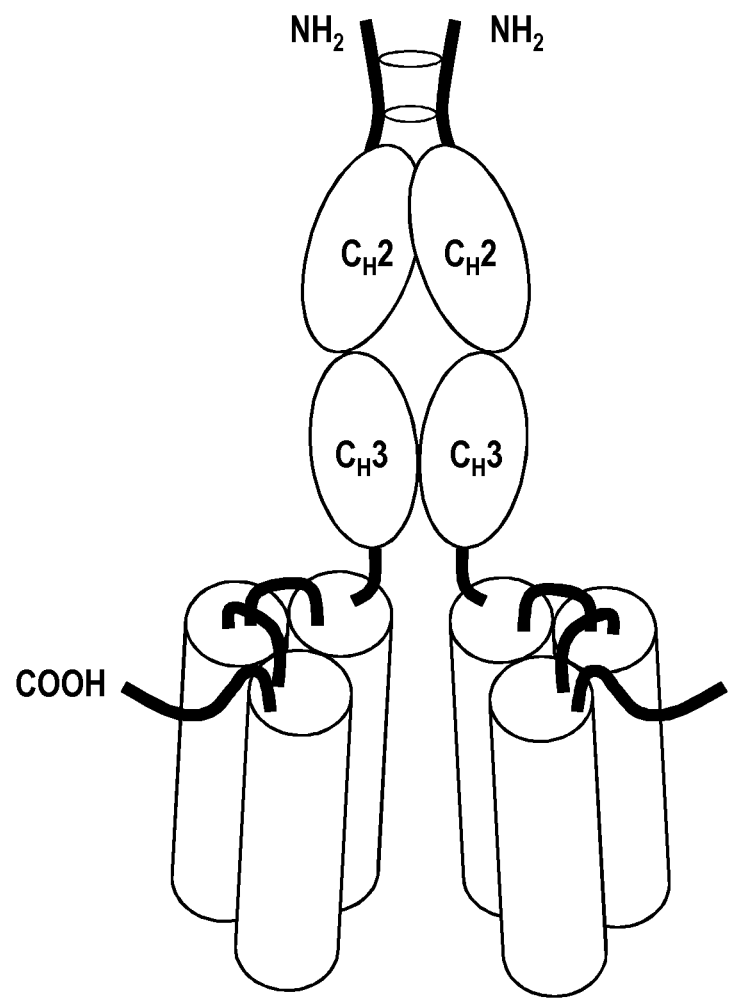
FIG. 10 Dimerization of two N-terminally fused scFc fusion polypeptides via disulfide bridges.
Figure 11:
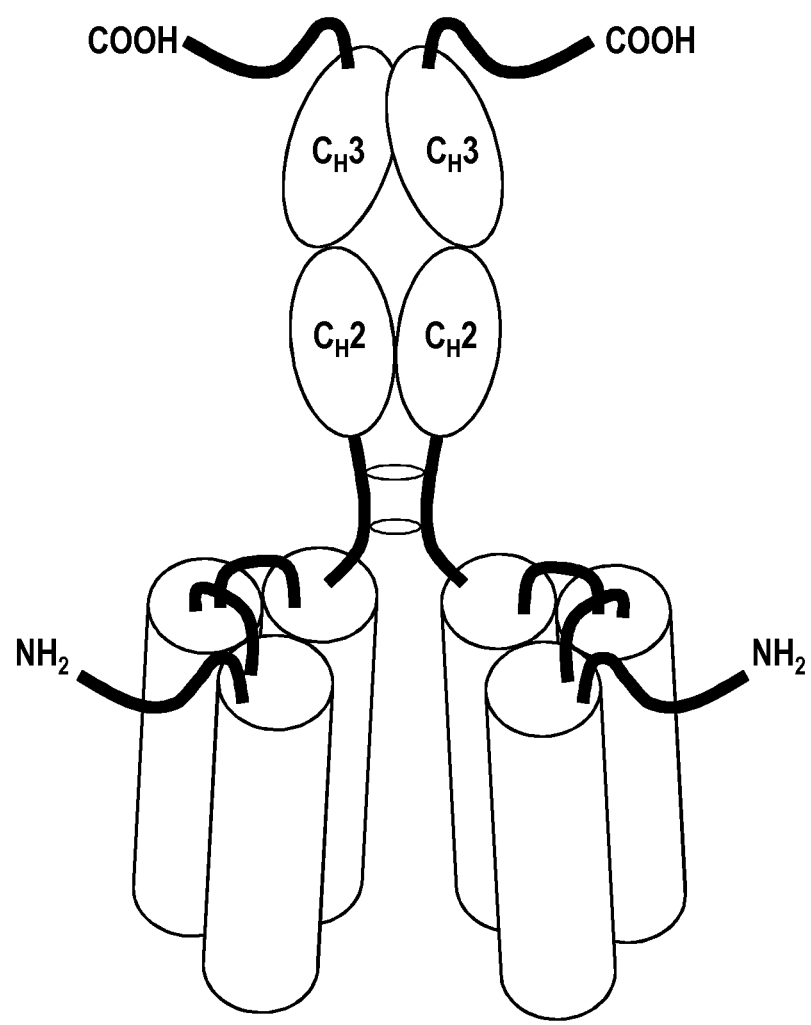
FIG. 11 Dimerization of two C-terminally fused scFc fusion polypeptides via disulfide bridges.
Figure 12:
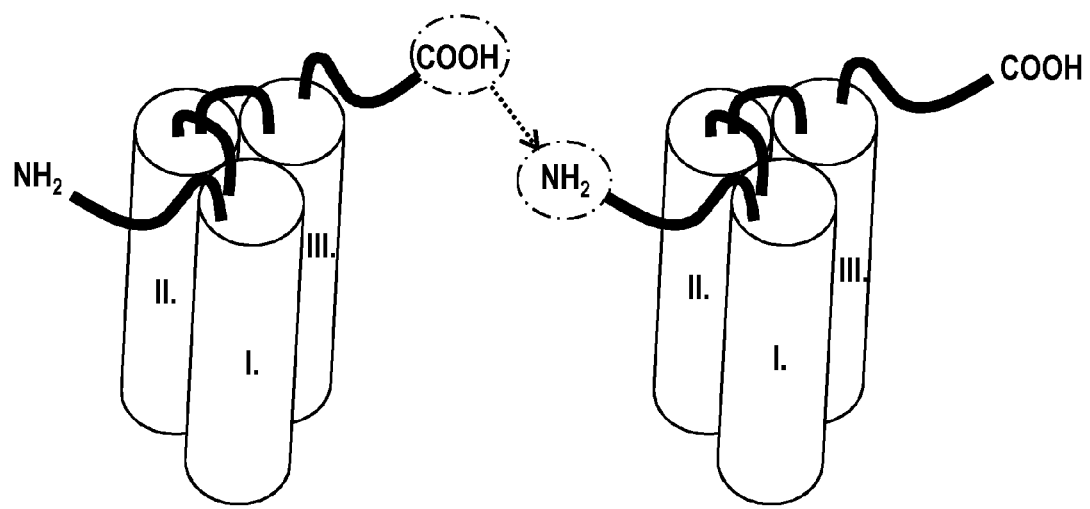
FIG. 12 Dimerization of single-chain fusion polypeptides via a linker.
Figure 13:
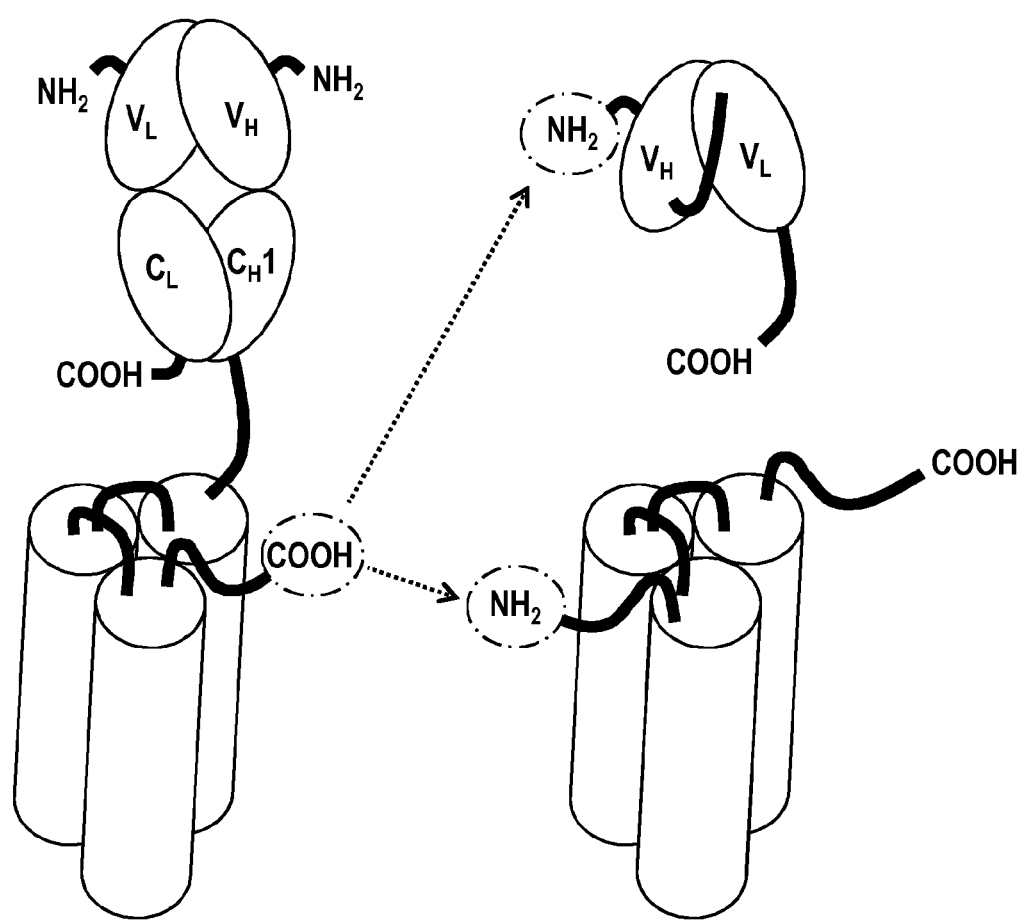
FIG. 13 Single-chain fusion polypeptide comprising an additional Fab antibody fragment further fused to a second fusion polypeptide or to a scFv fusion polypeptide.
Figure 14:
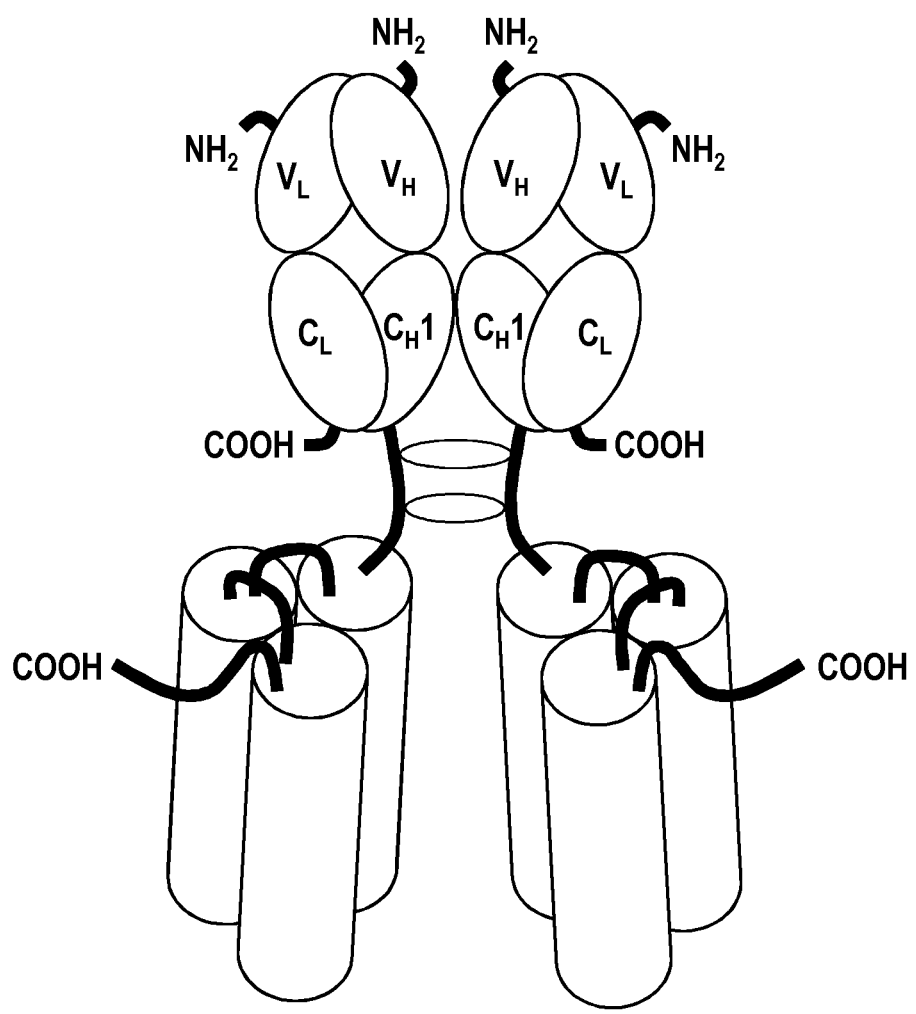
FIG. 14 Dimerization of two scFab fusion polypeptides via disulfide bridges.
Figure 15:
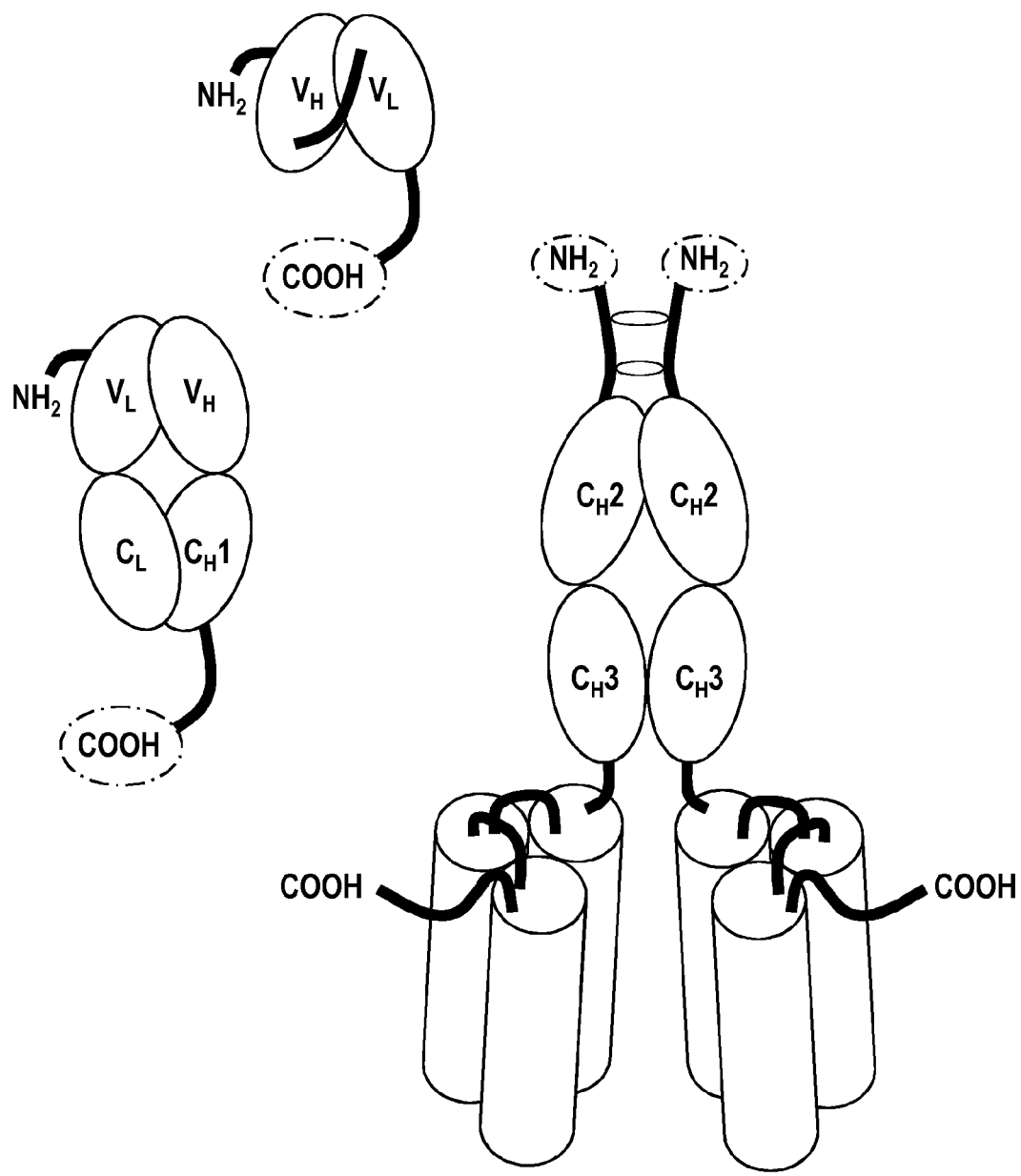
FIG. 15 N-terminally fused scFc fusion polypeptides further comprising a Fv and/or Fab antibody fragment.
Figure 16:
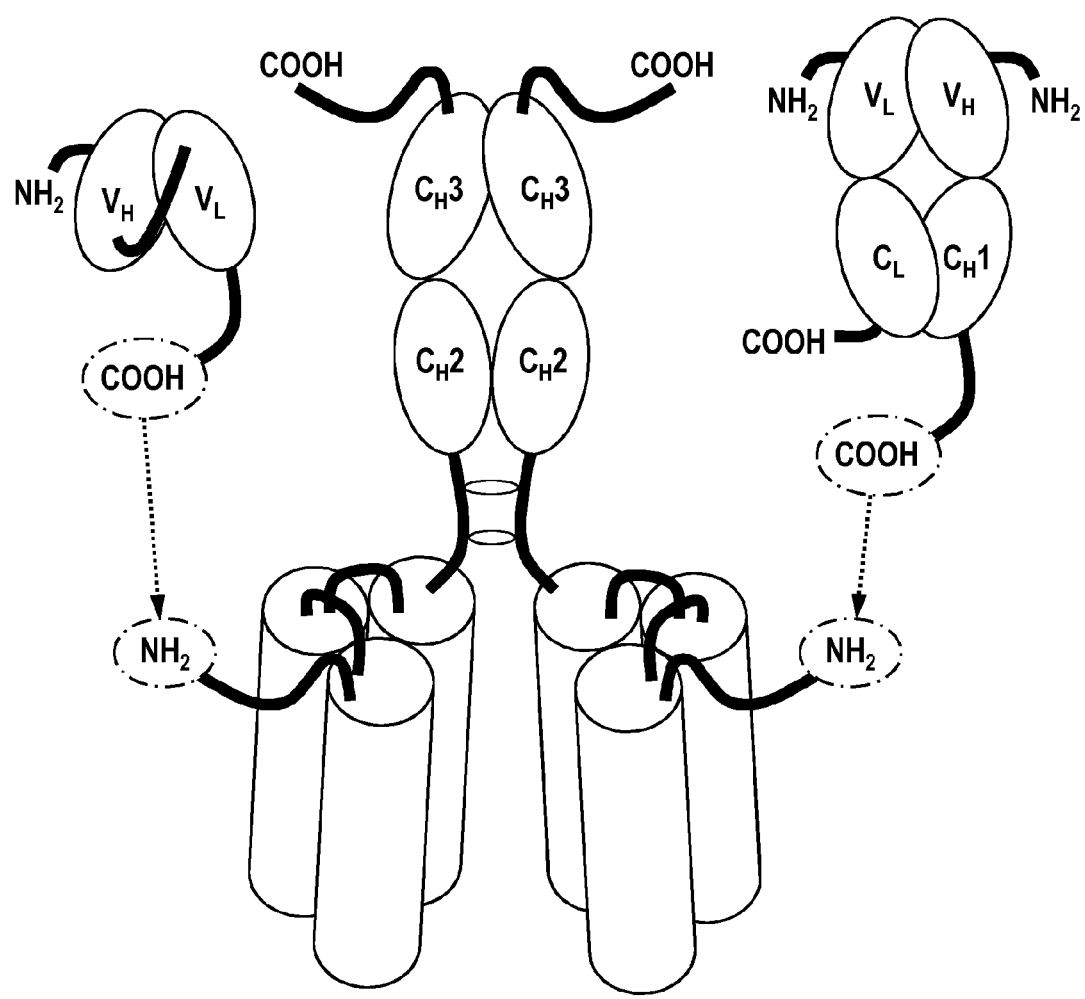
FIG. 16 C-terminally fused scFc fusion polypeptides further comprising a Fv and/or Fab antibody fragment.
Figure 17B:
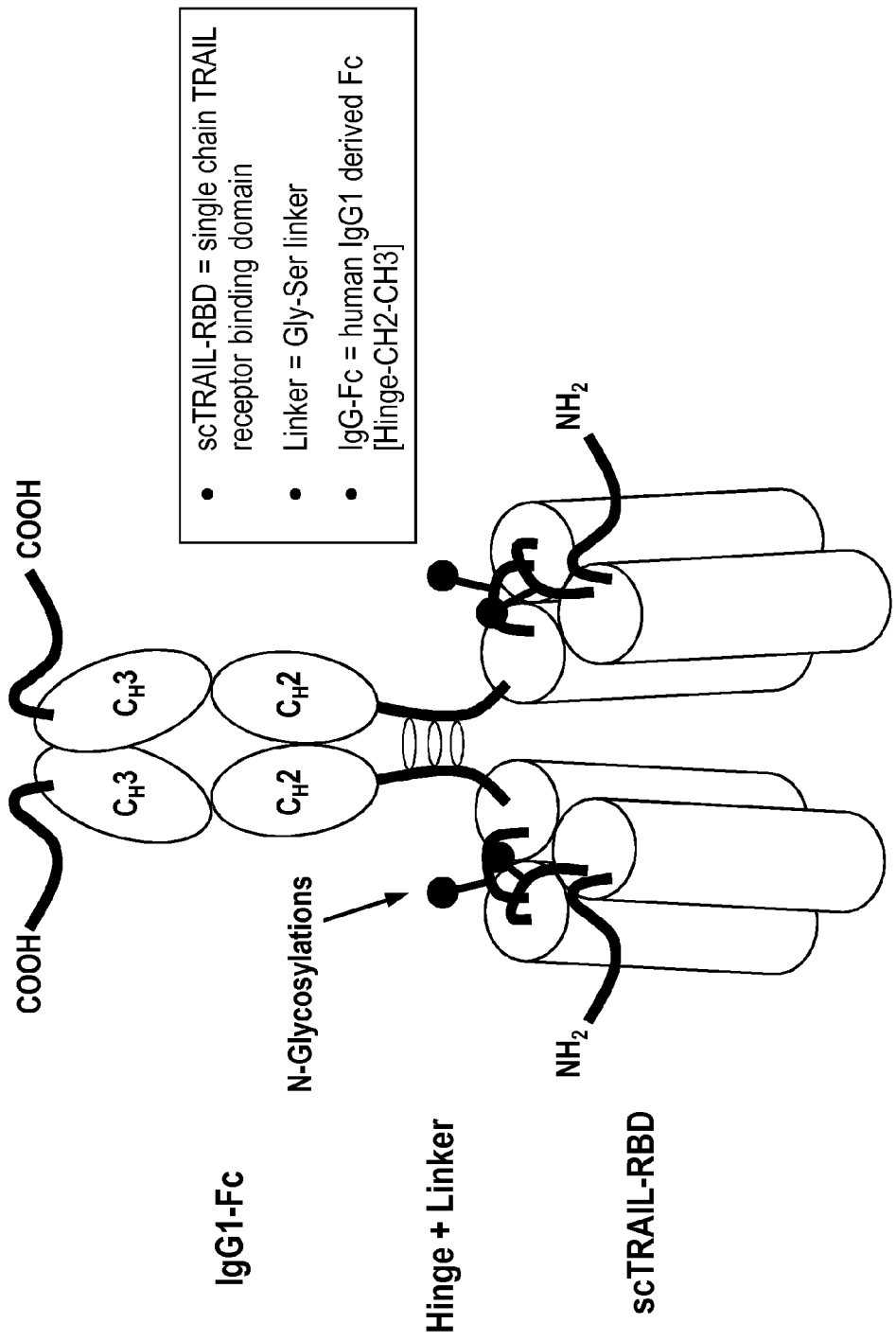
FIG. 17B Schematic picture representing the overall structure and annotated sequence of an exemplary TRAIL receptor agonist protein.

Thus, the anti-parallel beta-strand of the RBD forms an interface with the cell membrane, which is connected to and anchored within the cell membrane via the amino acids of the stalk region. It is highly preferred that the soluble TRAIL domains of the TRAIL receptor agonist protein comprise a receptor binding domain of the TRAIL lacking any amino acids from the stalk region (FIGS. 4 and 5). Otherwise, a long linker connecting the C-terminus of one of the soluble domains with the N-terminus of the next soluble domain would be required to compensate for the N-terminal stalk-region of the next soluble domain (FIG. 6), which might result in instability and/or formation of aggregates.

A further advantage of such soluble domains is that the N- and C-terminal amino acids of the RBD are not accessible for any anti-drug antibodies. Preferably, the single-chain fusion polypeptide is capable of forming an ordered trimeric structure comprising at least one functional binding site for the respective TRAIL receptor.

The TRAIL receptor agonist protein comprises three functional TRAIL receptor binding sites, i.e. amino acid sequences capable of forming a complex with a TRAIL receptor. Thus, the soluble domains are capable of binding to the corresponding TRAIL receptor. In one embodiment, at least one of the soluble domains is capable of receptor activation, whereby apoptotic and/or proliferative activity may be affected. In a further embodiment, one or more of the soluble domains are selected as not being capable of receptor activation.

The soluble TRAIL domain may be derived from human TRAIL as shown in SEQ ID NO: 1. Preferably, the soluble TRAIL domains are derived from human TRAIL, particularly starting from amino acids 120-122 and comprise particularly amino acids 120-281, 121-281 or 122-281 of SEQ ID NO: 1. Optionally, amino acid Arg121 of SEQ ID NO: 1 may be replaced by a non-charged amino acid, e.g. Ser or Gly.

TABLE 1

Sequence of Human TRAIL Protein

| SEQ ID NO | Sequence |
|---|---|
| 1 | MAMMEVQGGPSLGQTCVLIVIFTVLLQSLCVAVTYVYFTNELK QMQDKYSKSGIACFLKEDDSYWDPNDEESMNSPCWQVKWQ LRQLVRKMILRTSEETISTVQEKQQNISPLVRERGPORVAAHI TGTRGRSNTLSSPNSKNEKALGRKINSWESSRSGHSFLSNLH LRNGELVIHEKGFYYIYSQTYFRFQEEIKENTKNDKQMVQYIY KYTSYPDPILLMKSARNSCWSKDAEYGLYSIYQGGIFELKEND RIFVSVTNEHLIDMDHEASFFGAFLVG |

As indicated above, the soluble TRAIL domains may comprise the wild-type sequences as indicated in SEQ ID NO: 1. It should be noted, however, that it is possible to introduce mutations in one or more of these soluble domains, e.g. mutations which alter (e.g. increase or decrease) the binding properties of the soluble domains. In one embodiment, soluble domains may be selected which cannot bind to the corresponding cytokine receptor.

In a further preferred embodiment of the invention, the soluble TRAIL domain (i) comprises a mutant of TRAIL or a receptor binding domain thereof which binds and/or activates TRAIL-receptor 1 (TRAILR1) and/or TRAIL-receptor 2 (TRAILR2). The binding and/or activity of the mutant may be, e.g., determined by the assays as described in van der Sloot et al. (PNAS, 2006, 103:8634-8639), Kelley et al. (J. Biol. Chem., 2005, 280:2205-2215), or MacFarlane et al. (Cancer Res., 2005, 65: 11265-11270).

The mutant may be generated by any technique and is known by the skilled person, e.g., the techniques described in van der Sloot et al. (PNAS, 2006, 103:8634-8639), Kelley et al. (J. Biol. Chem., 2005, 280:2205-2215), or MacFarlane et al. (Cancer Res., 2005, 65: 11265-11270) and may comprise any type of structural mutations, e.g., substitution, deletion, duplication and/or insertion of an amino acid. A preferred embodiment is the generation of substitutions. The substitution may affect at least one amino acid of TRAIL or a receptor binding domain thereof as described herein. In a preferred embodiment, the substitution may affect at least one of the amino acids of TRAIL, e.g., human TRAIL (e.g., SEQ ID NO: 1). Preferred substitutions in this regard affect at least one of the following amino acids of human TRAIL of SEQ ID NO: 1: R130, G160, Y189, R191, Q193, E195, N199, K201, Y213, T214, S215, H264, I266, D267, D269. Preferred amino acid substitutions of human TRAIL of SEQ ID NO:1 are at least one of the following substitutions: R130E, G160M, Y189A, Y189Q, R191 K, Q193S, Q193R, E195R, N199V, N199R, K201R, Y213W, T214R, S215D, H264R, I266L, D267Q, D269H, D269R, or D269K.

The amino acid substitution(s) may affect the binding and/or activity of TRAIL, e.g., human TRAIL, to or on either the TRAILR1 or the TRAILR2. Alternatively, the amino acid substitution(s) may affect the binding and/or activity of TRAIL, e.g., human TRAIL, to or on both, the TRAILR1 and the TRAILR2. The binding and/or activity of the TRAILR1 and/or TRAILR2 may be affected positively, i.e., stronger, more selective or more specific binding and/or more activation of the receptor. Alternatively, the binding and/or activity of the TRAILR1 and/or TRAILR2 may be affected negatively, i.e., weaker, less selective or less specific binding and/or less or no activation of the receptor.

Examples of mutants of TRAIL with amino acid substitution(s) of the invention that affect binding and/or activation of both TRAILR1 and TRAILR2 may be found, e.g., in Table 1 of MacFarlane et al. (cf. above) and may comprise a human TRAIL mutant with the following two amino acid substitutions of SEQ ID NO: 1 Y213W and S215D or with the following single amino acid substitution: Y189A.

Examples of mutants of TRAIL with amino acid substitution(s) of the invention that affect binding and/or activation of TRAILR1 may be found, e.g., in Table 1 of MacFarlane et al. (cf. above) and may comprise a human TRAIL mutant with the following four amino acid substitutions of SEQ ID NO: 1 N 199V, K201 R, Y213W and S215D or with the following five amino acid substitutions: Q193S, N199V, K201 R, Y213W and S215D, or may be found in Table 2 of Kelley et al. (cf. above) and may comprise a human TRAIL mutant with the following six amino acid substitutions: Y213W, S215D, Y189A, Q193S, N199V, and K201 R, or with Y213W, S215D, Y189A, Q193S, N199R, and K201 R.

Examples of mutants of TRAIL with amino acid substitution(s) of the invention that affect binding and/or activation of TRAILR2 may be found, e.g., in Table 1 of MacFarlane et al. (cf. above) or in Table 2 of Kelley et al. (cf. above) and may comprise a human TRAIL mutant with the following six amino acid substitutions of SEQ ID NO: 1: Y189Q, R191 K, Q193R, H264R, I266L, and D267Q, or may be found in Table 2 of van der Sloot et al. (cf. above) and may comprise a human TRAIL mutant with the following single amino acid substitution: D269H, or with the following two amino acid substitutions: D269H and E195R or D269H and T214R.

Thus one preferred embodiment is a TRAIL receptor agonist protein as described herein wherein at least one of the soluble domains comprises a mutant of TRAIL or of a receptor binding domain thereof which binds and/or activates TRAILR1 and/or TRAILR2.

Further examples of mutants of TRAIL, which show reduced TRAIL induced receptor aggregation are H168 (S, T, Q), R170 (E, S, T, Q) and H177 (S, T).

One preferred embodiment of a TRAIL receptor agonist protein comprising a mutant of TRAIL or of a receptor binding domain as described herein is a TRAIL receptor agonist protein wherein component (i) comprises at least one amino acid substitution, particularly as indicated below.

Such an amino acid substitution affects at least one of the following amino acid positions of human TRAIL (SEQ ID NO: 1): R130, G160, H168, R170, H177, Y189, R191, Q193, E195, N199, K201, Y213, T214, S215, H264, I266, D267, D269.

Such an amino acid substitution is at least one of the following: R13OE, G16OM, H168 (S, T, Q), R170 (E, S, T, Q), H177 (SJ)1 Y189A, Y189Q, R191K, Q193S, Q193R, E195R, N199V, N199R, K201R, Y213W, T214R, S215D, H264R, I266L, D267Q, D269H, D269R, or D269K.

A preferred TRAIL-R2 selective domain comprises amino acid substitutions Y189Q, R191 K, Q193R, H264R, I266L and D267Q.

A preferred TRAIL-R1 selective domain comprises amino acid substitutions Y189A, Q193S, N199V, K201R, Y213W and S215D.

The single-chain fusion molecule of the present invention comprises three soluble TRAIL domains, namely components (i), (iii) and (v). The stability of a single-chain TRAIL fusion polypeptide against aggregation is enhanced, if the second and/or third soluble TRAIL domain is an N-terminally shortened domain which optionally comprises amino acid sequence mutations. Thus, preferably, both the second and the third soluble TRAIL domain are N-terminally shortened domains which optionally comprise amino acid sequence mutations in the N-terminal regions, preferably within the first five amino acids of the N-terminus of the soluble TRAIL domain. These mutations may comprise replacement of charged, e.g. acidic or basic amino acids, by neutral amino acids, particularly serine or glycine.

In contrast thereto, the selection of the first soluble TRAIL domain is not as critical. Here, a soluble domain having a full-length N-terminal sequence may be used. It should be noted, however, that also the first soluble TRAIL domain may have an N-terminally shortened and optionally mutated sequence.

In a further preferred embodiment of the present invention, the soluble TRAIL domains (i), (iii) and (v) are soluble human TRAIL domains. The first soluble TRAIL domain (i) may be selected from native, shortened and/or mutated sequences. Thus, the first soluble TRAIL domain (i) has an N-terminal sequence which may start between amino acid Glu116 and Val122 of human TRAIL, and wherein Arg121 may be replaced by a neutral amino acid, e.g. by Ser or Gly. The second and third soluble TRAIL domains (iii) and (v) have a shortened N-terminal sequence which preferably starts between amino acid Gln120 and Val122 of human TRAIL and wherein Arg121 may be replaced by another amino acid, e.g. Ser or Gly.

Preferably, the N-terminal sequence of the soluble TRAIL domains (iii) and (v) is selected from:
(a) Arg121-Val122-Ala123 and
(b) (Gly/Ser) 121.

The soluble TRAIL domain preferably ends with amino acid Gly281 of human TRAIL. In certain embodiments, the TRAIL domain may comprise internal mutations as described above.

Components (ii) and (iv) of the TRAIL receptor agonist protein are peptide linker elements located between components (i) and (iii) or (iii) and (v), respectively. The flexible linker elements have a length of 3-8 amino acids, particularly a length of 3, 4, 5, 6, 7, or 8 amino acids. The linker elements are preferably glycine/serine linkers, i.e. peptide linkers substantially consisting of the amino acids glycine and serine. In cases in which the soluble cytokine domain terminates with S or G (C-terminus), e.g. human TRAIL, the linker starts after S or G. In cases in which the soluble cytokine domain starts with S or G (N-terminus), the linker ends before this S or G.

It should be noted that linker (ii) and linker (iv) do not need to be of the same length. In order to decrease potential immunogenicity, it may be preferred to use shorter linkers. In addition it turned out that shorter linkers lead to single chain molecules with reduced tendency to form aggregates. Whereas linkers that are substantially longer than the ones disclosed here may exhibit unfavorable aggregations properties.

If desired, the linker may comprise an asparagine residue which may form a glycosylate site Asn-Xaa-Ser. In certain embodiments, one of the linkers, e.g. linker (ii) or linker (iv) comprises a glycosylation site. In other embodiments, both linkers (iv) comprise glycosylation sites. In order to increase the solubility of the sc TRAIL proteins and/or in order to reduce the potential immunogenicity, it may be preferred that linker (ii) or linker (iv) or both comprise a glycosylation site.

Preferred linker sequences are selected from GSGSGSGS (SEQ ID NO: 3), GSGSGNGS (SEQ ID NO: 2), GGSGSGSG (SEQ ID NO: 4), GGSGSGSG (SEQ ID NO: 5), GGSG (SEQ ID NO: 6), GGSGNGSG (SEQ ID NO: 7), GGNGSGSG (SEQ ID NO: 8), GGNGSG (SEQ ID NO: 9), and GSGS (SEQ ID NO: 23).

According to a most preferred embodiment, the linker sequences are each GSGSGNGS according to SEQ ID NO: 2. Example linker sequences are shown in Table 2.

TABLE 2

Example Linker Sequences

| SEQ ID NO | Sequence |
|---|---|
| 2 | GSGSGNGS |
| 3 | GSGSGSGS |
| 4 | GGSGSGSG |
| 5 | GGSGSG |
| 6 | GGSG |
| 7 | GGSGNGSG |
| 8 | GGNGSGSG |
| 9 | GGNGSG |
| 22 | GSGSGS |
| 23 | GSGS |
| 24 | GSG |

The TRAIL receptor agonist protein additionally comprises an antibody Fc fragment domain which may be located N-terminal to the first TRAIL domain (i) and/or C-terminal to the third TRAIL domain (v). Preferably, the antibody Fc fragment domain comprises or consists of an amino acid sequence as shown in SEQ ID NO: 10. Alternatively, the Fc fragment domain comprises or consists of an amino acid sequence as shown in SEQ ID NO: 17. Example Fc fragment domains are shown in Table 3.

TABLE 3

Example Fc Fragment Domains

| SEQ ID NO | Sequence |
|---|---|
| 10 | PAPELLGGPSVFLFPPKPKDTLMISRTPEVTCVVVDVSHEDPE VKFNWYVDGVEVHNAKTKPREEQYSSTYRVVSVLTVLHQDW LNGKEYKCKVSNKALPAPIEKTISKAKGQPREPQVYTLPPSRE EMTKNQVSLTCLVKGFYPSDIAVEWESNGQPENNYKTTPPVL DSDGSFFLYSKLTVDKSRWQQGNVFSCSVMHEALHNHYTQK SLSLSPGK |
| 17 | PAPPVAGPSVFLFPPKPKDTLMISRTPEVTCVVVDVSHEDPE VKFNWYVDGVEVHNAKTKPREEQYNSTYRVVSVLTVLHQDW LNGKEYKCKVSNKGLPSSIEKTISKAKGQPREPQVYTLPPSRE EMTKNQVSLTCLVKGFYPSDIAVEWESNGQPENNYKTTPPVL DSDGSFFLYSKLTVDKSRWQQGNVFSCSVMHEALHNHYTQK SLSLSPGK |

The total number of glycosites and the individual position of the carbohydrates in three dimensions impacts the in-vivo stability of TRAIL receptor agonist proteins. Further, carbohydrate recognition depends on local density of the terminal saccharides, the branching of the carbohydrate tree and the relative position of the carbohydrates matter.

Depletion of CH2-domain carbohydrates is necessary in order to avoid Fc-receptor based crosslinking in vivo and potential TRAIL-receptor superclustering-based toxicity. Further, partially degraded carbohydrates reduce the in vivo half-life of TRAIL receptor agonist proteins through lectin-driven mechanisms. By reducing the total number of glycosylation sites on the molecule, the resulting compound is less accessible to these mechanisms, increasing half-life. Accordingly, in one embodiment, the overall number of glycosites on the TRAIL receptor agonist proteins of the instant invention was reduced through the depletion of CH2 glycosites, resulting in TRAIL receptor agonist proteins comprising N297S equivalent mutations (according to the EU numbering system) creating aglycosl-CH2 domains.

CH2-glycosites present on the inner surface areas normally shield the subdomain from proteases during "open Fc-conformation transits" wherein hinge-interchain disulfide bonds are reduced and the covalent interchain linkage is disrupted. This enables CH2-dissociation and exposure of the inner surface area towards proteases. TRAIL receptor agonist proteins comprising an N297S equivalent mutation (according to the EU numbering system) creating an aglycosl-CH2 are therefore likely to be less proteolytically stable than equivalent structures with wild-type CH2 glycosylation. This would impact the compound's stability during USP/DSP/storage, where host cell proteases are present and have long-term access to the structure. Accordingly, in certain embodiments, the TRAIL receptor agonist lacks CH2 glycosites, but comprises glycosites in the linker sequences of each polypeptide chain (e.g., GSGSGNGS according to SEQ ID NO: 2). In certain exemplary embodiments, the TRAIL receptor agonist comprises two glycosites per polypeptide chain, for a total of four glycosites, According to a preferred embodiment of the invention, the antibody Fc fragment domain is fused via a hinge-linker element. The hinge-linker element has a length of 10-30 amino acids, particularly a length of 15-25 amino acids, e.g. 22 amino acids. The hinge-linker element preferably comprises the hinge-region sequence of an immunoglobulin, herein referred to as "Ig hinge-region". The term "Ig hinge-region" means any polypeptide comprising an amino acid sequence that shares sequence identity or similarity with a portion of a naturally occurring Ig hinge-region sequence which includes the cysteine residues at which the disulfide bonds link the two heavy chains of the immunoglobulin.

Derivatives and analogues of the hinge-region can be obtained by mutations. A derivative or analogue as referred to herein is a polypeptide comprising an amino acid sequence that shares sequence identity or similarity with the full length sequence of the wild type (or naturally occurring protein) except that it has one or more amino acid sequence differences attributable to a deletion, insertion and/or substitution. According to the present invention, however, the term "hinge-linker" is not limited to those linkers comprising an Ig hinge-region or a derivative thereof, but any linkers long enough to allow the domains attached by the hinge-linker element to attain a biologically active confirmation.

The number of molecules with open Fc-conformation in an individual TRAIL receptor agonist protein depends on the number of interchain-disulfide bonds present in the hinge region. Accordingly, in one embodiment a third cysteine was introduced into the hinge region of the TRAIL receptor agonist proteins of the instant invention in order to ameliorate the effect of depleting the CH2-glycosites.

Further, the TRAIL receptor agonist proteins of the invention additionally comprise mutation of the upper-hinge lysine to a glycine to reduce proteolytic processing at this site.

A particularly preferred hinge-linker element comprises or consists of the amino acid sequence as shown in SEQ ID NO: 11 (Table 4).

The TRAIL receptor agonist protein may additionally comprise an N-terminal signal peptide domain, which allows processing, e.g. extracellular secretion, in a suitable host cell. Preferably, the N-terminal signal peptide domain comprises a protease cleavage site, e.g. a signal peptidase cleavage site and thus may be removed after or during expression to obtain the mature protein. A particularly preferred N-terminal signal peptide domain comprises the amino acid sequence as shown in SEQ ID NO: 12 (Table 4).

Further, the TRAIL receptor agonist protein may additionally comprise a C-terminal element, having a length of e.g. 1-50, preferably 10-30 amino acids which may include or connect to a recognition/purification domain, e.g. a FLAG domain, a Strep-tag or Strep-tag II domain and/or a poly-His domain. According to a particularly preferred embodiment, the fusion polypeptide comprises a Strep-tag fused to the C-terminus via a short serine linker as shown in SEQ ID NO: 13 (Table 4).

An exemplary hinge-linker element, N-terminal signal peptide domain, and short serine linker are shown in Table 4.

TABLE 4

Exemplary domains and linkers

| SEQ ID NO | Sequence |
|---|---|
| 11 | GPGSSSSSSSGSCDKTHTCPPC |
| 12 | METDTLLVFVLLVWVPAGNG |
| 13 | SSSSSSAWSHPQFEK |
| 25 | GPGSSSSSSGSCDKTHTCPPC |

According to a particularly preferred embodiment of the invention, the fusion polypeptide comprises three soluble TRAIL domains fused by peptide linker elements of SEQ ID NO: 2. The first soluble TRAIL domain (i) consists of amino acids 120-281 of human TRAIL according to SEQ ID NO: 1 and the soluble TRAIL domains (iii) and (v) consist of amino acids 121-281 of human TRAIL according to SEQ ID NO: 1. Additionally, the fusion polypeptide comprises an antibody Fc fragment domain according to SEQ ID NO: 10 that is fused C-terminally to the soluble TRAIL domain (v) via a hinge-linker according to SEQ ID NO: 11. The inventors surprisingly found that this particular fusion polypeptide provides improved biological activity and is particularly stable. The amino acid sequence of an exemplary embodiment of a TRAIL receptor agonist protein of the invention is set forth in SEQ ID NO: 19.

Further, the fusion polypeptide may comprise an N-terminal signal peptide domain e.g. according to SEQ ID NO: 12. A specific example of a TRAIL receptor agonist protein of the invention is shown in SEQ ID NO: 14.

According to another preferred embodiment, the fusion polypeptide may additionally comprise a C-terminal Strep-tag that is fused to the polypeptide of the invention via a short serine linker as shown in SEQ ID NO: 13. According to this aspect of the invention, the Fc fragment preferably consists of the amino acid sequence as shown in SEQ ID NO: 10 or 17. Further, the Fc fragment may consist of a shorter Fc fragment, for example including amino acids 1-217 of SEQ ID NO: 10. Particularly preferred examples of fusion polypeptides comprising a C-terminal Strep-tag are shown in SEQ ID NOs: 15 and 18.

The exemplary TRAIL receptor agonist proteins as shown in SEQ ID NOs: 14, 15 and 18 each comprise an N-terminal signal peptide domain. The signal peptide domain includes amino acids 1-20. In each case, the mature protein starts with amino acid 21. Mature exemplary TRAIL receptor agonist proteins of the instant invention are set forth in SEQ ID NO: 19, 20, 21, 26, 27, 28, 29, and 30. Exemplary TRAIL receptor agonist proteins described above are shown in Table 5.

The TRAIL receptor agonist as set forth in SEQ ID NO: 19 has a reduced total number of glycosylation sites (the N297S mutation in the CH2 region providing an aglycosylated CH2 domain), an increased number of inter-chain disulfide bonds in the hinge region, and the mutation of an upper-hinge lysine to a glycine. These alterations provide a decrease in potential degradation and TRAIL receptor superclustering (along with concomitant toxicity) while increasing the half-life of the molecule. In some embodiments, the N-terminal glutamine is modified to pyroglutamate (Liu et al. 2011, J. Biol. Chem. 286:11211-11217).

TABLE 5

Exemplary TRAIL Receptor Agonist Proteins

| SEQ ID NO | Sequence |
|---|---|
| 14 | METDTLLVFVLLVWVPAGNGQRVAAHITGTRGRSNTLSSPNSKNEK ALGRKINSWESSRSGHSFLSNLHLRNGELVIHEKGFYYIYSQTYFRF QEEIKENTKNDKQMVQYIYKYTSYPDPILLMKSARNSCWSKDAEYG LYSIYQGGIFELKENDRIFVSVTNEHLIDMDHEASFFGAFLVGGSGS GNGSRVAAHITGTRGRSNTLSSPNSKNEKALGRKINSWESSRSGH SFLSNLHLRNGELVIHEKGFYYIYSQTYFRFQEEIKENTKNDKQMVQ YIYKYTSYPDPILLMKSARNSCWSKDAEYGLYSIYQGGIFELKENDRI FVSVTNEHLIDMDHEASFFGAFLVGGSGSGNGSRVAAHITGTRGRS NTLSSPNSKNEKALGRKINSWESSRSGHSFLSNLHLRNGELVIHEK GFYYIYSQTYFRFQEEIKENTKNDKQMVQYIYKYTSYPDPILLMKSA RNSCWSKDAEYGLYSIYQGGIFELKENDRIFVSVTNEHLIDMDHEAS FFGAFLVGGPGSSSSSSSGSCDKTHTCPPCPAPELLGGPSVFLFPP KPKDTLMISRTPEVTCVVVDVSHEDPEVKFNWYVDGVEVHNAKTK PREEQYSSTYRVVSVLTVLHQDWLNGKEYKCKVSNKALPAPIEKTI SKAKGQPREPQVYTLPPSREEMTKNQVSLTCLVKGFYPSDIAVEW ESNGQPENNYKTTPPVLDSDGSFFLYSKLTVDKSRWQQGNVFSCS VMHEALHNHYTQKSLSLSPGK |
| 15 | METDTLLVFVLLVWVPAGNGQRVAAHITGTRGRSNTLSSPNSKNEK ALGRKINSWESSRSGHSFLSNLHLRNGELVIHEKGFYYIYSQTYFRF QEEIKENTKNDKQMVQYIYKYTSYPDPILLMKSARNSCWSKDAEYG LYSIYQGGIFELKENDRIFVSVTNEHLIDMDHEASFFGAFLVGGSGS GNGSRVAAHITGTRGRSNTLSSPNSKNEKALGRKINSWESSRSGH SFLSNLHLRNGELVIHEKGFYYIYSQTYFRFQEEIKENTKNDKQMVQ YIYKYTSYPDPILLMKSARNSCWSKDAEYGLYSIYQGGIFELKENDRI FVSVTNEHLIDMDHEASFFGAFLVGGSGSGNGSRVAAHITGTRGRS NTLSSPNSKNEKALGRKINSWESSRSGHSFLSNLHLRNGELVIHEK GFYYIYSQTYFRFQEEIKENTKNDKQMVQYIYKYTSYPDPILLMKSA RNSCWSKDAEYGLYSIYQGGIFELKENDRIFVSVTNEHLIDMDHEAS FFGAFLVGGPGSSSSSSSGSCDKTHTCPPCPAPELLGGPSVFLFPP KPKDTLMISRTPEVTCVVVDVSHEDPEVKFNWYVDGVEVHNAKTK PREEQYSSTYRVVSVLTVLHQDWLNGKEYKCKVSNKALPAPIEKTI SKAKGQPREPQVYTLPPSREEMTKNQVSLTCLVKGFYPSDIAVEW ESNGQPENNYKTTPPVLDSDGSFFLYSKLTVDKSRWQQGNVFSCS VMHEALHNHYTQKSLSLSPGSSSSSAWSHPQFEK |
| 18 | METDTLLVFVLLVWVPAGNGQRVAAHITGTRGRSNTLSSPNSKNEK ALGRKINSWESSRSGHSFLSNLHLRNGELVIHEKGFYYIYSQTYFRF QEEIKENTKNDKQMVQYIYKYTSYPDPILLMKSARNSCWSKDAEYG LYSIYQGGIFELKENDRIFVSVTNEHLIDMDHEASFFGAFLVGGSGS GNGSRVAAHITGTRGRSNTLSSPNSKNEKALGRKINSWESSRSGH SFLSNLHLRNGELVIHEKGFYYIYSQTYFRFQEEIKENTKNDKQMVQ YIYKYTSYPDPILLMKSARNSCWSKDAEYGLYSIYQGGIFELKENDRI FVSVTNEHLIDMDHEASFFGAFLVGGSGSGNGSRVAAHITGTRGRS NTLSSPNSKNEKALGRKINSWESSRSGHSFLSNLHLRNGELVIHEK GFYYIYSQTYFRFQEEIKENTKNDKQMVQYIYKYTSYPDPILLMKSA RNSCWSKDAEYGLYSIYQGGIFELKENDRIFVSVTNEHLIDMDHEAS FFGAFLVGGPGSSSSSSSGSCDKTHTCPPCPAPPVAGPSVFLFPP |

TABLE 5-continued

Exemplary TRAIL Receptor Agonist Proteins

| SEQ ID NO | Sequence |
|---|---|
|  | KPKDTLMISRTPEVTCVVVDVSHEDPEVKFNWYVDGVEVHNAKTK PREEQYNSTYRVVSVLTVLHQDWLNGKEYKCKVSNKGLPSSIEKTI SKAKGQPREPQVYTLPPSREEMTKNQVSLTCLVKGFYPSDIAVEW ESNGQPENNYKTTPPVLDSDGSFFLYSKLTVDKSRWQQGNVFSCS VMHEALHNHYTQKSLSLSPGK |
| 19 | QRVAAHITGTRGRSNTLSSPNSKNEKALGRKINSWESSRSGHSFLS NLHLRNGELVIHEKGFYYIYSQTYFRFQEEIKENTKNDKQMVQYIYK YTSYPDPILLMKSARNSCWSKDAEYGLYSIYQGGIFELKENDRIFVS VTNEHLIDMDHEASFFGAFLVGGSGSGNGSRVAAHITGTRGRSNTL SSPNSKNEKALGRKINSWESSRSGHSFLSNLHLRNGELVIHEKGFY YIYSQTYFRFQEEIKENTKNDKQMVQYIYKYTSYPDPILLMKSARNS CWSKDAEYGLYSIYQGGIFELKENDRIFVSVTNEHLIDMDHEASFFG AFLVGGSGSGNGSRVAAHITGTRGRSNTLSSPNSKNEKALGRKINS WESSRSGHSFLSNLHLRNGELVIHEKGFYYIYSQTYFRFQEEIKENT KNDKQMVQYIYKYTSYPDPILLMKSARNSCWSKDAEYGLYSIYQGG IFELKENDRIFVSVTNEHLIDMDHEASFFGAFLVGGPGSSSSSSGS CDKTHTCPPCPAPELLGGPSVFLFPPKPKDTLMISRTPEVTCVVVD VSHEDPEVKFNWYVDGVEVHNAKTKPREEQYSSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSD GSFFLYSKLTVDKSRWQQGNVFSCSVMHEALHNHYTQKSLSLSPG K |
| 20 | QRVAAHITGTRGRSNTLSSPNSKNEKALGRKINSWESSRSGHSFLS NLHLRNGELVIHEKGFYYIYSQTYFRFQEEIKENTKNDKQMVQYIYK YTSYPDPILLMKSARNSCWSKDAEYGLYSIYQGGIFELKENDRIFVS VTNEHLIDMDHEASFFGAFLVGGSGSGNGSRVAAHITGTRGRSNTL SSPNSKNEKALGRKINSWESSRSGHSFLSNLHLRNGELVIHEKGFY YIYSQTYFRFQEEIKENTKNDKQMVQYIYKYTSYPDPILLMKSARNS CWSKDAEYGLYSIYQGGIFELKENDRIFVSVTNEHLIDMDHEASFFG AFLVGGSGSGNGSRVAAHITGTRGRSNTLSSPNSKNEKALGRKINS WESSRSGHSFLSNLHLRNGELVIHEKGFYYIYSQTYFRFQEEIKENT KNDKQMVQYIYKYTSYPDPILLMKSARNSCWSKDAEYGLYSIYQGG IFELKENDRIFVSVTNEHLIDMDHEASFFGAFLVGGPGSSSSSSGS CDKTHTCPPCPAPELLGGPSVFLFPPKPKDTLMISRTPEVTCVVVD VSHEDPEVKFNWYVDGVEVHNAKTKPREEQYSSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSD GSFFLYSKLTVDKSRWQQGNVFSCSVMHEALHNHYTQKSLSLSPG SSSSSSAWSHPQFEK |
| 21 | QRVAAHITGTRGRSNTLSSPNSKNEKALGRKINSWESSRSGHSFLS NLHLRNGELVIHEKGFYYIYSQTYFRFQEEIKENTKNDKQMVQYIYK YTSYPDPILLMKSARNSCWSKDAEYGLYSIYQGGIFELKENDRIFVS VTNEHLIDMDHEASFFGAFLVGGSGSGNGSRVAAHITGTRGRSNTL SSPNSKNEKALGRKINSWESSRSGHSFLSNLHLRNGELVIHEKGFY YIYSQTYFRFQEEIKENTKNDKQMVQYIYKYTSYPDPILLMKSARNS CWSKDAEYGLYSIYQGGIFELKENDRIFVSVTNEHLIDMDHEASFFG AFLVGGSGSGNGSRVAAHITGTRGRSNTLSSPNSKNEKALGRKINS WESSRSGHSFLSNLHLRNGELVIHEKGFYYIYSQTYFRFQEEIKENT KNDKQMVQYIYKYTSYPDPILLMKSARNSCWSKDAEYGLYSIYQGG IFELKENDRIFVSVTNEHLIDMDHEASFFGAFLVGGPGSSSSSSGS CDKTHTCPPCPAPPVAGPSVFLFPPKPKDTLMISRTPEVTCVVVDV SHEDPEVKFNWYVDGVEVHNAKTKPREEQYNSTYRVVSVLTVLHQ DWLNGKEYKCKVSNKGLPSSIEKTISKAKGQPREPQVYTLPPSREE MTKNQVSLTCLVKGFYPSDIAVEWESNGQPENNYKTTPPVLDSDG SFFLYSKLTVDKSRWQQGNVFSCSVMHEALHNHYTQKSLSLSPGK |
| 26 | QRVAAHITGTRGRSNTLSSPNSKNEKALGRKINSWESSRSGHSFLS NLHLRNGELVIHEKGFYYIYSQTYFRFQEEIKENTKNDKQMVQYIYK YTSYPDPILLMKSARNSCWSKDAEYGLYSIYQGGIFELKENDRIFVS VTNEHLIDMDHEASFFGAFLVGGSGSGNGSRVAAHITGTRGRSNTL SSPNSKNEKALGRKINSWESSRSGHSFLSNLHLRNGELVIHEKGFY YIYSQTYFRFQEEIKENTKNDKQMVQYIYKYTSYPDPILLMKSARNS CWSKDAEYGLYSIYQGGIFELKENDRIFVSVTNEHLIDMDHEASFFG AFLVGGSGSGNGSRVAAHITGTRGRSNTLSSPNSKNEKALGRKINS WESSRSGHSFLSNLHLRNGELVIHEKGFYYIYSQTYFRFQEEIKENT KNDKQMVQYIYKYTSYPDPILLMKSARNSCWSKDAEYGLYSIYQGG IFELKENDRIFVSVTNEHLIDMDHEASFFGAFLVGGPGSSSSSSGSD KTHTCPPCPAPPVAGPSVFLFPPKPKDTLMISRTPEVTCVVVDVSH EDPEVKFNWYVDGVEVHNAKTKPREEQYNSTYRVVSVLTVLHQD WLNGKEYKCKVSNKGLPSSIEKTISKAKGQPREPQVYTLPPSREEM TKNQVSLTCLVKGFYPSDIAVEWESNGQPENNYKTTPPVLDSDGSF FLYSKLTVDKSRWQQGNVFSCSVMHEALHNHYTQKSLSLSPGSSS SSSSAWSHPQFEK |
| 27 | QRVAAHITGTRGRSNTLSSPNSKNEKALGRKINSWESSRSGHSFLS NLHLRNGELVIHEKGFYYIYSQTYFRFQEEIKENTKNDKQMVQYIYK YTSYPDPILLMKSARNSCWSKDAEYGLYSIYQGGIFELKENDRIFVS VTNEHLIDMDHEASFFGAFLVGGSGSGNGSRVAAHITGTRGRSNTL SSPNSKNEKALGRKINSWESSRSGHSFLSNLHLRNGELVIHEKGFY YIYSQTYFRFQEEIKENTKNDKQMVQYIYKYTSYPDPILLMKSARNS CWSKDAEYGLYSIYQGGIFELKENDRIFVSVTNEHLIDMDHEASFFG AFLVGGSGSGNGSRVAAHITGTRGRSNTLSSPNSKNEKALGRKINS WESSRSGHSFLSNLHLRNGELVIHEKGFYYIYSQTYFRFQEEIKENT KNDKQMVQYIYKYTSYPDPILLMKSARNSCWSKDAEYGLYSIYQGG IFELKENDRIFVSVTNEHLIDMDHEASFFGAFLVGGPGSSSSSSGSCDKT HTCPPCPAPELLGGPSVFLFPPKPKDTLMISRTPEVTCVVVDVSHE DPEVKFNWYVDGVEVHNAKTKPREEQYSSTYRVVSVLTVLHQDWL NGKEYKCKVSNKALPAPIEKTISKAKGQPREPQVYTLPPSREEMTK NQVSLTCLVKGFYPSDIAVEWESNGQPENNYKTTPPVLDSDGSFFL YSKLTVDKSRWQQGNVFSCSVMHEALHNHYTQKSLSLSPGSSSSS SAWSHPQFEK |
| 28 | QRVAAHITGTRGRSNTLSSPNSKNEKALGRKINSWESSRSGHSFLS NLHLRNGELVIHEKGFYYIYSQTYFRFQEEIKENTKNDKQMVQYIYK YTSYPDPILLMKSARNSCWSKDAEYGLYSIYQGGIFELKENDRIFVS VTNEHLIDMDHEASFFGAFLVGGSGSGRVAAHITGTRGRSNTLSS PNSKNEKALGRKINSWESSRSGHSFLSNLHLRNGELVIHEKGFYYIY SQTYFRFQEEIKENTKNDKQMVQYIYKYTSYPDPILLMKSARNSCW SKDAEYGLYSIYQGGIFELKENDRIFVSVTNEHLIDMDHEASFFGAFL VGGSGSGRVAAHITGTRGRSNTLSSPNSKNEKALGRKINSWESS RSGHSFLSNLHLRNGELVIHEKGFYYIYSQTYFRFQEEIKENTKNDK QMVQYIYKYTSYPDPILLMKSARNSCWSKDAEYGLYSIYQGGIFELK ENDRIFVSVTNEHLIDMDHEASFFGAFLVGGPGSSSSSSGSCDKT HTCPPCPAPELLGGPSVFLFPPKPKDTLMISRTPEVTCVVVDVSHE DPEVKFNWYVDGVEVHNAKTKPREEQYSSTYRVVSVLTVLHQDWL NGKEYKCKVSNKALPAPIEKTISKAKGQPREPQVYTLPPSREEMTK NQVSLTCLVKGFYPSDIAVEWESNGQPENNYKTTPPVLDSDGSFFL YSKLTVDKSRWQQGNVFSCSVMHEALHNHYTQKSLSLSPGSSSSS SAWSHPQFEK |
| 29 | QRVAAHITGTRGRSNTLSSPNSKNEKALGRKINSWESSRSGHSFLS NLHLRNGELVIHEKGFYYIYSQTYFRFQEEIKENTKNDKQMVQYIYK YTSYPDPILLMKSARNSCWSKDAEYGLYSIYQGGIFELKENDRIFVS VTNEHLIDMDHEASFFGAFLVGGSGSGNGSRVAAHITGTRGRSNTL SSPNSKNEKALGRKINSWESSRSGHSFLSNLHLRNGELVIHEKGFY YIYSQTYFRFQEEIKENTKNDKQMVQYIYKYTSYPDPILLMKSARNS CWSKDAEYGLYSIYQGGIFELKENDRIFVSVTNEHLIDMDHEASFFG AFLVGGSGSRVAAHITGTRGRSNTLSSPNSKNEKALGRKINSWESS RSGHSFLSNLHLRNGELVIHEKGFYYIYSQTYFRFQEEIKENTKNDK QMVQYIYKYTSYPDPILLMKSARNSCWSKDAEYGLYSIYQGGIFELK ENDRIFVSVTNEHLIDMDHEASFFGAFLVGGPGSSSSSSGSCDKT HTCPPCPAPELLGGPSVFLFPPKPKDTLMISRTPEVTCVVVDVSHE DPEVKFNWYVDGVEVHNAKTKPREEQYSSTYRVVSVLTVLHQDWL NGKEYKCKVSNKALPAPIEKTISKAKGQPREPQVYTLPPSREEMTK NQVSLTCLVKGFYPSDIAVEWESNGQPENNYKTTPPVLDSDGSFFL YSKLTVDKSRWQQGNVFSCSVMHEALHNHYTQKSLSLSPGK |
| 30 | QRVAAHITGTRGRSNTLSSPNSKNEKALGRKINSWESSRSGHSFLS NLHLRNGELVIHEKGFYYIYSQTYFRFQEEIKENTKNDKQMVQYIYK YTSYPDPILLMKSARNSCWSKDAEYGLYSIYQGGIFELKENDRIFVS VTNEHLIDMDHEASFFGAFLVGGSGSGRVAAHITGTRGRSNTLSS PNSKNEKALGRKINSWESSRSGHSFLSNLHLRNGELVIHEKGFYYIY SQTYFRFQEEIKENTKNDKQMVQYIYKYTSYPDPILLMKSARNSCW SKDAEYGLYSIYQGGIFELKENDRIFVSVTNEHLIDMDHEASFFGAFL VGGSGSGRVAAHITGTRGRSNTLSSPNSKNEKALGRKINSWESS RSGHSFLSNLHLRNGELVIHEKGFYYIYSQTYFRFQEEIKENTKNDK QMVQYIYKYTSYPDPILLMKSARNSCWSKDAEYGLYSIYQGGIFELK ENDRIFVSVTNEHLIDMDHEASFFGAFLVGGPGSSSSSSGSCDKT HTCPPCPAPELLGGPSVFLFPPKPKDTLMISRTPEVTCVVVDVSHE DPEVKFNWYVDGVEVHNAKTKPREEQYSSTYRVVSVLTVLHQDWL NGKEYKCKVSNKALPAPIEKTISKAKGQPREPQVYTLPPSREEMTK NQVSLTCLVKGFYPSDIAVEWESNGQPENNYKTTPPVLDSDGSFFL YSKLTVDKSRWQQGNVFSCSVMHEALHNHYTQKSLSLSPGK |

A further aspect of the present invention relates to a nucleic acid molecule encoding a TRAIL receptor agonist protein as described herein. The nucleic acid molecule may be a DNA molecule, e.g. a double-stranded or single-stranded DNA molecule, or an RNA molecule. The nucleic acid molecule may encode the TRAIL receptor agonist protein or a precursor thereof, e.g. a pro- or pre-proform of the TRAIL receptor agonist protein which may comprise a signal sequence or other heterologous amino acid portions for secretion or purification which are preferably located at the N- and/or C-terminus of the TRAIL receptor agonist protein. The heterologous amino acid portions may be linked to the first and/or second domain via a protease cleavage site, e.g. a Factor X3, thrombin or IgA protease cleavage site. A specific example of a nucleic acid sequence of the invention is shown in Table 6 as SEQ ID NO: 16. This nucleic acid molecule encodes the fusion polypeptide of SEQ ID NO: 14.

Harbor Press, and Ausubel et al. (1989), Current Protocols in Molecular Biology, John Wiley & Sons or more recent editions thereof.

Various expression vector/host cell systems may be used to express the nucleic acid sequences encoding the TRAIL receptor agonist proteins of the present invention. Suitable host cells include, but are not limited to, prokaryotic cells such as bacteria, e.g. *E.coli*, eukaryotic host cells such as yeast cells, insect cells, plant cells or animal cells, preferably mammalian cells and, more preferably, human cells. Further, the invention relates to a non-human organism transformed or transfected with a nucleic acid molecule as described above. Such transgenic organisms may be generated by known methods of genetic transfer including homologous recombination.

A further aspect of the present invention relates to a pharmaceutical or diagnostic composition comprising as the active agent at least one TRAIL receptor agonist protein, a

TABLE 6

Nucleic Acid Sequence of Exemplary TRAIL Receptor Agonist Protein

| SEQ ID NO | Sequence |
|---|---|
| 16 | gatatcggtaccgccaccatggaaaccgacaccctgctggtgttcgtgctgctcgtgtgggtgcc agccggcaatggacagagagtggccgctcatatcaccggcaccggggcagatctaacacc ctgtccagccccaactccaagaacgagaaggccctgggccggaagatcaactcctgggagt cctccagatccggccactcctttctgtccaacctgcacctgagaaacggcgagctggtcatcca cgagaagggcttcactacatctactcccagacctacttcaggtttcaggaagagatcaaagag aacacaaagaacgacaagcagatggtgcagtatatctacaagtacacctcctaccccgaccc catcctgctgatgaagtccgcccggaactcctgctggtccaaggatgctgagtacggcctgtac agcatctaccagggcggcatcttcgagctgaaagagaacgaccggatcttcgtgtccgtgacc aacgagcacctgatcgacatggaccacgaggccagcttttcggcgcctttctcgtgggcggat ccggaagcggaaacggcagtagagtggctgcccacattaccggaaccagaggccggtcca acacctgagcagcccaacagcaaaaatgagaaagctctcggcgcaagatcaacagct gggaatctagcagaagcggccacagctttctgagcaatctgcatctgcggaacggcgaactc gtgattcatgagaagggtttttattatatctatagccagacatactttcgattccaggaggaaatca aggaaaacaccaaaaatgataaacagatggtccagtacatttataagtataccagctaccctg atcctatcctcctcatgaagtctgccagaaactcttgttggagcaaggacgccgagtatggactg tactctatctatcaggggggatctttgaactcaaagaaaacgatcgcatctttgtcagcgtcacc aatgagcatctcattgatatggatcatgaagctagtttcttcggggcattcctcgtgggaggctccg gctctggcaacggatctagagtcgccgcacacatcacagggaccagaggcagaagcaata ccctgtcctcccaaatagtaaaaacgaaaaggcactcggccgcaaaattaattcctgggag agcagcagatccgggcacagtttttctgtctaatctccatctgaggaatggggagctggtgattca cgaaaaaggattttactacattttacagtcagacttactttcgttttcaggaagagattaaggaaaat accaaaaacgacaagcagatggtccagtacatctataaatacacctcttatcctgacccaattct gctcatgaagagtgcccgcaacagctgctggtctaaagacgccgaatacgggctgtattccatt taccaggggggaatttttgagctgaaggaaaatgatcggattttttgtctctgtcacaaacgaaca cctcatcgatatggatcacgaagcctctttctttggcgccttcctggtcggaggccctggctcgagt tccagctcctcttctggctcctgcgacaagacccacacctgtccccttgtcctgccccctgaactg ctgggcggaccttccgtgttcctgttccccccaaagcccaaggacaccctgatgatctcccgga ccccgaagtgacctgcgtggtggtggatgtgtctcacgaggaccctgaagtgaagttcaattg gtacgtggacggcgtggaagtgcacaacgccaagaccaagcccagagaggaacagtactc ctccacctaccgggtggtgtctgtgctgaccgtgctgcaccaggactggctgaacggcaaaga gtacaagtgcaaggtgtccaacaaggccctgcctgccccatcgaaaagaccatctccaagg ccaagggccagccccgggaacccaggtgtacacactgcccctagccgggaagagatga ccaagaaccaggtgtccctgacctgcctggtcaagggcttttacccctccgacattgccgtgga atgggagtccaacggccagcctgagaacaactacaagaccacccccctgtgctggactcc gacggctcattcttcctgtactccaagctgacagtggacaagtcccggtggcagcagggcaac gtgttctcctgctccgtgatgcacgaggccctgcacaaccactacacccagaagtccctgtccct gagccccggcaaatgatagaagcttgatatc |

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosomal integration vector, etc. Examples of suitable expression control sequences and vectors are described for example by Sambrook et al. (1989) Molecular Cloning, A Laboratory Manual, Cold Spring respective nucleic acid encoding therefore, or a transformed or transfected cell, all as described herein.

The term "TRAIL-associated disease or disorder" as used herein is any disease or disorder which may be ameliorated by addition of a TRAIL receptor agonist. At least one TRAIL receptor agonist protein, respective nucleic acid encoding therefore, or transformed or transfected cell, all as described herein may be used in therapy, e.g., in the prophylaxis and/or treatment of disorders caused by, associated with and/or accompanied by dysfunction of TRAIL, particularly proliferative disorders, such as tumors, e.g. solid or lymphatic tumors; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

The term "dysfunction of TRAIL" as used herein is to be understood as any function or expression of TRAIL that deviates from the normal function or expression of TRAIL, e.g., overexpression of the TRAIL gene or protein, reduced or abolished expression of the TRAIL gene or protein compared to the normal physiological expression level of TRAIL, increased activity of TRAIL, reduced or abolished activity of TRAIL, increased binding of TRAIL to any binding partners, e.g., to a receptor, particularly a TRAIL receptor or another cytokine molecule, reduced or abolished binding to any binding partner, e.g. to a receptor, particularly a TRAIL receptor or another cytokine molecule, compared to the normal physiological activity or binding of TRAIL.

In various embodiments, a method is provided for diagnosing and/or treating a human subject suffering from a disorder which can be diagnosed and/or treated by targeting TRAIL receptors comprising administering to the human subject a TRAIL receptor agonist protein disclosed herein such that the effect on the activity of the target, or targets, in the human subject is agonistic, one or more symptoms is alleviated, and/or treatment is achieved. The TRAIL receptor agonist proteins provided herein can be used to diagnose and/or treat humans suffering from primary and metastatic cancers, including carcinomas of breast, colon, rectum, lung (e.g., small cell lung cancer "SCLC" and non-small cell lung cancer "NSCLC"), oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), tumors arising from hematopoietic malignancies, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), hairy cell leukemia, Hodgkin's and non-Hodgkin's lymphomas, DLBCL, follicular lymphomas, hematopoietic malignancies, Kaposi's sarcoma, malignant lymphoma, malignant histiocytosis, malignant melanoma, multiple myeloma, paraneoplastic syndrome/hypercalcemia of malignancy, or solid tumors.

A pharmaceutical composition comprising a TRAIL receptor agonist protein disclosed herein and a pharmaceutically acceptable carrier is provided. In some embodiments, the pharmaceutical composition comprises at least one additional therapeutic agent for treating a disorder. For example, the additional agent may be a therapeutic agent, a chemotherapeutic agent; an imaging agent, a cytotoxic agent, an angiogenesis inhibitor, a kinase inhibitor (including but not limited to a KDR and a TIE-2 inhibitor), a co-stimulation molecule modulator or an immune checkpoint inhibitor (including but not limited to anti-B7.1, anti-B7.2, anti-B7.3, anti-B7.4, anti-CD28, anti-B7RP1, CTLA4-Ig, anti-CTLA-4, anti-PD-1, anti-PD-L1, anti-PD-L2, anti-ICOS, anti-LAG-3, anti-Tim3, anti-VISTA, anti-HVEM, anti-BTLA, LIGHT fusion protein, anti-CD137, anti-CD137L, anti-OX40, anti-OX40L, anti-CD70, anti-CD27, anti-GAL9, anti-A2AR, anti-KIR, anti-IDO-1, anti-CD20), a dendritic cell/antigen-presenting cell modulator (including but not limited to anti-CD40 antibody, anti-CD40 L, anti-DC-SIGN, anti-Dectin-1, anti-CD301, anti-CD303, anti-CD123, anti-CD207, anti-DNGR1, anti-CD205, anti-DCIR, anti-CD206, anti-ILT7), a modulator for Toll-like receptors (including but not limited to anti-TLR-1, anti-TLR-2, anti-TLR-3, anti-TLR-4, anti-TLR-4, anti-TLR-5, anti-TLR-6, anti-TLR-7, anti-TLR-8, anti-TLR-9), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, or an anti-IL-6/cytokine receptor antibody), a bispecific redirected T cell or NK cell cytotoxicity (including but not limited to a BiTE®), a chimeric T cell receptor (CAR-T) based therapy, a T cell receptor (TCR)-based therapy, a therapeutic cancer vaccine, methotrexate, cyclosporin, rapamycin, FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

In an embodiment, a method of treating a cancer or in the prevention or inhibition of metastases from the tumors described herein, the TRAIL receptor agonist protein(s) can be used alone or in combination with one or more additional agents, e.g., a chemotherapeutic, radiotherapy, or biological agent. In some embodiments, the agent can include the following: 13-cis-Retinoic Acid; 2-CdA; 2-Chlorodeoxyadenosine; 5-Azacitidine; 5-Fluorouracil; 5-FU; 6-Mercaptopurine; 6-MP; 6-TG; 6-Thioguanine; Abraxane; Accutane®; Actinomycin-D; Adriamycin®; Adrucil®; Afinitor®; Agrylin®; Ala-Cort®; Aldesleukin; Alemtuzumab; ALIMTA; Alitretinoin; Alkaban-AQ®; Alkeran®; All-transretinoic Acid; Alpha Interferon; Altretamine; Amethopterin; Amifostine; Aminoglutethimide; Anagrelide; Anandron®; Anastrozole; Arabinosylcytosine; Ara-C Aranesp®; Aredia®; Arimidex®; Aromasin®; Arranon®; Arsenic Trioxide; Arzerra™; Asparaginase; ATRA; Avastin®; Azacitidine; BCG; BCNU; Bendamustine; Bevacizumab; Bexarotene; BEXXAR®; Bicalutamide; BiCNU; Blenoxane®; Bleomycin; Bortezomib; Busulfan; Busulfex®; C225; Calcium Leucovorin; Campath®; Camptosar®; Camptothecin-11; Capecitabine Carac™; Carboplatin; Carmustine; Carmustine Wafer; Casodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®; Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™; Dexamethasone; Dexamethasone Acetate; Dexamethasone Sodium Phosphate; Dexasone; Dexrazoxane; DHAD; DIC; Diodex; Docetaxel; Doxil®; Doxorubicin; Doxorubicin Liposomal; Droxia™;

DTIC; DTIC-Dome®; Duralone®; Duvelisib; Efudex®; Eligard™; Ellence™; Eloxatin™; Elspar®; Emcyt®; Epirubicin; Epoetin Alfa; Erbitux; Erlotinib; Erwinia L-asparaginase; Estramustine; Ethyol Etopophos®; Etoposide; Etoposide Phosphate; Eulexin®; Everolimus; Evista®; Exemestane; Fareston®; Faslodex®; Femara®; Filgrastim; Floxuridine; Fludara®; Fludarabine; Fluoroplex®; Fluorouracil; Fluorouracil (cream); Fluoxymesterone; Flutamide; Folinic Acid; FUDR®; Fulvestrant; Gefitinib; Gemcitabine; Gemtuzumab ozogamicin; Gemzar; Gleevec™; Gliadel® Wafer; GM-CSF; Goserelin; Granulocyte-Colony Stimulating Factor (G-CSF); Granulocyte Macrophage Colony Stimulating Factor (G-MCSF); Halotestin®; Herceptin®; Hexadrol; Hexalen®; Hexamethylmelamine; HMM; Hycamtin®; Hydrea®; Hydrocort Acetate®; Hydrocortisone; Hydrocortisone Sodium Phosphate; Hydrocortisone Sodium Succinate; Hydrocortone Phosphate; Hydroxyurea; Ibrutinib; Ibritumomab; Ibritumomab Tiuxetan; Idamycin®; Idarubicin Ifex®; Interferon-alpha; Interferon-alpha-2b (PEG Conjugate); Ifosfamide; Interleukin-11 (IL-11); Interleukin-2 (IL-2); Imatinib mesylate; Imidazole Carboxamide; Intron A®; ipilimumab, Iressa®; Irinotecan; Isotretinoin; Ixabepilone; Ixempra™; KADCYCLA®; Kidrolase (t) Lanacort®; Lapatinib; L-asparaginase; LCR; Lenalidomide; Letrozole; Leucovorin; Leukeran; Leukine™; Leuprolide; Leurocristine; Leustatin™; Lirilumab; Liposomal Ara-C; Liquid Pred®; Lomustine; L-PAM; L-Sarcolysin; Lupron®; Lupron Depot®; Matulane®; Maxidex; Mechlorethamine; Mechlorethamine Hydrochloride; Medralone®; Medrol®; Megace®; Megestrol; Megestrol Acetate; MEK inhibitors; Melphalan; Mercaptopurine; Mesna; Mesnex™; Methotrexate; Methotrexate Sodium; Methylprednisolone; Meticorten®; Mitomycin; Mitomycin-C; Mitoxantrone M-Prednisol®; MTC; MTX; Mustargen®; Mustine; Mutamycin®; Myleran®; Mylocel™; Mylotarg®; Navitoclax; Navelbine®; Nelarabine; Neosar®; Neulasta™; Neumega®; Neupogen®; Nexavar®; Nilandron®; Nilotinib; Nilutamide; Nipent®; Nitrogen Mustard Novaldex®; Nivolumab; Novantrone®; Nplate; Octreotide; Octreotide acetate; Ofatumumab; Oncospar®; Oncovin®; Ontak®; Onxal™; Oprelvekin; Orapred®; Orasone®; Oxaliplatin; Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™; PEG-L-asparaginase; PEMETREXED; Pembrolizumab; Pentostatin; Pertuzumab; Phenylalanine Mustard; Pidilizumab; Platinol®; Platinol-AQ®; Prednisolone; Prednisone; Prelone®; Procarbazine; PROCRIT®; Proleukin®; Prolifeprospan 20 with Carmustine Implant; Purinethol®; BRAF inhibitors; Raloxifene; Revlimid®; Rheumatrex®; Rituxan®; Rituximab; Roferon-A®; Romiplostim; Rubex®; Rubidomycin hydrochloride; Sandostatin®; Sandostatin LAR®; Sargramostim; Solu-Cortef®; Solu-Medrol®; Sorafenib; SPRYCEL™; STI-571; STIVAGRA™, Streptozocin; SU11248; Sunitinib; Sutent®; Tamoxifen Tarceva®; Targretin®; Tasigna®; Taxol®; Taxotere®; Temodar®; Temozolomide Temsirolimus; Teniposide; TESPA; Thalidomide; Thalomid®; TheraCys®; Thioguanine; Thioguanine Tabloid®; Thiophosphoamide; Thioplex®; Thiotepa; TICE®; Toposar®; Topotecan; Toremifene; Torisel®; Tositumomab; Trastuzumab; Treanda®; Tremelimumab; Tretinoin; Trexall™; Trisenox®; TSPA; TYKERB®; Urelumab; VCR; Vectibix™; Velban®; Velcade®; Venetoclax; VePesid®; Vesanoid®; Viadur™; Vidaza®; Vinblastine; Vinblastine Sulfate; Vincasar Pfs®; Vincristine; Vinorelbine; Vinorelbine tartrate; VLB; VM-26; Vorinostat; Votrient; VP-16; Vumon®; Xeloda®; Zanosar®; Zevalin™, Zinecard®; Zoladex®; Zoledronic acid; Zolinza; or Zometa®, and/or any other agent not specifically listed here that target similar pathways.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more than one, or all of the substances or principles to be administered, while still achieving the desired therapeutic action. This may, e.g., be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In various embodiments, pharmaceutical compositions comprising one or more TRAIL receptor agonist proteins, either alone or in combination with prophylactic agents, therapeutic agents, and/or pharmaceutically acceptable carriers are provided herein. In various embodiments, nonlimiting examples of the uses of the pharmaceutical compositions disclosed herein include diagnosing, detecting, and/or monitoring a disorder, preventing, treating, managing, and/or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (U.S. Patent Publication No. 20090311253 A1).

In various embodiments, a pharmaceutical formulation can comprise one or more amino acid, one or more polysaccharide and/or polysorbate, and a TRAIL receptor agonist protein present at a concentration of between about 0.1 and 100 mg/ml, inclusive of endpoints (e.g., 0.1-10, 1-10, 0.01-50, 1-50, 1-100, 10-100, 25-100, 25-50, or 50-100 mg/ml), where the formulation is at a pH between about 5.0 and 7.0, inclusive of endpoints (e.g., a pH of about 5.0-6.0, 5.5-6.0, 5.0-6.5, 5.5-6.5, or 6.0-7.0). In an embodiment, at least one amino acid in the formulation is histidine and is present at a concentration of about 10-20 mM, 10-15 mM, 15-20 mM, or about 15 mM. In an embodiment, at least one polysaccharide in the formulation is sucrose and is present at a concentration of about 0-8.0% weight/volume (w/v). In an embodiment, the polysorbate in the formulation is polysorbate 80 and is at a concentration of about 0-0.06% w/v. In an embodiment, at least one amino acid in the formulation is arginine and is present at a concentration of about 0-1.5% w/v (e.g., 0.5-1.5, 1.0-1.5, or 0.5-1.0 w/v). In an embodiment, the TRAIL receptor agonist protein is present in the formulation at a concentration of about 0.1-100 mg/ml, (e.g., about 1-100 mg/ml, or about 1-15 mg/ml, or about 1-7.5 mg/ml, or about 2.5-7.5 mg/ml, or about 5-7.5 mg/ml, or about 25-100 mg/ml, or about 20-60 mg/ml, or about 25-50 mg/ml, or about 25 mg/ml, or about 50 mg/ml, or about 0.1-60 mg/ml, or about 0.1-25 mg/ml, or about 1.0-60 mg/ml, or about 0.5-60 mg/ml, or about 0.1-2.0 mg/ml, or about 0.5-2.0 mg/ml, or about 1-5 mg/ml, or about 1-7.5 mg/ml, or about 1-15 mg/ml, or about 0.5 mg/ml, or about 1.0 mg/m).

As used herein, the phrase "effective amount" means an amount of TRAIL agonist protein that results in a detectable improvement (e.g., at least about 5%, 10%, 15%, 20%, 25%, 30%, 35%, 40%, 45%, 50%, 55%, 60%, 65%, 70%, 75%, or more from baseline) in one or more parameters associated with a dysfunction of TRAIL or with a TRAIL-associated disease or disorder.

In various embodiments, the pharmaceutical formulation is an aqueous formulation, a lyophilized formulation, or a lyophilized and rehydrated formulation. In an embodiment, the hydrating solution is dextrose and/or saline (e.g., dextrose at a concentration of about 5% w/v and/or the saline at a concentration of about 0.9% w/v). In an embodiment, the pharmaceutical formulation comprises about 15 mM histidine, about 0.03% (w/v) polysorbate 80, about 4% (w/v) sucrose, and about 0.1-25 mg/ml of the TRAIL receptor agonist protein, or about 1-15 mg/ml of TRAIL receptor agonist protein, and is at a pH of about 6. In an embodiment, the formulation further comprises at least one additional agent.

In various embodiments, a formulation is used containing about 25 mg/ml TRAIL receptor agonist protein, about 15 mM histidine, 0.03% polysorbate 80 (weight/volume, w/v), 4.0% sucrose (w/v), and a pH of about 6.0. In some embodiments, the formulation does not comprise arginine. In some embodiments, the formulation exhibits unexpectedly improved freeze-thaw stability, liquid formulation stability, and/or lyophilized formulation stability, as compared to other formulations comprising other components or concentrations.

Methods of administering a therapeutic agent provided herein include, but are not limited to, oral administration, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (U.S. Patent Publication No. 20090311253 A1).

In various embodiments, dosage regimens may be adjusted to provide for an optimum desired response (e.g., a therapeutic or prophylactic response). For example, a single bolus may be administered, several divided doses may be administered over time or the dose may be proportionally reduced or increased as indicated by the exigencies of the therapeutic situation. In some embodiments, parenteral compositions are formulated in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier.

An exemplary, non-limiting range for a therapeutically or prophylactically effective amount of a TRAIL receptor agonist protein provided herein is about 0.1-100 mg/kg, (e.g., about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, or 10-100 mg/kg, or any concentration in between). In some embodiments, the TRAIL receptor agonist protein is present in a pharmaceutical composition at a therapeutically effective concentration, e.g., a concentration of about 0.1-100 mg/ml (e.g., about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml, or any concentration in between). Note that dosage values may vary with the type and/or severity of the condition to be alleviated. It is to be further understood that for any particular subject, specific dosage regimens may be adjusted over time according to the individual need and/or the professional judgment of the person administering or supervising the administration of the compositions, and that dosage ranges set forth herein are exemplary only and are not intended to limit the scope or practice of the claimed composition.

EXAMPLES

1. Manufacture of a TRAIL Receptor Agonist Protein (sc TRAIL wt)

1.1 Polypeptide Structure

A) Amino acids Met1-Gly20

Ig-Kappa-signal peptide, assumed signal peptidase cleavage site after amino acid Gly20.

B) Amino acids Gln21-Gly182

First soluble cytokine domain of the human TRAIL ligand (TRAIL, amino acid 120-281 of SEQ ID NO: 1).

C) Amino acids Gly183-Ser 190

First peptide linker element of SEQ ID NO: 2.

D) Amino acids Arg191-Gly351

Second soluble cytokine domain of the human TRAIL ligand (TRAIL, amino acids 121-281 of SEQ ID NO: 1).

E) Amino acids Gly352-Ser359.

Second peptide linker element of SEQ ID NO: 2.

F) Amino acids Arg360-Gly520

Third soluble cytokine domain of the human TRAIL ligand (TRAIL, amino acids 121-281 of SEQ ID NO: 1).

G) Amino acids Gly521-Cys542

Hinge-linker element of SEQ ID NO: 11.

H) Amino acids Pro543-Lys760

Antibody Fc fragment domain of SEQ ID NO: 10.

The above TRAIL receptor agonist protein is shown in SEQ ID NO: 14.

The indicated linkers may be replaced by other preferred linkers, e.g. as shown in SEQ ID NOs: 3-9.

It should be noted that the first and second peptide linkers do not need to be identical.

The signal peptide sequence (A) may be replaced by any other suitable, e.g. mammalian signal peptide sequence.

1.2 Gene Cassette Encoding the Polypeptide

The synthetic gene may be optimized in view of its codon usage for the expression in suitable host cells, e.g. insect cells or mammalian cells. A preferred nucleic acid sequence is shown in SEQ ID NO: 16.

2. Expression and Purification

Cloning, Expression and Purification of Fusion Polypeptides

The aforementioned fusion proteins were expressed recombinantly in two different eukaryotic host cells:

For initial analysis of aforementioned TRAIL receptor agonist fusion proteins, Hek293T cells grown in DMEM+ GlutaMAX (GibCo) supplemented with 10% FBS, 100 units/ml Penicillin and 100 [mu]g/ml Streptomycin were transiently transfected with a plasmid containing an expression cassette for a fusion polypeptide and an appropriate selection marker, e.g. a functional expression cassette comprising a blasticidine, puromycin or hygromycin resistance gene. In those cases, where a plurality of polypeptide chains is necessary to achieve the final product, the expression cassettes were either combined on one plasmid or positioned on different plasmids during the transfection. Cell culture supernatant containing recombinant fusion polypeptide was harvested three days post transfection and clarified by centrifugation at 300×g followed by filtration through a 0.22 μm sterile filter.

For larger scale expression of TRAIL receptor agonist fusion proteins to be used in vivo, synthetic DNA cassettes encoding the aforementioned proteins were inserted into eukaryotic expression vectors comprising appropriate selection markers (e.g. a functional expression cassette comprising a blasticidin, puromycin or hygromycin resistance gene) and genetic elements suitable to enhance the number of transcriptionally active insertion sites within the host cells genome. The sequence verified expression vectors were introduced by electroporation into suspension adapted Chinese Hamster Ovary cells (CHO-S, Invitrogen). Appropriate selection pressure was applied three days post-transfection to the transfected cells. Surviving cells carrying the vector derived resistance gene(s) were recovered by subsequent cultivation under selection pressure. Upon stable growth of the selected cell pools in chemically defined medium (PowerCHO2-CD, Lonza) at 37° C. and 7% CO2 atmosphere in an orbital shaker incubator (100 rpm, 50 mm shaking throw), the individual supernatants were analysed by ELISA-assays detecting the aforementioned proteins and the cell pools with the highest specific productivity were expanded in shake flasks prior to protein production (orbital shaker, 100 rpm, shaking throw 50 mm).

For lab-scale protein production, individual cell pools were cultured for 7-12 days in chemically defined medium (PowerCHO2-CD, Lonza) at 37° C. and 7% CO2 atmosphere in a Wave bioreactor 20/50 EHT (GE-Healthcare). The basal medium was PowerCHO2-CD supplemented with 4 mM Glutamax. Wave culture started with a viable cell concentration of 0.3 to 0.4×10e6 cells/ml and the following settings (for a five- or ten liter bag): shaking frequency 18 rpm, shaking ankle 7°, gas current 0.2-0.3 L/min, 7% CO2, 36.5° C. During the Wave run, the cell culture were fed twice with PowerFeed A (Lonza), usually on day 2 (20% feed) and day 5 (30% feed). After the second feed, shaking frequency was increased to 22rpm, as well as the shaking ankle to 8°.

The bioreactor was usually harvested in between day 7 to day 12 when the cell viability dropped below 80%. First, the culture supernatant was clarified using a manual depth filtration system (Millipore Millistak Pod, MC0HC 0.054 $m^2$). For Strep-tagged proteins, Avidin was added to a final concentration of 0.5 mg/L. Finally, the culture supernatant containing the TRAIL receptor agonist fusion protein was sterile filtered using a bottle top filter (0.22 μm, PES, Corning) and stored at 2-8° C. until further processing.

For affinity purification Streptactin Sepharose was packed to a column (gel bed 1 ml), equilibrated with 15 ml buffer W (100 mM Tris-HCl, 150 mM NaCl, pH 8.0) or PBS pH 7.4 and the cell culture supernatant was applied to the column with a flow rate of 4 ml/min. Subsequently, the column was washed with 15 ml buffer W and bound polypeptide was eluted stepwise by addition of 7×1 ml buffer E (100 mM Tris HCl, 150 mM NaCl, 2.5 mM Desthiobiotin, pH 8.0). Alternately, PBS pH 7.4 containing 2.5 mM Desthiobiotin can be used for this step.

Alternately to the Streptactin Sepharose based method, the affinity purification was performed employing a column with immobilized Protein-A as affinity ligand and a Akta chromatography system (GE-Healthcare). A solid phase material with high affinity for the FC-domain of the fusion protein was chosen: MABSelect Sure™ (GE Healthcare). Briefly, the clarified cell culture supernatant was loaded on a HiTrap MabSelectSure column (CV=5 ml) equilibrated in wash-buffer-1 (20 mM Pi, 95 mM NaCl, pH7.2) not exceeding a load of 10 mg fusion protein per ml column-bed. The column was washed with ten column-volumes (10 CV) of aforementioned equilibration buffer followed by four column-volumes (4 CV) of wash-buffer-2 (20 mM Pi, 95 mM NaCl, pH 8.0) to deplete host-cell protein and host-cell DNA. The column was then eluted with elution buffer (20 mM Pi, 95 mM NaCl, pH 3.5) and the eluate was collected in up to ten fractions with each fraction having a volume equal to column-bed volume (5 ml). Each fraction was neutralized with an equal volume of aforementioned wash-buffer-2. The linear velocity was set to 150 cm/h and kept constant during the aforementioned affinity chromatography method.

The protein amount of the eluate fractions was quantitated and peak fractions were concentrated by ultrafiltration and further purified by size exclusion chromatography (SEC).

SEC was performed on Superdex 200 10/300 GL or HiLoad 26/60 columns using an Akta chromatography system (GE-Healthcare). The columns were equilibrated with phosphate buffered saline and the concentrated, affinity-purified polypeptide was loaded onto the SEC column with the sample volume not exceeding 2% (v/v) of the column-volume. In the case of Superdex200 10/300 GL columns (GE Healthcare), a flow rate of 0.5 ml per minute was applied. In the case of HiLoad 26/60 Superdex200 columns, a flow rate of 2.5 ml per minute was applied. The elution profile of the polypeptide was monitored by absorbance at 280 nm.

For determination of the apparent molecular weight of purified fusion polypeptide under native conditions a Superdex 200 column was loaded with standard proteins of known molecular weight. Based on the elution volume of the standard proteins a calibration curve was plotted and the apparent molecular weight of purified fusion polypeptide was determined. The FC-domain comprising TRAIL receptor agonist fusion proteins typically eluted from the Supoerdex200 columns with an apparent molecular weight for the homodimer of approx. 160-180 kDa.

3. Apoptosis Assay

A cellular assay with a Jurkat A3 permanent T-cell line was used to determine the apoptosis inducing activity of the TRAIL-receptor agonist fusion proteins. Jurkat cells were grown in flasks with RPMI 1640-medium+GlutaMAX (GibCo) supplemented with 10% FBS, 100 units/ml Penicillin and 100 μg/ml Streptomycin. Prior to the assay, 100,000 cells were seeded per well into a 96-well microtiterplate. The addition of different concentrations of fusion peptides to the wells was followed by a 3 hour incubation at 37° C. Cells were lysed by adding lysis buffer (250 mM HEPES, 50 mM $MgCl_2$, 10 mM EGTA, 5% Triton-X-100, 100 mM DTT, 10 mM AEBSF, pH 7.5) and plates were put on ice for 30 minutes to 2 hours. Apoptosis is paralleled by an increased activity of caspases, e.g. Caspase-3. Hence, cleavage of the specific caspase substrate Ac-DEVD-AFC (Biomol) ("DEVD" disclosed as SEQ ID NO: 31) was used to determine the extent of apoptosis. In fact, Caspase activity correlates with the percentage of apoptotic cells determined morphologically after staining the cells with propidium iodide and Hoechst-33342. For the caspase activity assay, 20 μl cell lysate was transferred to a black 96-well microtiterplate. After the addition of 80 μl buffer containing 50 mM HEPES, 1% Sucrose, 0.1% CHAPS, 50 μM Ac-DEVD-AFC ("DEVD" disclosed as SEQ ID NO: 31), and 25 mM DTT, pH 7.5, the plate was transferred to a Tecan Infinite 500 microtiterplate reader and the increase in fluorescence intensity was monitored (excitation wavelength 400 nm, emission wavelength 505 nm).

3.1 Cell Death Assay

For the determination of cell death in HT1080 fibrosarcoma cells 15,000 cells were plated in 96-well plates overnight in RPM1 1640-medium+GlutaMAX (GibCo) supplemented with 10% FBS (Biochrom). Cells were coincubated with cycloheximide (Sigma) at a final concentration of 2.5 g/ml. Cell death was quantified by staining with buffer KV (0.5% crystal violet, 20% methanol). After staining, the wells were washed with water and air-dried. The dye was eluted with methanol and optical density at 595 nm was measured with an ELISA reader.

4. Stability/Aggregation Test 4.1 Principle of the Aggregation Analysis (Definition for Soluble Protein)

The content of monomers (defined trimeric assembly of TRAIL receptor binding modules) and aggregates is determined by analytical SEC as described in Example 2. For this particular purpose the analysis is performed in buffers containing physiological salt concentrations at physiological pH (e.g. 0.9% NaCl, pH 7.4; PBS pH 7.4). A typical aggregation analysis is done on a Superdex200 column (GE Healthcare). This column separates proteins in the range between 10 to 800 kDa.

For determination of the apparent molecular weight of purified fusion polypeptide under native conditions a Superdex 200 column is loaded with standard proteins of known molecular weight. Based on the elution volume of the standard proteins a calibration curve is plotted and the apparent molecular weight of purified fusion polypeptide is calculated based on the elution volume.

SEC analysis of soluble, non-aggregated proteins, e.g. trimeric TRAIL, typically shows a distinct single protein peak at a defined elution volume. This elution volume corresponds to the apparent native molecular weight of the particular protein and approximately complies to the theoretical molecular weight calculated on the basis of the primary amino acid sequence.

If protein aggregation occurs the SEC analysis shows additional protein peaks with lower retention volumes. For TRAIL, the aggregation of soluble proteins occurs in a characteristic manner. The proteins tend to form oligomers of the "timers", forming nonamers (3×3) and 27 mers (3×9). These oligomers serve as aggregation seeds and a high content of oligomers potentially leads to aggregation of the protein. Oligomers of large molecular weight and aggregates elute in the void volume of the Superdex200 column and cannot be analysed by SEC with respect to their native molecular weight.

Due to the induction of (complete) aggregation, purified preparations of TRAIL-SF fusion proteins should preferably contain only defined trimeric proteins and only a very low amount of oligomerised protein. The degree of aggregation/oligomerisation of a particular TRAIL-SF protein preparation is determined on basis of the SEC analysis by calculating the peak areas of the OD280 diagram for the defined trimeric and the oligomer/aggregate fraction, respectively. Based on the total peak area the percentage of defined trimeric protein is calculated as follows:

(% Trimer content=[Peak area trimer]/[Total peak area]×100)

The definition for soluble protein as used in this text, describes a protein preparation of purified TRAIL protein in a buffer of physiological salt concentrations at physiological pH that contains a defined soluble protein (trimeric assembly of TRAIL domains) content of >90% within a typical protein concentration range from 0.2 to 10.0 mg/ml.

5. Half-Life Determination

Molecules A-D are each made up of two polypeptides covalently linked by interchain disulfide bonds. The number of glycosites and hinge cysteines (resulting in interchain disulfide bonds between proteins) were tested in order to determine the effect that altering these characteristics has on the half-life of these compounds.

Female NMRI mice were treated with 1.2 mg/kg bw and/or with 4 mg/kg bw of the specified compounds as a single intravenous bolus injection. Whole blood was collected before application (predose), and up to 168 hours after test item administration. Serum was prepared and samples were stored at −80° C. until determination of serum concentrations. Pharmacokinetic parameters were calculated using the mean serum concentrations and the pharmacokinetic evaluation program PK Solutions Version 2.0 for non-compartmental pharmacokinetic data analysis (Summit Research Services, Montrose, Colo.). PK Solutions is an automated, Excel-based application, which computes pharmacokinetic parameters from concentration-time data obtained from analysis of e.g. biological samples following intravenous or extra-vascular routes of administration. PK Solutions calculates results without presuming any specific compartmental model.

Figure 18:
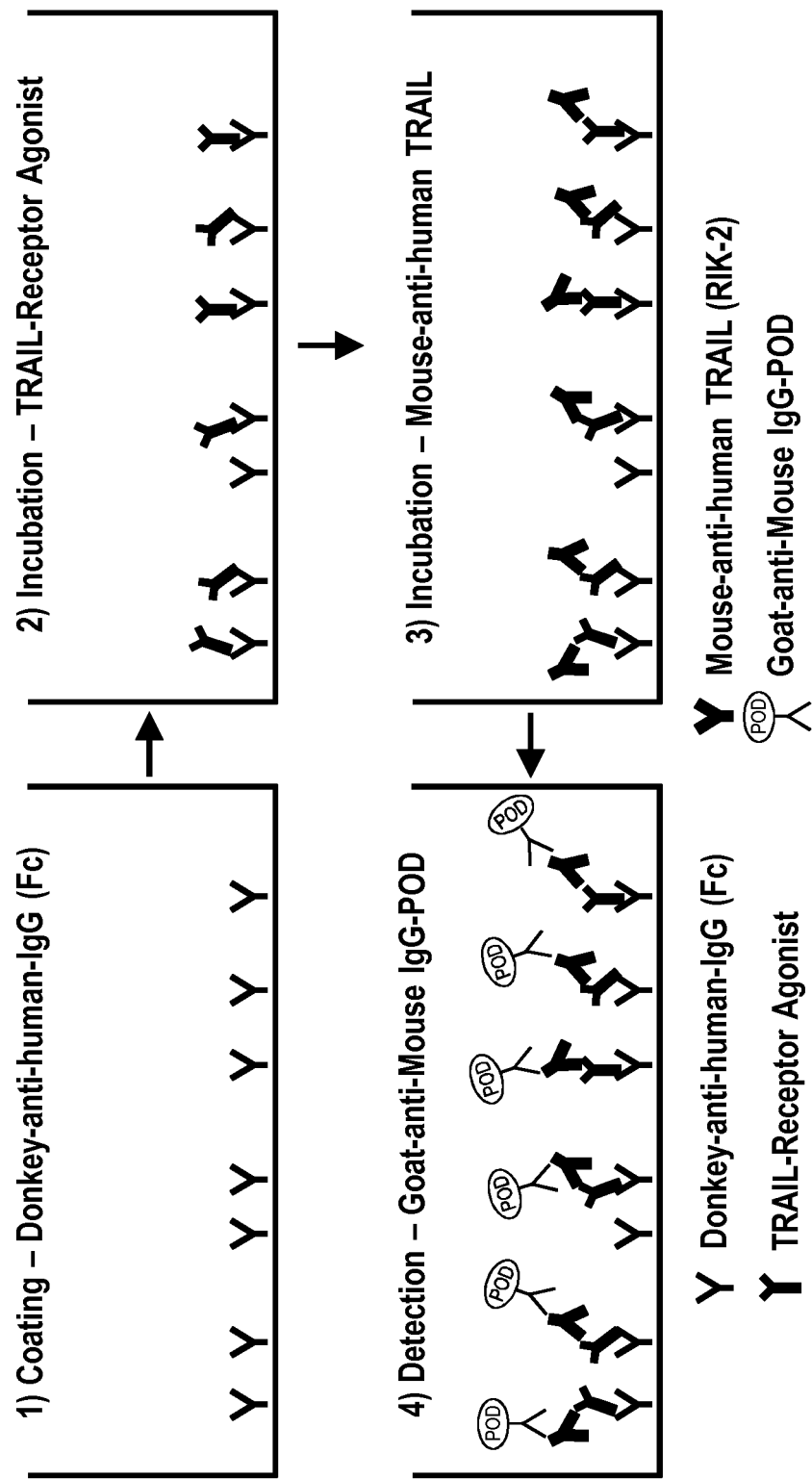
FIG. 18 Assay setup of the ELISA for the quantitation of the TRAIL-receptor agonists containing an FC-domain.

Quantitation of the test items in serum was performed with an ELISA-assay detecting the individual TRAIL-receptor agonists shown in Table 7 independent of a Strep-Tag being part of the molecules. The general layout is shown in FIG. 18. The results are summarized in Table 7.

Molecule A (made up of two polypeptides of SEQ ID NO:26) has two hinge cysteines (forming two interchain disulfide bonds) and an N residue at position 297 of the Fc region (according to the EU index), resulting in wild-type CH2 glycosylation. Molecule A also has glycosites at positions 168 and 337. Molecule B (made up of two polypeptides of SEQ ID NO: 19) has three hinge cysteines (forming three interchain disulfide bonds) (at positions 513, 519, and 522) and an N297S mutation at position 297 of the Fc region (according to the EU index), resulting in aglycosylation of the CH2 domain. Molecule B also has glycosites at positions 168 and 337. Molecule C (made up of two polypeptides of SEQ ID NO: 27) has three hinge cysteines (forming three interchain disulfide bonds) and an N297S mutation at position 297 of the Fc region (according to the EU index), resulting in aglycosylation of the CH2 domain. Further, there is a glycosite at position 168 (linker 1), but not at position 337 (linker 2). Molecule D (made up of two polypeptides of SEQ ID NO:28) has three hinge cysteines (forming three interchain disulfide bonds) and an N297S mutation at position 297 of the Fc region (according to the EU index), resulting in aglycosylation of the CH2 domain. Further, the glycosites on both linker 1 and linker 2 (positions 168 and 337, respectively) have been depleted in Molecule D.

The in vivo stability (as judged by compound half-life) of Molecule B (both linkers glycosylated, CH2 glycosites depleted, and the addition of a third hinge cysteine) was enhanced when compared to Molecule A. Further, the depletion of all glycosites in from the compound (Molecule D) resulted in reduced in vivo stability and low productivity during transient expression. Molecule C (first linker glycosylated, second linker aglycosylated, CH2 glycosites depleted) demonstrated an intermediate in vivo stability when compared to Molecules B and D (see results in Table 7).

TABLE 7

Results of Compound Half-life Testing in NMRI-mice

| Molecule | Number of glycosylation sites | Number of hinge cysteines | Terminal Half-life 4 mg/kg i.v.(hour) | Terminal Half-life 1.2 mg/kg i.v.(hour) |
|---|---|---|---|---|
| A | 6 | 2 | 23.1 | 17.7 |
| B | 4 | 3 | 33.94 | 28.28 |
| C | 2 | 3 | 21.03 | — |
| D | 0 | 3 | 8.81 | — |

These experimental results demonstrate that combining linker glycosylation (in both linkers 1 and 2) with a third interchain disulfide bond (through the addition of a hinge cysteine) and the deglycosylation of the CH2 domain in the Fc region results in greater in vivo stability in the molecules of the instant invention.

Figure 19:
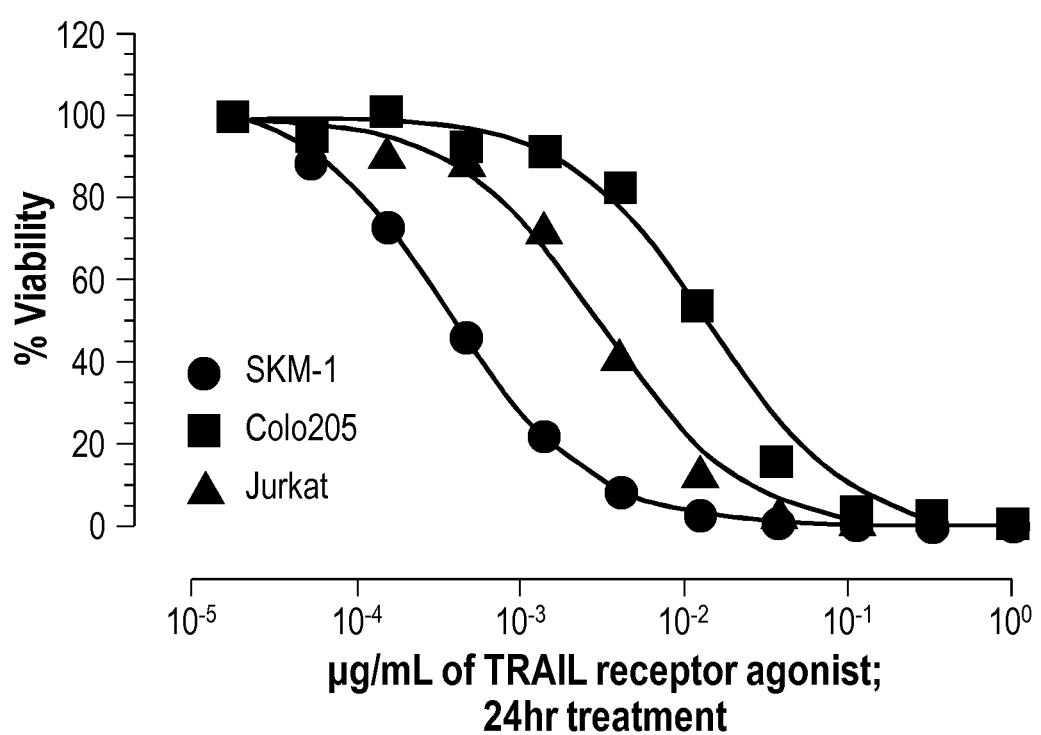
FIG. 19 A TRAIL receptor agonist protein comprising two polypeptides having the amino acid sequence set forth in SEQ ID NO: 19 induces cell death in human tumor cell lines in vitro. SKM-1, Colo205 or Jurkat cells were treated with increasing concentrations the TRAIL receptor agonist protein for 24 hours and cell viability assessed.

6. In vitro Demonstration of Efficacy
6.1 TRAIL Receptor Agonist Protein of SEQ ID NO: 19 Inhibits Human Hematologic and Solid Tumor Cell Survival In vitro Tumor cells were seeded at 10,000 cells/well in 96-well plates in the recommended media containing 10% FBS and treated with a TRAIL receptor agonist protein made up of two polypeptides having the amino acid sequence set forth in SEQ ID NO: 19 for 24 hours at 37° C. in a humidified, 5% $CO_2$ atmosphere. Cell viability was subsequently assessed using CellTiter-Glo® reagent as described by the manufacturer's instructions (Promega; Madison, Wis.). $IC_{50}$ values were determined by non-linear regression analysis of the concentration response data normalized to non-treated control cells. Examples of resulting concentration response curves for Colo205, Jurkat and SKM-1 cells that demonstrate a loss in cell viability in response to TRAIL receptor agonist protein made up of two polypeptides having the amino acid sequence set forth in SEQ ID NO: 19 treatment are shown in FIG. 19. Table 8 shows the results of hematologic (A; (n=40; Non-Hodgkin's Lymphoma, NHL; Acute Myeloid Lymphoma, AML; Acute Lymphoblastic Leukemia, ALL) and solid tumor (B; (n=44; Non-Small Cell Lung Carcinoma, NSCLC; Pancreatic; Colorectal Cancer, CRC; Breast Cancer, BrCa; Ovarian, Fibrosarcoma; Head and Neck, H&N; Small Cell Lung Cancer, SCLC) cell lines treated with a TRAIL receptor agonist protein made up of two polypeptides having the amino acid sequence set forth in SEQ ID NO: 19 for 24 hours and viability assessed by CellTiter-Glo®. Resulting $IC_{50}$s for TRAIL receptor agonist protein made up of two polypeptides having the amino acid sequence set forth in SEQ ID NO: 19-mediated effects on tumor cell viability are presented.

TABLE 8

Potency of TRAIL receptor agonist protein of SEQ ID NO: 19 in human tumor cancer cell lines in vitro

| Tumor cell line | Tumor Type | SEQ ID NO: 19 $IC_{50}$ (ng/ml) |
|---|---|---|
| A | | |
| SU-DHL-8 | NHL | 1.36 |
| NUDHL-1 | NHL | 6.50 |
| OCI-Ly8 | NHL | 7.49 |
| ULA | NHL | 8.44 |
| OCI-Ly2 | NHL | 18.98 |
| OCI-LY19 | NHL | 26.34 |
| WSU-NHL | NHL | 31.60 |
| OCI-Ly7 | NHL | 63.76 |
| SU-DHL-5 | NHL | 82.07 |
| OCI-Ly18 | NHL | 196.20 |
| OCI-Ly1 | NHL | 416.95 |
| SU-DHL-16 | NHL | 545.55 |
| SU-DHL-2 | NHL | 1000.00 |
| WSU-DLCL2 | NHL | 1000.00 |
| Toledo | NHL | 1000.00 |
| OCI-LY3 | NHL | 1000.00 |
| RL | NHL | 1000.00 |
| SU-DHL-4 | NHL | 1000.00 |
| U2932 | NHL | 1000.00 |
| HT | NHL | 1000.00 |
| RC-K8 | NHL | 1000.00 |
| SKM-1 | AML | 0.95 |
| PL-21 | AML | 10.67 |
| EOL-1 | AML | 18.31 |
| HL-60 | AML | 76.62 |
| OCI-AML2 | AML | 124.32 |
| UKE-1 | AML | 205.35 |
| MV4-11 | AML | 312.55 |
| SET-2 | AML | 384.80 |
| MOLM-13 | AML | 722.10 |
| OCI-AML5 | AML | 1032.60 |
| Kasumi-1 | AML | 1000.00 |
| KG-1 | AML | 1000.00 |
| OCI-AML3 | AML | 1000.00 |
| SHI-1 | AML | 1000.00 |
| SKNO-1 | AML | 1000.00 |
| TF-1 | AML | 1000.00 |
| THP-1 | AML | 1000.00 |
| HEL | AML | 1000.00 |
| Jurkat | ALL | 3.08 |
| B | | |
| NCI-H847 | NSCLC | 14.53 |
| NCI-H647 | NSCLC | 24.75 |
| NCI-H2444 | NSCLC | 27.75 |
| NCI-H2170 | NSCLC | 30.16 |
| NCI-H460 | NSCLC | 36.85 |
| NCI-H838 | NSCLC | 44.48 |
| NCI-H1792 | NSCLC | 61.09 |
| NCI-H2347 | NSCLC | 81.06 |
| NCI-H1373 | NSCLC | 125.15 |
| NCI-H522 | NSCLC | 259.87 |

TABLE 8-continued

Potency of TRAIL receptor agonist protein of SEQ ID
NO: 19 in human tumor cancer cell lines in vitro

| Tumor cell line | Tumor Type | SEQ ID NO: 19 IC$_{50}$ (ng/ml) |
|---|---|---|
| NCI-H2110 | NSCLC | 314.20 |
| NCI-H596 | NSCLC | 397.80 |
| HCC4006 | NSCLC | 407.24 |
| NCI-H2122 | NSCLC | 480.55 |
| NCI-H1299 | NSCLC | 716.00 |
| NCI-H1975 | NSCLC | 741.50 |
| HCC827 | NSCLC | 2824.50 |
| NCI-H727 | NSCLC | 3178.00 |
| NCI-H1944 | NSCLC | 4068.75 |
| NCI-H1299 | NSCLC | 4214.87 |
| Calu-6 | NSCLC | 4757.00 |
| NCI-H1693 | NSCLC | 5000.00 |
| HCC2935 | NSCLC | 5000.00 |
| A549 | NSCLC | 5000.00 |
| NCI-H1395 | NSCLC | 5000.00 |
| NCI-H2172 | NSCLC | 5000.00 |
| Calu-1 | NSCLC | 5000.00 |
| NCI-H441 | NSCLC | 5000.00 |
| NCI-H23 | NSCLC | 5000.00 |
| NCI-H661 | NSCLC | 5000.00 |
| NCI-H1650-GFP | NSCLC | >3 |
| BxPC3 | Pancreatic | 16.00 |
| Capan-1 | Pancreatic | 393.00 |
| MIA PaCa-2 | Pancreatic | 158.00 |
| PANC-1 | Pancreatic | >1000 |
| SW48 | CRC | 6.10 |
| Colo205 | CRC | 1.30 |
| SW480 | CRC | 132.00 |
| HCT 116-GFP | CRC | 337.00 |
| HCC38 | BrCa | 3.00 |
| HCC1569 | BrCa | 219.00 |
| MCF7 | BrCa | >3000 |
| MDA-MB-231 | BRCa | 235.00 |
| HeyA8-GFP | Ovarian | 141.00 |
| Fadu-GFP | H&N | >3 |
| HT-1080 | Fibrosarcoma | 377.00 |
| NCI-H211 | SCLC | 72.58 |

6.2 TRAIL Receptor Agonist Protein of SEQ ID NO: 19 Synergizes with Anti-Tumorigenic Agents to Induce Tumor Cell Death Tumor cells were seeded at 10,000 cells/well in 96-well plates in the recommended media containing 10% FBS and co-treated with a TRAIL receptor agonist protein made up of two polypeptides having the amino acid sequence set forth in SEQ ID NO: 19 and venetoclax (ABT-199), navitoclax (ABT-263) or docetaxel (DTX) for 24 hrs at 37° C. in a humidified, 5% CO$_2$ atmosphere. Cell viability was subsequently assessed using CellTiter-Glo® reagent as described by the manufacturer's instructions. The Bliss independence model (Wong et al., 2012; Mol. Cancer Ther. 11:1026-1035; Bernebaum, 1981 Adv. Cancer Res. 35:269-335; Borisy et al., 2003 Proc. Natl. Acad. Sci. USA 100:7977-7982) was employed to assess combination activity, with negative integers indicating antagonism, a value of zero indicating additive activity, and positive integers indicating synergy. Bliss scores were calculated for each combination in the dose matrix and totaled to give a "Bliss sum" value. An example of synergistic tumor cell death induced by co-treating human tumor cells with a TRAIL receptor agonist protein made up of two polypeptides having the amino acid sequence set forth in SEQ ID NO:19 and venetoclax, navitoclax or DTX, with the associated Bliss sum is shown in FIGS. 20(A-C). Bliss sums determined for these combinations in a number of tumor cell lines are depicted in Table 9.

TABLE 9

Bliss synergy assessment of cell killing by TRAIL receptor agonist protein of SEQ ID NO: 19 in combination with DTX in NSCLC cell lines (A) and and venetoclax or navitoclax in NHL & AML cell lines (B) in vitro.

| Tumor Cell line | Bliss Sum (SEQ ID NO: 19 + DTX) | Tumor Cell line | Bliss Sum (SEQ ID NO: 19 + venitoclax) | Bliss Sum (SEQ ID NO: 19 + navitoclax) |
|---|---|---|---|---|
| LG0552 | 748.2 | WSU-DLCL2 | 1292 | 560 |
| NCI-H522 | 549.1 | SU-DHL-4 | 898 | 617 |
| NCI-H647 | 452 | OCI-AML3 | 831.9 | 456.4 |
| NCI-H727 | 429.4 | OCI-AML5 | 777.8 | 174.5 |
| NCI-H1373 | 387.1 | U2932 | 736.2 | 636.1 |
| NCI-H596 | 261 | PL-21 | 600.8 | 244.9 |
| HCC2935 | 224.2 | ULA | 343.8 | 79.4 |
| NCI-H2347 | 154 | OCI-Ly18 | 309.8 | 8.3 |
| NCI-H2444 | 135 | MV4; 11 | 301.1 | 351 |
| A549 | 118.1 | RL | 286.1 | 446.7 |
| NCI-H23 | 70.6 | MOLM-13 | 270.6 | 264.8 |
| NCI-H847 | 64.2 | SKM-1 | 222.9 | 88.1 |
| HCC4006 | 15.75 | OCI-Ly1 | 218.8 | 69.1 |
| NCI-H2170 | −97.1 | SU-DHL-16 | 217.5 | 142.5 |
| LG0567 | −105.2 | OCI-AMl2 | 160.2 | 145.5 |
| HCC2935 | −183 | OCI-Ly8 | 154.9 | 177 |
| HCC827 | −292.8 | THP-1 | 152.7 | 43.1 |
| NCI-H661 | −344.5 | OCI-Ly3 | 146.5 | −242.2 |
| NCI-H441 | −362 | OCI-Ly2 | 145 | 127.2 |
| NCI-H1395 | −512 | OCI-Ly19 | 114.9 | 37.3 |
| NCI-H1944 | −565 | SKNO-1 | 104.7 | −138.9 |
| NCI-H1693 | −584 | UKE-1 | 80.5 | 28.9 |
| Calu-6 | −628.7 | WSU-NHK | 79.8 | 84 |
| LG0481 | −803 | EOL-1 | 69.7 | −6.3 |
| NCI-H2172 | −1404 | SU-DHL-2 | 53.5 | −31.8 |
|  |  | Toledo | 51.4 | −68.2 |
|  |  | HEL | 21.5 | −92.4 |
|  |  | NuDHL-1 | −28.4 | 18.7 |
|  |  | TF-1 | −100.6 | −50.2 |
|  |  | RC-K8 | −131 | −68 |
|  |  | HT | −173 | 12.1 |
|  |  | HL-60 | −176 | −112.7 |
|  |  | SHI-1 | −208.4 | −122.6 |
|  |  | SU-DHL-8 | −210.6 | −37 |
|  |  | SU-DHL-5 | −233.8 | −280.6 |
|  |  | SET-2 | −248.4 | 71.2 |
|  |  | KG-1 | −260 | −20.3 |
|  |  | Kasumi-1 | −356.4 | −241.2 |

Figure 21:
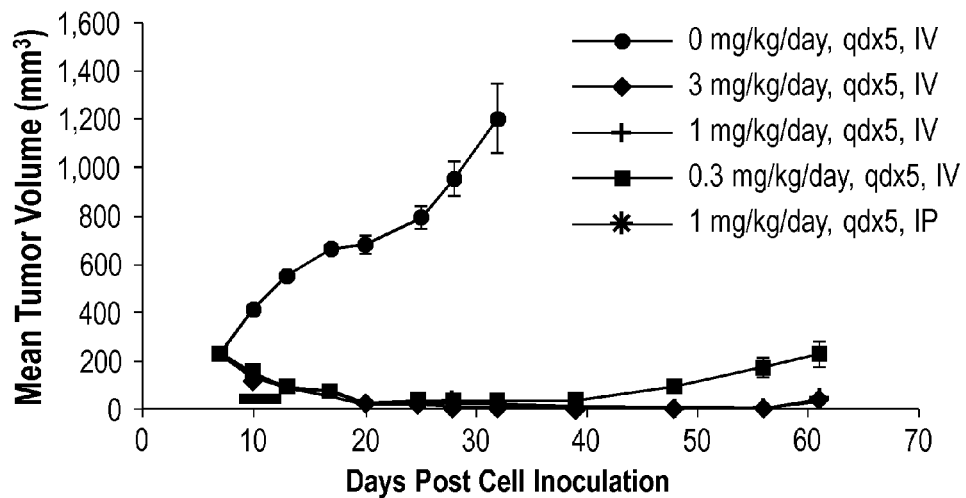
FIG. 21 Effect of TRAIL receptor agonist protein comprising two polypeptides having the amino acid sequence set forth in SEQ ID NO: 19 on tumor growth in the Colo205 colorectal carcinoma xenograft model.
Figure 22:
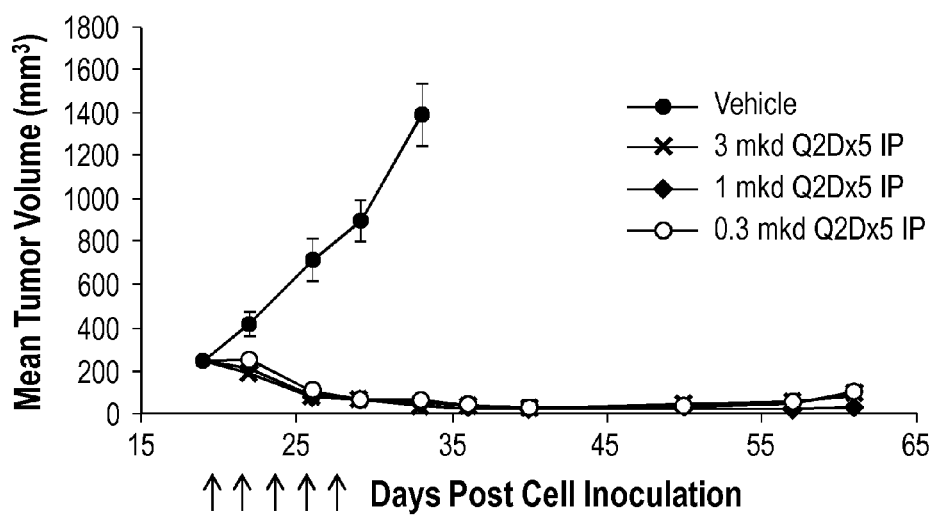
FIG. 22 Effect of TRAIL receptor agonist protein comprising two polypeptides having the amino acid sequence set forth in SEQ ID NO: 19 on tumor growth in the SKM-1 acute myeloid leukemia xenograft model.
Figure 24A:
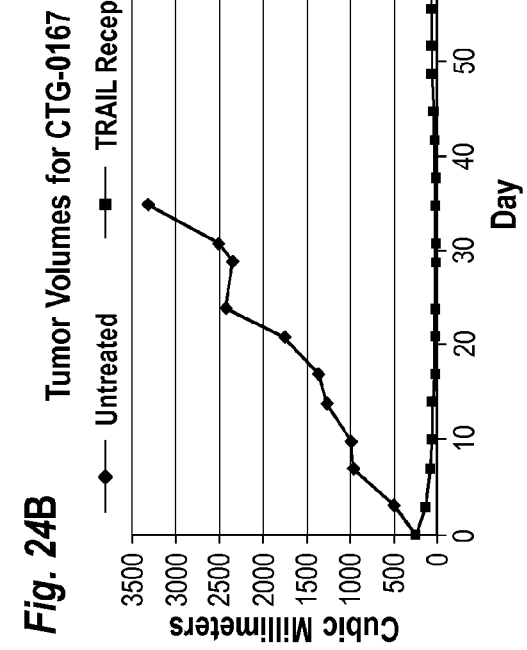
Figure 24B:
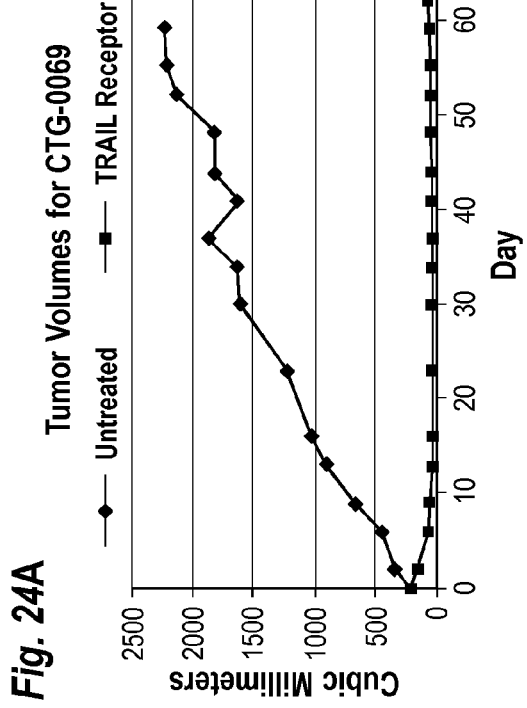
Figure 24C:
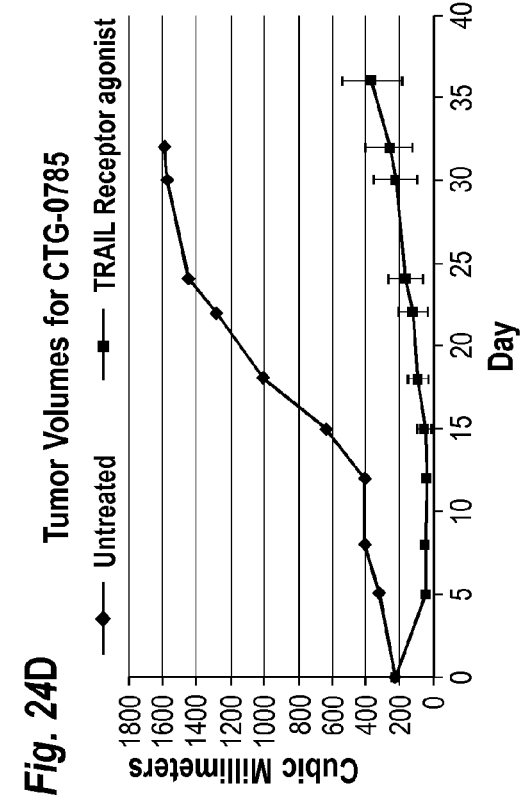
Figure 24D:
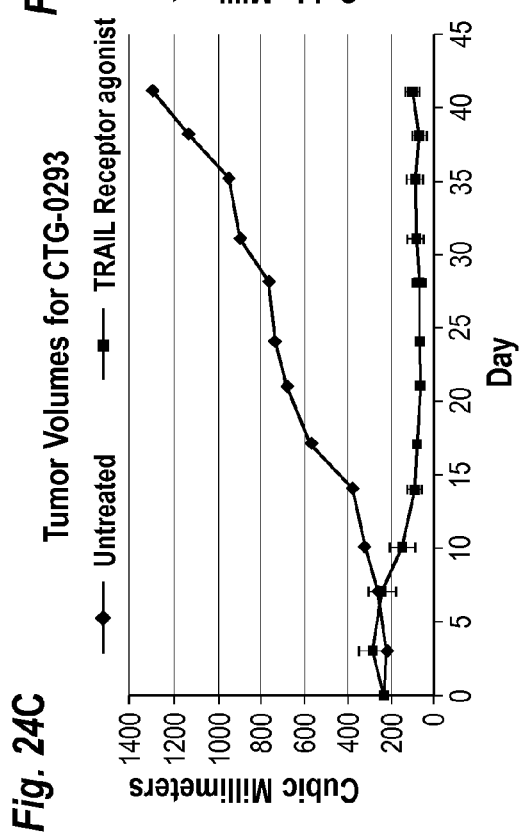

7. TRAIL Receptor Agonist Protein of SEQ ID NO:19 Treatment Inhibits Tumor Growth In vivo The effect of a TRAIL receptor agonist protein made up of two polypeptides having the amino acid sequence set forth in SEQ ID NO:19 on tumor growth was evaluated in subcutaneous Colo205 (colorectal), SKM-1 (acute myeloid leukemia), and H460LM (non-small cell lung) xenograft tumors implanted in SCID female mice (Charles Rivers Laboratories; Wilmington, Mass.). Briefly, human cancer cells were inoculated subcutaneously into the right hind flank of female SCID mice on study day 0. Administration of TRAIL receptor agonist protein of SEQ ID NO:19 (0.3, 1, or 3 mkd dosed IV, QDx5 or IP, Q2Dx5 as indicated) was initiated at the time of size match. Tumor volume was measured for the duration of the experiment until the mean tumor volume in each group reached an endpoint of >2000 mm$^3$ for Colo205 and SKM-1 or >2500 mm$^3$ for H460LM. Results are shown in FIGS. 21-23. Administration of a TRAIL receptor agonist protein made up of two polypeptides having the amino acid sequence set forth in SEQ ID NO:19 induced significant tumor growth inhibition in the Colo205, SKM-1, and H460LM xenograft tumor models.

The effect of a TRAIL receptor agonist protein made up of two polypeptides having the amino acid sequence set forth in SEQ ID NO:19 on tumor growth was also evaluated in patient-derived xenograft models CTG-0069 (colorectal), CTG-0167 (NSCLC), CTG-0293 (pancreatic), CTG-0714 (sarcoma), CTG-0136 (esophageal), CTG-485 (gastric), and CTG-0785 (Ewing's sarcoma) implanted in NSG female mice (Champions Oncology; Hackensack, N.J.). Briefly, tumor fragments were propagated subcutaneously into the right hind flank of female NSG mice on study day 0. Administration of a TRAIL receptor agonist protein made up of two polypeptides having the amino acid sequence set forth in SEQ ID NO: 19 (3 mkd dosed IP, Q2Dx5) was initiated at the time of size match. Tumor volume was measured for the duration of the experiment until the mean tumor volume in each group reached an endpoint of >2000 mm$^3$ or 60 days. Results are shown in FIGS. 24(A-G). Administration of a TRAIL receptor agonist protein made up of two polypeptides having the amino acid sequence set forth in SEQ ID NO: 19 induced significant tumor growth inhibition in the CTG-0069 (colorectal), CTG-0167 (NSCLC), CTG-0293 (pancreatic), CTG-0714 (sarcoma), CTG-0136 (esophageal), CTG-485 (gastric), and CTG-0785 (Ewing's sarcoma) PDX models.

The invention claimed is:

1. A TRAIL receptor agonist protein comprising a polypeptide having the amino acid sequence set forth in SEQ ID NO: 19.

2. A TRAIL receptor agonist protein comprising a dimer of two polypeptides having the amino acid sequence set forth in SEQ ID NO: 19.

3. The TRAIL receptor agonist protein of claim 1, wherein one or more of the asparagine residues at positions 168 and 337 of the polypeptide are N-glycosylated.

4. The TRAIL receptor agonist protein of claim 1, wherein the asparagine residues at positions 168 and 337 of the polypeptide are both N-glycosylated.

5. The TRAIL receptor agonist protein of claim 1, wherein the polypeptide is further post-translationally modified.

6. The TRAIL receptor agonist protein of claim 5, wherein the post-translational modification comprises modification of the N-terminal glutamine to pyroglutamate.

7. A pharmaceutical composition comprising the TRAIL receptor agonist protein of claim I and one or more pharmaceutically acceptable carriers, diluents, excipients, and/or adjuvants.

8. A nucleic acid molecule encoding the TRAIL receptor agonist protein of claim 1.

9. An expression vector comprising the nucleic acid molecule of claim 8.

10. An isolated cell comprising the nucleic acid molecule of claim 8.

11. The cell of claim 10, which is a eukaryotic cell.

12. The cell of claim 10, wherein the cell s a mammalian cell.

13. The cell of claim 10, wherein the cell is a Chinese Hamster Ovary (CHO) cell.

14. A method of treating cancer comprising administering to a subject having cancer an effective amount of the TRAIL receptor agonist protein of claim 1.

15. The method of claim 14, wherein the cancer comprises a tumor.

16. The method of claim 15, wherein the tumor is a solid tumor.

17. The method of claim 15, wherein the tumor is a lymphatic tumor.

18. The TRAIL receptor agonist protein of claim 2, wherein the two polypeptides are covalently linked through three interchain disulfide bonds formed between cysteine residues 513, 519, and 522 of each polypeptide.

19. The TRAIL receptor agonist protein of claim 18, wherein one or more of the asparagine residues at positions 168 and 337 of the polypeptides are N-glycosylated.

20. The TRAIL receptor agonist protein of claim 19, wherein the asparagine residues at positions 168 and 337 of the polypeptides are both N-glycosylated.

21. The TRAIL receptor agonist protein of claim 19, wherein one or more of the polypeptides are further post-translationally modified.

22. The TRAIL receptor agonist protein of claim 21, wherein the post-translational modification comprises modification of the N-terminal glutamine to pyroglutamate.

23. A pharmaceutical composition comprising the TRAIL receptor agonist protein of claim 18 and one or more pharmaceutically acceptable carriers, diluents, excipients, and/or adjuvants.

24. A method of treating cancer comprising administering to a subject having cancer an effective amount of the TRAIL receptor agonist protein of claim 18.

25. The method of claim 24, wherein the cancer comprises a tumor.

26. The method of claim 25, wherein the tumor is a solid tumor.

27. The method of claim 25, wherein the tumor is a lymphatic tumor.

* * * * *

UNITED STATES PATENT AND TRADEMARK OFFICE
CERTIFICATE OF CORRECTION

PATENT NO. : 9,908,927 B2
APPLICATION NO. : 14/694358
DATED : March 6, 2018
INVENTOR(S) : Hill et al.

Page 1 of 1

It is certified that error appears in the above-identified patent and that said Letters Patent is hereby corrected as shown below:

In the Specification

Column 4, Line 31, "Venetoclax, In" to read as --Venetoclax. In--

Column 4, Line 39, "to a patient byoral," to read as --to a patient by oral,--

Column 5, Line 30, "of the next" to read as --of the next soluble domain.--

Column 8, table 1, SEQ ID NO: 1, "LRQLVRKMILRTSEETISTVQEKQQNISPLVRERGPORVAAHI" to read as --LRQLVRKMILRTSEETISTVQEKQQNISPLVRERGPQRVAAHI--

Column 17, table 6, SEQ ID NO: 16, "cgagaagggcttclactacatctactcccagacct" to read as --cgagaagggcttctactacatctactcccagacct--

Column 25, Line 26, "a blasticidine," to read as --a blasticidin--

Column 25, Line 40, "hygromycin resistence gene)" to read as --hygromycin resistance gene)--

In the Claims

Column 89, Line 29, Claim 7, "of claim I and" to read as --of claim 1 and--

Column 89, Line 38, Claim 11, "of claim 10, which is a eukaryotic cell." to read as --of claim 10, wherein the cell is a eukaryotic cell.--

Column 89, Line 39, Claim 12, "the cell s a" to read as --the cell is a--

Signed and Sealed this
Thirtieth Day of October, 2018

Andrei Iancu
*Director of the United States Patent and Trademark Office*

SEQUENCE LISTING

```
<160> NUMBER OF SEQ ID NOS: 31

<210> SEQ ID NO 1
<211> LENGTH: 281
<212> TYPE: PRT
<213> ORGANISM: Homo sapiens
<220> FEATURE:
<221> NAME/KEY: source
<223> OTHER INFORMATION: /note="human TRAIL"

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280
```

```
<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 2

Gly Ser Gly Ser Gly Asn Gly Ser
1               5

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 3

Gly Ser Gly Ser Gly Ser Gly Ser
1               5

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 4

Gly Gly Ser Gly Ser Gly Ser Gly
1               5

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 5

Gly Gly Ser Gly Ser Gly
1               5

<210> SEQ ID NO 6
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 6

Gly Gly Ser Gly
1

<210> SEQ ID NO 7
<211> LENGTH: 8
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 7

Gly Gly Ser Gly Asn Gly Ser Gly
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 8

Gly Gly Asn Gly Ser Gly Ser Gly
1               5

<210> SEQ ID NO 9
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 9

Gly Gly Asn Gly Ser Gly
1               5

<210> SEQ ID NO 10
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Fc fragment polypeptide"

<400> SEQUENCE: 10

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Ser Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
```

-continued

```
            130                 135                 140
Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 11
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic hinge-linker peptide"

<400> SEQUENCE: 11

Gly Pro Gly Ser Ser Ser Ser Ser Ser Gly Ser Cys Asp Lys Thr
1               5                   10                  15

His Thr Cys Pro Pro Cys
            20

<210> SEQ ID NO 12
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic signal peptide"

<400> SEQUENCE: 12

Met Glu Thr Asp Thr Leu Leu Val Phe Val Leu Leu Val Trp Val Pro
1               5                   10                  15

Ala Gly Asn Gly
            20

<210> SEQ ID NO 13
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic strep-tag + serine linker peptide"

<400> SEQUENCE: 13

Ser Ser Ser Ser Ser Ser Ala Trp Ser His Pro Gln Phe Glu Lys
1               5                   10                  15

<210> SEQ ID NO 14
<211> LENGTH: 760
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic single-chain fusion polypeptide"

<400> SEQUENCE: 14
```

```
Met Glu Thr Asp Thr Leu Leu Val Phe Val Leu Leu Val Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
                100                 105                 110

Lys Tyr Thr Ser Tyr Pro Asp Pro Ile Leu Leu Met Lys Ser Ala Arg
            115                 120                 125

Asn Ser Cys Trp Ser Lys Asp Ala Glu Tyr Gly Leu Tyr Ser Ile Tyr
        130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Gly Ser Gly Ser Gly Asn Gly Ser Arg Val
            180                 185                 190

Ala Ala His Ile Thr Gly Thr Arg Gly Arg Ser Asn Thr Leu Ser Ser
        195                 200                 205

Pro Asn Ser Lys Asn Glu Lys Ala Leu Gly Arg Lys Ile Asn Ser Trp
210                 215                 220

Glu Ser Ser Arg Ser Gly His Ser Phe Leu Ser Asn Leu His Leu Arg
225                 230                 235                 240

Asn Gly Glu Leu Val Ile His Glu Lys Gly Phe Tyr Tyr Ile Tyr Ser
                245                 250                 255

Gln Thr Tyr Phe Arg Phe Gln Glu Glu Ile Lys Glu Asn Thr Lys Asn
            260                 265                 270

Asp Lys Gln Met Val Gln Tyr Ile Tyr Lys Tyr Thr Ser Tyr Pro Asp
        275                 280                 285

Pro Ile Leu Leu Met Lys Ser Ala Arg Asn Ser Cys Trp Ser Lys Asp
290                 295                 300

Ala Glu Tyr Gly Leu Tyr Ser Ile Tyr Gln Gly Gly Ile Phe Glu Leu
305                 310                 315                 320

Lys Glu Asn Asp Arg Ile Phe Val Ser Val Thr Asn Glu His Leu Ile
                325                 330                 335

Asp Met Asp His Glu Ala Ser Phe Phe Gly Ala Phe Leu Val Gly Gly
            340                 345                 350

Ser Gly Ser Gly Asn Gly Ser Arg Val Ala Ala His Ile Thr Gly Thr
        355                 360                 365

Arg Gly Arg Ser Asn Thr Leu Ser Ser Pro Asn Ser Lys Asn Glu Lys
370                 375                 380

Ala Leu Gly Arg Lys Ile Asn Ser Trp Glu Ser Ser Arg Ser Gly His
385                 390                 395                 400

Ser Phe Leu Ser Asn Leu His Leu Arg Asn Gly Glu Leu Val Ile His
                405                 410                 415
```

Glu Lys Gly Phe Tyr Tyr Ile Tyr Ser Gln Thr Tyr Phe Arg Phe Gln
            420                 425                 430

Glu Glu Ile Lys Glu Asn Thr Lys Asn Asp Lys Gln Met Val Gln Tyr
                435                 440                 445

Ile Tyr Lys Tyr Thr Ser Tyr Pro Asp Pro Ile Leu Leu Met Lys Ser
450                 455                 460

Ala Arg Asn Ser Cys Trp Ser Lys Asp Ala Glu Tyr Gly Leu Tyr Ser
465                 470                 475                 480

Ile Tyr Gln Gly Gly Ile Phe Glu Leu Lys Glu Asn Asp Arg Ile Phe
                485                 490                 495

Val Ser Val Thr Asn Glu His Leu Ile Asp Met Asp His Glu Ala Ser
                500                 505                 510

Phe Phe Gly Ala Phe Leu Val Gly Gly Pro Gly Ser Ser Ser Ser Ser
            515                 520                 525

Ser Ser Gly Ser Cys Asp Lys Thr His Thr Cys Pro Pro Cys Pro Ala
530                 535                 540

Pro Glu Leu Leu Gly Gly Pro Ser Val Phe Leu Phe Pro Pro Lys Pro
545                 550                 555                 560

Lys Asp Thr Leu Met Ile Ser Arg Thr Pro Glu Val Thr Cys Val Val
                565                 570                 575

Val Asp Val Ser His Glu Asp Pro Glu Val Lys Phe Asn Trp Tyr Val
            580                 585                 590

Asp Gly Val Glu Val His Asn Ala Lys Thr Lys Pro Arg Glu Glu Gln
                595                 600                 605

Tyr Ser Ser Thr Tyr Arg Val Val Ser Val Leu Thr Val Leu His Gln
610                 615                 620

Asp Trp Leu Asn Gly Lys Glu Tyr Lys Cys Lys Val Ser Asn Lys Ala
625                 630                 635                 640

Leu Pro Ala Pro Ile Glu Lys Thr Ile Ser Lys Ala Lys Gly Gln Pro
                645                 650                 655

Arg Glu Pro Gln Val Tyr Thr Leu Pro Pro Ser Arg Glu Glu Met Thr
            660                 665                 670

Lys Asn Gln Val Ser Leu Thr Cys Leu Val Lys Gly Phe Tyr Pro Ser
                675                 680                 685

Asp Ile Ala Val Glu Trp Glu Ser Asn Gly Gln Pro Glu Asn Asn Tyr
690                 695                 700

Lys Thr Thr Pro Pro Val Leu Asp Ser Asp Gly Ser Phe Phe Leu Tyr
705                 710                 715                 720

Ser Lys Leu Thr Val Asp Lys Ser Arg Trp Gln Gln Gly Asn Val Phe
                725                 730                 735

Ser Cys Ser Val Met His Glu Ala Leu His Asn His Tyr Thr Gln Lys
            740                 745                 750

Ser Leu Ser Leu Ser Pro Gly Lys
        755                 760

<210> SEQ ID NO 15
<211> LENGTH: 774
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic single-chain fusion polypeptide"

<400> SEQUENCE: 15

Met Glu Thr Asp Thr Leu Leu Val Phe Val Leu Leu Val Trp Val Pro

-continued

```
  1               5                  10                 15
Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
            35                  40                  45

Gly Arg Lys Ile Asn Ser Trp Glu Ser Ser Arg Ser Gly His Ser Phe
 50                  55                  60

Leu Ser Asn Leu His Leu Arg Asn Gly Glu Leu Val Ile His Glu Lys
 65                  70                  75                  80

Gly Phe Tyr Tyr Ile Tyr Ser Gln Thr Tyr Phe Arg Phe Gln Glu Glu
                    85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
            115                 120                 125

Asn Ser Cys Trp Ser Lys Asp Ala Glu Tyr Gly Leu Tyr Ser Ile Tyr
            130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                    165                 170                 175

Gly Ala Phe Leu Val Gly Gly Ser Gly Ser Gly Asn Gly Ser Arg Val
            180                 185                 190

Ala Ala His Ile Thr Gly Thr Arg Gly Arg Ser Asn Thr Leu Ser Ser
            195                 200                 205

Pro Asn Ser Lys Asn Glu Lys Ala Leu Gly Arg Lys Ile Asn Ser Trp
            210                 215                 220

Glu Ser Ser Arg Ser Gly His Ser Phe Leu Ser Asn Leu His Leu Arg
225                 230                 235                 240

Asn Gly Glu Leu Val Ile His Glu Lys Gly Phe Tyr Tyr Ile Tyr Ser
                    245                 250                 255

Gln Thr Tyr Phe Arg Phe Gln Glu Glu Ile Lys Glu Asn Thr Lys Asn
            260                 265                 270

Asp Lys Gln Met Val Gln Tyr Ile Tyr Lys Tyr Thr Ser Tyr Pro Asp
            275                 280                 285

Pro Ile Leu Leu Met Lys Ser Ala Arg Asn Ser Cys Trp Ser Lys Asp
            290                 295                 300

Ala Glu Tyr Gly Leu Tyr Ser Ile Tyr Gln Gly Gly Ile Phe Glu Leu
305                 310                 315                 320

Lys Glu Asn Asp Arg Ile Phe Val Ser Val Thr Asn Glu His Leu Ile
                    325                 330                 335

Asp Met Asp His Glu Ala Ser Phe Phe Gly Ala Phe Leu Val Gly Gly
            340                 345                 350

Ser Gly Ser Gly Asn Gly Ser Arg Val Ala Ala His Ile Thr Gly Thr
            355                 360                 365

Arg Gly Arg Ser Asn Thr Leu Ser Ser Pro Asn Ser Lys Asn Glu Lys
            370                 375                 380

Ala Leu Gly Arg Lys Ile Asn Ser Trp Glu Ser Ser Arg Ser Gly His
385                 390                 395                 400

Ser Phe Leu Ser Asn Leu His Leu Arg Asn Gly Glu Leu Val Ile His
                    405                 410                 415

Glu Lys Gly Phe Tyr Tyr Ile Tyr Ser Gln Thr Tyr Phe Arg Phe Gln
            420                 425                 430
```

Glu Glu Ile Lys Glu Asn Thr Lys Asn Asp Lys Gln Met Val Gln Tyr
            435                 440                 445

Ile Tyr Lys Tyr Thr Ser Tyr Pro Asp Pro Ile Leu Leu Met Lys Ser
    450                 455                 460

Ala Arg Asn Ser Cys Trp Ser Lys Asp Ala Glu Tyr Gly Leu Tyr Ser
465                 470                 475                 480

Ile Tyr Gln Gly Gly Ile Phe Glu Leu Lys Glu Asn Asp Arg Ile Phe
                485                 490                 495

Val Ser Val Thr Asn Glu His Leu Ile Asp Met Asp His Glu Ala Ser
                500                 505                 510

Phe Phe Gly Ala Phe Leu Val Gly Gly Pro Gly Ser Ser Ser Ser Ser
            515                 520                 525

Ser Ser Gly Ser Cys Asp Lys Thr His Thr Cys Pro Pro Cys Pro Ala
530                 535                 540

Pro Glu Leu Leu Gly Gly Pro Ser Val Phe Leu Phe Pro Pro Lys Pro
545                 550                 555                 560

Lys Asp Thr Leu Met Ile Ser Arg Thr Pro Glu Val Thr Cys Val Val
                565                 570                 575

Val Asp Val Ser His Glu Asp Pro Glu Val Lys Phe Asn Trp Tyr Val
            580                 585                 590

Asp Gly Val Glu Val His Asn Ala Lys Thr Lys Pro Arg Glu Glu Gln
                595                 600                 605

Tyr Ser Ser Thr Tyr Arg Val Val Ser Val Leu Thr Val Leu His Gln
    610                 615                 620

Asp Trp Leu Asn Gly Lys Glu Tyr Lys Cys Lys Val Ser Asn Lys Ala
625                 630                 635                 640

Leu Pro Ala Pro Ile Glu Lys Thr Ile Ser Lys Ala Lys Gly Gln Pro
                645                 650                 655

Arg Glu Pro Gln Val Tyr Thr Leu Pro Pro Ser Arg Glu Glu Met Thr
            660                 665                 670

Lys Asn Gln Val Ser Leu Thr Cys Leu Val Lys Gly Phe Tyr Pro Ser
        675                 680                 685

Asp Ile Ala Val Glu Trp Glu Ser Asn Gly Gln Pro Glu Asn Asn Tyr
690                 695                 700

Lys Thr Thr Pro Pro Val Leu Asp Ser Asp Gly Ser Phe Phe Leu Tyr
705                 710                 715                 720

Ser Lys Leu Thr Val Asp Lys Ser Arg Trp Gln Gln Gly Asn Val Phe
                725                 730                 735

Ser Cys Ser Val Met His Glu Ala Leu His Asn His Tyr Thr Gln Lys
            740                 745                 750

Ser Leu Ser Leu Ser Pro Gly Ser Ser Ser Ser Ser Ser Ala Trp Ser
        755                 760                 765

His Pro Gln Phe Glu Lys
    770

<210> SEQ ID NO 16
<211> LENGTH: 2316
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic DNA polynucleotide sequence encoding a single-chain
      fusion polypeptide"

<400> SEQUENCE: 16

```
gatatcggta ccgccaccat ggaaaccgac accctgctgg tgttcgtgct gctcgtgtgg      60
gtgccagccg gcaatggaca gagagtggcc gctcatatca ccggcacccg ggcagatct      120
aacaccctgt ccagccccaa ctccaagaac gagaaggccc tgggccggaa gatcaactcc     180
tgggagtcct ccagatccgg ccactccttt ctgtccaacc tgcacctgag aaacggcgag     240
ctggtcatcc acgagaaggg cttctactac atctactccc agacctactt caggtttcag     300
gaagagatca aagagaacac aaagaacgac aagcagatgg tgcagtatat ctacaagtac     360
acctcctacc ccgaccccat cctgctgatg aagtccgccc ggaactcctg ctggtccaag     420
gatgctgagt acggcctgta cagcatctac cagggcggca tcttcgagct gaaagagaac     480
gaccggatct tcgtgtccgt gaccaacgag cacctgatcg acatggacca cgaggccagc     540
tttttcggcg cctttctcgt gggcggatcc ggaagcggaa acggcagtag agtggctgcc     600
cacattaccg gaaccagagg ccggtccaac accctgagca gccctaacag caaaaatgag     660
aaagctctcg ggcgcaagat caacagctgg gaatctagca gaagcggcca cagctttctg     720
agcaatctgc atctgcggaa cggcgaactc gtgattcatg agaaggggtt ttattatatc     780
tatagccaga catactttcg attccaggag gaaatcaagg aaaacaccaa aaatgataaa     840
cagatggtcc agtacatttta taagtatacc agctaccctg atcctatcct cctcatgaag      900
tctgccagaa actcttgttg gagcaaggac gccgagtatg gactgtactc tatctatcag     960
gggggggatct ttgaactcaa agaaaacgat cgcatctttg tcagcgtcac caatgagcat    1020
ctcattgata tggatcatga agctagtttc ttcggggcat tcctcgtggg aggctccggc    1080
tctggcaacg gatctagagt cgccgcacac atcacaggga ccagaggcag aagcaatacc    1140
ctgtcctccc caaatagtaa aaacgaaaag gcactcggcc gcaaaattaa ttcctgggag    1200
agcagcagat ccgggcacag ttttctgtct aatctccatc tgaggaatgg ggagctggtg    1260
attcacgaaa aaggatttta ctacatttac agtcagactt actttcgttt tcaggaagag    1320
attaaggaaa ataccaaaaa cgacaagcag atggtccagt acatctataa atacacctct    1380
tatcctgacc caattctgct catgaagagt gcccgcaaca gctgctggtc taaagacgcc    1440
gaatacgggc tgtattccat ttaccagggg ggaattttttg agctgaagga aaatgatcgg    1500
attttttgtct ctgtcacaaa cgaacacctc atcgatatgg atcacgaagc ctcttttcttt   1560
ggcgccttcc tggtcggagg ccctggctcg agttccagct cctcttctgg ctcctgcgac    1620
aagacccaca cctgtccccc ttgtcctgcc cctgaactgc tgggcggacc ttccgtgttc    1680
ctgttccccc caaagcccaa ggacaccctg atgatctccc ggacccccga agtgacctgc    1740
gtggtggtgg atgtgtctca cgaggaccct gaagtgaagt tcaattggta cgtggacggc    1800
gtggaagtgc acaacgccaa gaccaagccc agagaggaac agtactcctc cacctaccgg    1860
gtggtgtctg tgctgaccgt gctgcaccag gactggctga acggcaaaga gtacaagtgc    1920
aaggtgtcca acaaggccct gcctgccccc atcgaaaaga ccatctccaa ggccaagggc    1980
cagccccggg aacccaggt gtacacactg cccctagcc gggaagagat gaccaagaac    2040
caggtgtccc tgacctgcct ggtcaagggc ttttacccct ccgacattgc cgtggaatgg    2100
gagtccaacg gccagcctga gaacaactac aagaccaccc ccctgtgct ggactccgac    2160
ggctcattct tcctgtactc caagctgaca gtggacaagt cccggtggca gcagggcaac    2220
gtgttctcct gctccgtgat gcacgaggcc ctgcacaacc actacaccca gaagtccctg    2280
tccctgagcc ccggcaaatg atagaagctt gatatc                              2316
```

```
<210> SEQ ID NO 17
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic human Fc mutein polypeptide"

<400> SEQUENCE: 17

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 18
<211> LENGTH: 759
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Glu Thr Asp Thr Leu Leu Val Phe Val Leu Leu Val Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
```

-continued

```
            65                  70                  75                  80
Gly Phe Tyr Tyr Ile Tyr Ser Gln Thr Tyr Phe Arg Phe Gln Glu Glu
                    85                  90                  95
Ile Lys Glu Asn Thr Lys Asn Asp Lys Gln Met Val Gln Tyr Ile Tyr
                   100                 105                 110
Lys Tyr Thr Ser Tyr Pro Asp Pro Ile Leu Leu Met Lys Ser Ala Arg
                   115                 120                 125
Asn Ser Cys Trp Ser Lys Asp Ala Glu Tyr Gly Leu Tyr Ser Ile Tyr
                   130                 135                 140
Gln Gly Gly Ile Phe Glu Leu Lys Glu Asn Asp Arg Ile Phe Val Ser
145                 150                 155                 160
Val Thr Asn Glu His Leu Ile Asp Met Asp His Glu Ala Ser Phe Phe
                   165                 170                 175
Gly Ala Phe Leu Val Gly Gly Ser Gly Ser Gly Asn Gly Ser Arg Val
                   180                 185                 190
Ala Ala His Ile Thr Gly Thr Arg Gly Arg Ser Asn Thr Leu Ser Ser
                   195                 200                 205
Pro Asn Ser Lys Asn Glu Lys Ala Leu Gly Arg Lys Ile Asn Ser Trp
                   210                 215                 220
Glu Ser Ser Arg Ser Gly His Ser Phe Leu Ser Asn Leu His Leu Arg
225                 230                 235                 240
Asn Gly Glu Leu Val Ile His Glu Lys Gly Phe Tyr Tyr Ile Tyr Ser
                   245                 250                 255
Gln Thr Tyr Phe Arg Phe Gln Glu Glu Ile Lys Glu Asn Thr Lys Asn
                   260                 265                 270
Asp Lys Gln Met Val Gln Tyr Ile Tyr Lys Tyr Thr Ser Tyr Pro Asp
                   275                 280                 285
Pro Ile Leu Leu Met Lys Ser Ala Arg Asn Ser Cys Trp Ser Lys Asp
                   290                 295                 300
Ala Glu Tyr Gly Leu Tyr Ser Ile Tyr Gln Gly Gly Ile Phe Glu Leu
305                 310                 315                 320
Lys Glu Asn Asp Arg Ile Phe Val Ser Val Thr Asn Glu His Leu Ile
                   325                 330                 335
Asp Met Asp His Glu Ala Ser Phe Phe Gly Ala Phe Leu Val Gly Gly
                   340                 345                 350
Ser Gly Ser Gly Asn Gly Ser Arg Val Ala Ala His Ile Thr Gly Thr
                   355                 360                 365
Arg Gly Arg Ser Asn Thr Leu Ser Ser Pro Asn Ser Lys Asn Glu Lys
370                 375                 380
Ala Leu Gly Arg Lys Ile Asn Ser Trp Glu Ser Ser Arg Ser Gly His
385                 390                 395                 400
Ser Phe Leu Ser Asn Leu His Leu Arg Asn Gly Glu Leu Val Ile His
                   405                 410                 415
Glu Lys Gly Phe Tyr Tyr Ile Tyr Ser Gln Thr Tyr Phe Arg Phe Gln
                   420                 425                 430
Glu Glu Ile Lys Glu Asn Thr Lys Asn Asp Lys Gln Met Val Gln Tyr
                   435                 440                 445
Ile Tyr Lys Tyr Thr Ser Tyr Pro Asp Pro Ile Leu Leu Met Lys Ser
                   450                 455                 460
Ala Arg Asn Ser Cys Trp Ser Lys Asp Ala Glu Tyr Gly Leu Tyr Ser
465                 470                 475                 480
Ile Tyr Gln Gly Gly Ile Phe Glu Leu Lys Glu Asn Asp Arg Ile Phe
                   485                 490                 495
```

Val Ser Val Thr Asn Glu His Leu Ile Asp Met Asp His Glu Ala Ser
            500                 505                 510

Phe Phe Gly Ala Phe Leu Val Gly Gly Pro Gly Ser Ser Ser Ser Ser
            515                 520                 525

Ser Ser Gly Ser Cys Asp Lys Thr His Thr Cys Pro Pro Cys Pro Ala
530                 535                 540

Pro Pro Val Ala Gly Pro Ser Val Phe Leu Phe Pro Pro Lys Pro Lys
545                 550                 555                 560

Asp Thr Leu Met Ile Ser Arg Thr Pro Glu Val Thr Cys Val Val Val
            565                 570                 575

Asp Val Ser His Glu Asp Pro Glu Val Lys Phe Asn Trp Tyr Val Asp
            580                 585                 590

Gly Val Glu Val His Asn Ala Lys Thr Lys Pro Arg Glu Glu Gln Tyr
            595                 600                 605

Asn Ser Thr Tyr Arg Val Val Ser Val Leu Thr Val Leu His Gln Asp
            610                 615                 620

Trp Leu Asn Gly Lys Glu Tyr Lys Cys Lys Val Ser Asn Lys Gly Leu
625                 630                 635                 640

Pro Ser Ser Ile Glu Lys Thr Ile Ser Lys Ala Lys Gly Gln Pro Arg
            645                 650                 655

Glu Pro Gln Val Tyr Thr Leu Pro Pro Ser Arg Glu Glu Met Thr Lys
            660                 665                 670

Asn Gln Val Ser Leu Thr Cys Leu Val Lys Gly Phe Tyr Pro Ser Asp
            675                 680                 685

Ile Ala Val Glu Trp Glu Ser Asn Gly Gln Pro Glu Asn Asn Tyr Lys
            690                 695                 700

Thr Thr Pro Pro Val Leu Asp Ser Asp Gly Ser Phe Phe Leu Tyr Ser
705                 710                 715                 720

Lys Leu Thr Val Asp Lys Ser Arg Trp Gln Gln Gly Asn Val Phe Ser
            725                 730                 735

Cys Ser Val Met His Glu Ala Leu His Asn His Tyr Thr Gln Lys Ser
            740                 745                 750

Leu Ser Leu Ser Pro Gly Lys
            755

<210> SEQ ID NO 19
<211> LENGTH: 740
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45

His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

-continued

```
Thr Lys Asn Asp Lys Gln Met Val Gln Tyr Ile Tyr Lys Tyr Thr Ser
                 85                  90                  95
Tyr Pro Asp Pro Ile Leu Leu Met Lys Ser Ala Arg Asn Ser Cys Trp
            100                 105                 110
Ser Lys Asp Ala Glu Tyr Gly Leu Tyr Ser Ile Tyr Gln Gly Gly Ile
        115                 120                 125
Phe Glu Leu Lys Glu Asn Asp Arg Ile Phe Val Ser Val Thr Asn Glu
    130                 135                 140
His Leu Ile Asp Met Asp His Glu Ala Ser Phe Phe Gly Ala Phe Leu
145                 150                 155                 160
Val Gly Gly Ser Gly Ser Gly Asn Gly Ser Arg Val Ala Ala His Ile
                165                 170                 175
Thr Gly Thr Arg Gly Arg Ser Asn Thr Leu Ser Ser Pro Asn Ser Lys
            180                 185                 190
Asn Glu Lys Ala Leu Gly Arg Lys Ile Asn Ser Trp Glu Ser Ser Arg
        195                 200                 205
Ser Gly His Ser Phe Leu Ser Asn Leu His Leu Arg Asn Gly Glu Leu
    210                 215                 220
Val Ile His Glu Lys Gly Phe Tyr Tyr Ile Tyr Ser Gln Thr Tyr Phe
225                 230                 235                 240
Arg Phe Gln Glu Glu Ile Lys Glu Asn Thr Lys Asn Asp Lys Gln Met
                245                 250                 255
Val Gln Tyr Ile Tyr Lys Tyr Thr Ser Tyr Pro Asp Pro Ile Leu Leu
            260                 265                 270
Met Lys Ser Ala Arg Asn Ser Cys Trp Ser Lys Asp Ala Glu Tyr Gly
        275                 280                 285
Leu Tyr Ser Ile Tyr Gln Gly Gly Ile Phe Glu Leu Lys Glu Asn Asp
    290                 295                 300
Arg Ile Phe Val Ser Val Thr Asn Glu His Leu Ile Asp Met Asp His
305                 310                 315                 320
Glu Ala Ser Phe Phe Gly Ala Phe Leu Val Gly Gly Ser Gly Ser Gly
                325                 330                 335
Asn Gly Ser Arg Val Ala Ala His Ile Thr Gly Thr Arg Gly Arg Ser
            340                 345                 350
Asn Thr Leu Ser Ser Pro Asn Ser Lys Asn Glu Lys Ala Leu Gly Arg
        355                 360                 365
Lys Ile Asn Ser Trp Glu Ser Ser Arg Ser Gly His Ser Phe Leu Ser
    370                 375                 380
Asn Leu His Leu Arg Asn Gly Glu Leu Val Ile His Glu Lys Gly Phe
385                 390                 395                 400
Tyr Tyr Ile Tyr Ser Gln Thr Tyr Phe Arg Phe Gln Glu Glu Ile Lys
                405                 410                 415
Glu Asn Thr Lys Asn Asp Lys Gln Met Val Gln Tyr Ile Tyr Lys Tyr
            420                 425                 430
Thr Ser Tyr Pro Asp Pro Ile Leu Leu Met Lys Ser Ala Arg Asn Ser
        435                 440                 445
Cys Trp Ser Lys Asp Ala Glu Tyr Gly Leu Tyr Ser Ile Tyr Gln Gly
    450                 455                 460
Gly Ile Phe Glu Leu Lys Glu Asn Asp Arg Ile Phe Val Ser Val Thr
465                 470                 475                 480
Asn Glu His Leu Ile Asp Met Asp His Glu Ala Ser Phe Phe Gly Ala
                485                 490                 495
Phe Leu Val Gly Gly Pro Gly Ser Ser Ser Ser Ser Ser Ser Gly Ser
```

```
                500                 505                 510
Cys Asp Lys Thr His Thr Cys Pro Pro Cys Pro Ala Pro Glu Leu Leu
            515                 520                 525

Gly Gly Pro Ser Val Phe Leu Phe Pro Pro Lys Pro Lys Asp Thr Leu
        530                 535                 540

Met Ile Ser Arg Thr Pro Glu Val Thr Cys Val Val Val Asp Val Ser
545                 550                 555                 560

His Glu Asp Pro Glu Val Lys Phe Asn Trp Tyr Val Asp Gly Val Glu
                565                 570                 575

Val His Asn Ala Lys Thr Lys Pro Arg Glu Glu Gln Tyr Ser Ser Thr
            580                 585                 590

Tyr Arg Val Val Ser Val Leu Thr Val Leu His Gln Asp Trp Leu Asn
        595                 600                 605

Gly Lys Glu Tyr Lys Cys Lys Val Ser Asn Lys Ala Leu Pro Ala Pro
    610                 615                 620

Ile Glu Lys Thr Ile Ser Lys Ala Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Val Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 20
<211> LENGTH: 754
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45

His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110
```

-continued

Ser Lys Asp Ala Glu Tyr Gly Leu Tyr Ser Ile Tyr Gln Gly Gly Ile
            115                 120                 125

Phe Glu Leu Lys Glu Asn Asp Arg Ile Phe Val Ser Val Thr Asn Glu
130                 135                 140

His Leu Ile Asp Met Asp His Glu Ala Ser Phe Phe Gly Ala Phe Leu
145                 150                 155                 160

Val Gly Gly Ser Gly Ser Gly Asn Gly Ser Arg Val Ala Ala His Ile
            165                 170                 175

Thr Gly Thr Arg Gly Arg Ser Asn Thr Leu Ser Ser Pro Asn Ser Lys
            180                 185                 190

Asn Glu Lys Ala Leu Gly Arg Lys Ile Asn Ser Trp Glu Ser Ser Arg
            195                 200                 205

Ser Gly His Ser Phe Leu Ser Asn Leu His Leu Arg Asn Gly Glu Leu
            210                 215                 220

Val Ile His Glu Lys Gly Phe Tyr Ile Tyr Ser Gln Thr Tyr Phe
225                 230                 235                 240

Arg Phe Gln Glu Glu Ile Lys Glu Asn Thr Lys Asn Asp Lys Gln Met
                245                 250                 255

Val Gln Tyr Ile Tyr Lys Tyr Thr Ser Tyr Pro Asp Pro Ile Leu Leu
            260                 265                 270

Met Lys Ser Ala Arg Asn Ser Cys Trp Ser Lys Asp Ala Glu Tyr Gly
            275                 280                 285

Leu Tyr Ser Ile Tyr Gln Gly Gly Ile Phe Glu Leu Lys Glu Asn Asp
            290                 295                 300

Arg Ile Phe Val Ser Val Thr Asn Glu His Leu Ile Asp Met Asp His
305                 310                 315                 320

Glu Ala Ser Phe Phe Gly Ala Phe Leu Val Gly Gly Ser Gly Ser Gly
                325                 330                 335

Asn Gly Ser Arg Val Ala Ala His Ile Thr Gly Thr Arg Gly Arg Ser
            340                 345                 350

Asn Thr Leu Ser Ser Pro Asn Ser Lys Asn Glu Lys Ala Leu Gly Arg
            355                 360                 365

Lys Ile Asn Ser Trp Glu Ser Ser Arg Ser Gly His Ser Phe Leu Ser
370                 375                 380

Asn Leu His Leu Arg Asn Gly Glu Leu Val Ile His Glu Lys Gly Phe
385                 390                 395                 400

Tyr Tyr Ile Tyr Ser Gln Thr Tyr Phe Arg Phe Gln Glu Glu Ile Lys
                405                 410                 415

Glu Asn Thr Lys Asn Asp Lys Gln Met Val Gln Tyr Ile Tyr Lys Tyr
            420                 425                 430

Thr Ser Tyr Pro Asp Pro Ile Leu Leu Met Lys Ser Ala Arg Asn Ser
            435                 440                 445

Cys Trp Ser Lys Asp Ala Glu Tyr Gly Leu Tyr Ser Ile Tyr Gln Gly
            450                 455                 460

Gly Ile Phe Glu Leu Lys Glu Asn Asp Arg Ile Phe Val Ser Val Thr
465                 470                 475                 480

Asn Glu His Leu Ile Asp Met Asp His Glu Ala Ser Phe Phe Gly Ala
                485                 490                 495

Phe Leu Val Gly Gly Pro Gly Ser Ser Ser Ser Ser Ser Gly Ser
            500                 505                 510

Cys Asp Lys Thr His Thr Cys Pro Pro Cys Pro Ala Pro Glu Leu Leu
            515                 520                 525

```
Gly Gly Pro Ser Val Phe Leu Phe Pro Pro Lys Pro Lys Asp Thr Leu
            530                 535                 540

Met Ile Ser Arg Thr Pro Glu Val Thr Cys Val Val Val Asp Val Ser
545                 550                 555                 560

His Glu Asp Pro Glu Val Lys Phe Asn Trp Tyr Val Asp Gly Val Glu
                565                 570                 575

Val His Asn Ala Lys Thr Lys Pro Arg Glu Glu Gln Tyr Ser Ser Thr
            580                 585                 590

Tyr Arg Val Val Ser Val Leu Thr Val Leu His Gln Asp Trp Leu Asn
        595                 600                 605

Gly Lys Glu Tyr Lys Cys Lys Val Ser Asn Lys Ala Leu Pro Ala Pro
    610                 615                 620

Ile Glu Lys Thr Ile Ser Lys Ala Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Val Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Ser Ser Ser Ser Ser Ala Trp Ser His Pro Gln Phe
            740                 745                 750

Glu Lys

<210> SEQ ID NO 21
<211> LENGTH: 739
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45

His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125
```

```
Phe Glu Leu Lys Glu Asn Asp Arg Ile Phe Val Ser Val Thr Asn Glu
    130                 135                 140

His Leu Ile Asp Met Asp His Glu Ala Ser Phe Phe Gly Ala Phe Leu
145                 150                 155                 160

Val Gly Gly Ser Gly Ser Gly Asn Gly Ser Arg Val Ala Ala His Ile
            165                 170                 175

Thr Gly Thr Arg Gly Arg Ser Asn Thr Leu Ser Ser Pro Asn Ser Lys
                180                 185                 190

Asn Glu Lys Ala Leu Gly Arg Lys Ile Asn Ser Trp Glu Ser Ser Arg
        195                 200                 205

Ser Gly His Ser Phe Leu Ser Asn Leu His Leu Arg Asn Gly Glu Leu
    210                 215                 220

Val Ile His Glu Lys Gly Phe Tyr Tyr Ile Tyr Ser Gln Thr Tyr Phe
225                 230                 235                 240

Arg Phe Gln Glu Glu Ile Lys Glu Asn Thr Lys Asn Asp Lys Gln Met
                245                 250                 255

Val Gln Tyr Ile Tyr Lys Tyr Thr Ser Tyr Pro Asp Pro Ile Leu Leu
            260                 265                 270

Met Lys Ser Ala Arg Asn Ser Cys Trp Ser Lys Asp Ala Glu Tyr Gly
        275                 280                 285

Leu Tyr Ser Ile Tyr Gln Gly Gly Ile Phe Glu Leu Lys Glu Asn Asp
    290                 295                 300

Arg Ile Phe Val Ser Val Thr Asn Glu His Leu Ile Asp Met Asp His
305                 310                 315                 320

Glu Ala Ser Phe Phe Gly Ala Phe Leu Val Gly Gly Ser Gly Ser Gly
                325                 330                 335

Asn Gly Ser Arg Val Ala Ala His Ile Thr Gly Thr Arg Gly Arg Ser
            340                 345                 350

Asn Thr Leu Ser Ser Pro Asn Ser Lys Asn Glu Lys Ala Leu Gly Arg
        355                 360                 365

Lys Ile Asn Ser Trp Glu Ser Ser Arg Ser Gly His Ser Phe Leu Ser
    370                 375                 380

Asn Leu His Leu Arg Asn Gly Glu Leu Val Ile His Glu Lys Gly Phe
385                 390                 395                 400

Tyr Tyr Ile Tyr Ser Gln Thr Tyr Phe Arg Phe Gln Glu Glu Ile Lys
                405                 410                 415

Glu Asn Thr Lys Asn Asp Lys Gln Met Val Gln Tyr Ile Tyr Lys Tyr
            420                 425                 430

Thr Ser Tyr Pro Asp Pro Ile Leu Leu Met Lys Ser Ala Arg Asn Ser
        435                 440                 445

Cys Trp Ser Lys Asp Ala Glu Tyr Gly Leu Tyr Ser Ile Tyr Gln Gly
    450                 455                 460

Gly Ile Phe Glu Leu Lys Glu Asn Asp Arg Ile Phe Val Ser Val Thr
465                 470                 475                 480

Asn Glu His Leu Ile Asp Met Asp His Glu Ala Ser Phe Phe Gly Ala
                485                 490                 495

Phe Leu Val Gly Gly Pro Gly Ser Ser Ser Ser Ser Ser Ser Gly Ser
            500                 505                 510

Cys Asp Lys Thr His Thr Cys Pro Cys Pro Ala Pro Pro Val Ala
        515                 520                 525

Gly Pro Ser Val Phe Leu Phe Pro Pro Lys Pro Lys Asp Thr Leu Met
530                 535                 540
```

```
Ile Ser Arg Thr Pro Glu Val Thr Cys Val Val Val Asp Val Ser His
545                 550                 555                 560

Glu Asp Pro Glu Val Lys Phe Asn Trp Tyr Val Asp Gly Val Glu Val
            565                 570                 575

His Asn Ala Lys Thr Lys Pro Arg Glu Glu Gln Tyr Asn Ser Thr Tyr
        580                 585                 590

Arg Val Val Ser Val Leu Thr Val Leu His Gln Asp Trp Leu Asn Gly
    595                 600                 605

Lys Glu Tyr Lys Cys Lys Val Ser Asn Lys Gly Leu Pro Ser Ser Ile
610                 615                 620

Glu Lys Thr Ile Ser Lys Ala Lys Gly Gln Pro Arg Glu Pro Gln Val
625                 630                 635                 640

Tyr Thr Leu Pro Pro Ser Arg Glu Glu Met Thr Lys Asn Gln Val Ser
            645                 650                 655

Leu Thr Cys Leu Val Lys Gly Phe Tyr Pro Ser Asp Ile Ala Val Glu
        660                 665                 670

Trp Glu Ser Asn Gly Gln Pro Glu Asn Asn Tyr Lys Thr Thr Pro Pro
    675                 680                 685

Val Leu Asp Ser Asp Gly Ser Phe Phe Leu Tyr Ser Lys Leu Thr Val
690                 695                 700

Asp Lys Ser Arg Trp Gln Gln Gly Asn Val Phe Ser Cys Ser Val Met
705                 710                 715                 720

His Glu Ala Leu His Asn His Tyr Thr Gln Lys Ser Leu Ser Leu Ser
            725                 730                 735

Pro Gly Lys

<210> SEQ ID NO 22
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Ser Gly Ser Gly Ser
1               5

<210> SEQ ID NO 23
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gly Ser Gly Ser
1

<210> SEQ ID NO 24
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24
```

Gly Ser Gly
1

<210> SEQ ID NO 25
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 25

Gly Pro Gly Ser Ser Ser Ser Ser Gly Ser Cys Asp Lys Thr His
1               5                   10                  15

Thr Cys Pro Pro Cys
            20

<210> SEQ ID NO 26
<211> LENGTH: 751
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45

His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
    130                 135                 140

His Leu Ile Asp Met Asp His Glu Ala Ser Phe Phe Gly Ala Phe Leu
145                 150                 155                 160

Val Gly Gly Ser Gly Ser Gly Asn Gly Ser Arg Val Ala Ala His Ile
                165                 170                 175

Thr Gly Thr Arg Gly Arg Ser Asn Thr Leu Ser Ser Pro Asn Ser Lys
            180                 185                 190

Asn Glu Lys Ala Leu Gly Arg Lys Ile Asn Ser Trp Glu Ser Ser Arg
        195                 200                 205

Ser Gly His Ser Phe Leu Ser Asn Leu His Leu Arg Asn Gly Glu Leu
    210                 215                 220

Val Ile His Glu Lys Gly Phe Tyr Tyr Ile Tyr Ser Gln Thr Tyr Phe
225                 230                 235                 240

-continued

```
Arg Phe Gln Glu Glu Ile Lys Glu Asn Thr Lys Asn Asp Lys Gln Met
                245                 250                 255
Val Gln Tyr Ile Tyr Lys Tyr Thr Ser Tyr Pro Asp Pro Ile Leu Leu
            260                 265                 270
Met Lys Ser Ala Arg Asn Ser Cys Trp Ser Lys Asp Ala Glu Tyr Gly
        275                 280                 285
Leu Tyr Ser Ile Tyr Gln Gly Gly Ile Phe Glu Leu Lys Glu Asn Asp
    290                 295                 300
Arg Ile Phe Val Ser Val Thr Asn Glu His Leu Ile Asp Met Asp His
305                 310                 315                 320
Glu Ala Ser Phe Phe Gly Ala Phe Leu Val Gly Gly Ser Gly Ser Gly
                325                 330                 335
Asn Gly Ser Arg Val Ala Ala His Ile Thr Gly Thr Arg Gly Arg Ser
            340                 345                 350
Asn Thr Leu Ser Ser Pro Asn Ser Lys Asn Glu Lys Ala Leu Gly Arg
        355                 360                 365
Lys Ile Asn Ser Trp Glu Ser Ser Arg Ser Gly His Ser Phe Leu Ser
    370                 375                 380
Asn Leu His Leu Arg Asn Gly Glu Leu Val Ile His Glu Lys Gly Phe
385                 390                 395                 400
Tyr Tyr Ile Tyr Ser Gln Thr Tyr Phe Arg Phe Gln Glu Glu Ile Lys
                405                 410                 415
Glu Asn Thr Lys Asn Asp Lys Gln Met Val Gln Tyr Ile Tyr Lys Tyr
            420                 425                 430
Thr Ser Tyr Pro Asp Pro Ile Leu Leu Met Lys Ser Ala Arg Asn Ser
        435                 440                 445
Cys Trp Ser Lys Asp Ala Glu Tyr Gly Leu Tyr Ser Ile Tyr Gln Gly
    450                 455                 460
Gly Ile Phe Glu Leu Lys Glu Asn Asp Arg Ile Phe Val Ser Val Thr
465                 470                 475                 480
Asn Glu His Leu Ile Asp Met Asp His Glu Ala Ser Phe Phe Gly Ala
                485                 490                 495
Phe Leu Val Gly Gly Pro Gly Ser Ser Ser Ser Ser Gly Ser Asp
            500                 505                 510
Lys Thr His Thr Cys Pro Pro Cys Pro Ala Pro Val Ala Gly Pro
    515                 520                 525
Ser Val Phe Leu Phe Pro Pro Lys Pro Lys Asp Thr Leu Met Ile Ser
    530                 535                 540
Arg Thr Pro Glu Val Thr Cys Val Val Val Asp Val Ser His Glu Asp
545                 550                 555                 560
Pro Glu Val Lys Phe Asn Trp Tyr Val Asp Gly Val Glu Val His Asn
                565                 570                 575
Ala Lys Thr Lys Pro Arg Glu Glu Gln Tyr Asn Ser Thr Tyr Arg Val
            580                 585                 590
Val Ser Val Leu Thr Val Leu His Gln Asp Trp Leu Asn Gly Lys Glu
        595                 600                 605
Tyr Lys Cys Lys Val Ser Asn Lys Gly Leu Pro Ser Ser Ile Glu Lys
    610                 615                 620
Thr Ile Ser Lys Ala Lys Gly Gln Pro Arg Glu Pro Gln Val Tyr Thr
625                 630                 635                 640
Leu Pro Pro Ser Arg Glu Glu Met Thr Lys Asn Gln Val Ser Leu Thr
                645                 650                 655
Cys Leu Val Lys Gly Phe Tyr Pro Ser Asp Ile Ala Val Glu Trp Glu
```

```
            660                 665                 670
Ser Asn Gly Gln Pro Glu Asn Asn Tyr Lys Thr Thr Pro Pro Val Leu
                675                 680                 685

Asp Ser Asp Gly Ser Phe Phe Leu Tyr Ser Lys Leu Thr Val Asp Lys
            690                 695                 700

Ser Arg Trp Gln Gln Gly Asn Val Phe Ser Cys Ser Val Met His Glu
705                 710                 715                 720

Ala Leu His Asn His Tyr Thr Gln Lys Ser Leu Ser Leu Ser Pro Gly
                725                 730                 735

Ser Ser Ser Ser Ser Ser Ala Trp Ser His Pro Gln Phe Glu Lys
                740                 745                 750

<210> SEQ ID NO 27
<211> LENGTH: 750
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
                20                  25                  30

Asn Ser Trp Glu Ser Ser Arg Ser Gly His Ser Phe Leu Ser Asn Leu
            35                  40                  45

His Leu Arg Asn Gly Glu Leu Val Ile His Glu Lys Gly Phe Tyr Tyr
        50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
    130                 135                 140

His Leu Ile Asp Met Asp His Glu Ala Ser Phe Phe Gly Ala Phe Leu
145                 150                 155                 160

Val Gly Gly Ser Gly Ser Gly Asn Gly Ser Arg Val Ala Ala His Ile
                165                 170                 175

Thr Gly Thr Arg Gly Arg Ser Asn Thr Leu Ser Ser Pro Asn Ser Lys
            180                 185                 190

Asn Glu Lys Ala Leu Gly Arg Lys Ile Asn Ser Trp Glu Ser Ser Arg
        195                 200                 205

Ser Gly His Ser Phe Leu Ser Asn Leu His Leu Arg Asn Gly Glu Leu
    210                 215                 220

Val Ile His Glu Lys Gly Phe Tyr Tyr Ile Tyr Ser Gln Thr Tyr Phe
225                 230                 235                 240

Arg Phe Gln Glu Glu Ile Lys Glu Asn Thr Lys Asn Asp Lys Gln Met
                245                 250                 255

Val Gln Tyr Ile Tyr Lys Tyr Thr Ser Tyr Pro Asp Pro Ile Leu Leu
            260                 265                 270
```

```
Met Lys Ser Ala Arg Asn Ser Cys Trp Ser Lys Asp Ala Glu Tyr Gly
        275                 280                 285

Leu Tyr Ser Ile Tyr Gln Gly Gly Ile Phe Glu Leu Lys Glu Asn Asp
        290                 295                 300

Arg Ile Phe Val Ser Val Thr Asn Glu His Leu Ile Asp Met Asp His
305                 310                 315                 320

Glu Ala Ser Phe Phe Gly Ala Phe Leu Val Gly Gly Ser Gly Ser Arg
                325                 330                 335

Val Ala Ala His Ile Thr Gly Thr Arg Gly Arg Ser Asn Thr Leu Ser
                340                 345                 350

Ser Pro Asn Ser Lys Asn Glu Lys Ala Leu Gly Arg Lys Ile Asn Ser
            355                 360                 365

Trp Glu Ser Ser Arg Ser Gly His Ser Phe Leu Ser Asn Leu His Leu
        370                 375                 380

Arg Asn Gly Glu Leu Val Ile His Glu Lys Gly Phe Tyr Tyr Ile Tyr
385                 390                 395                 400

Ser Gln Thr Tyr Phe Arg Phe Gln Glu Glu Ile Lys Glu Asn Thr Lys
                405                 410                 415

Asn Asp Lys Gln Met Val Gln Tyr Ile Tyr Lys Tyr Thr Ser Tyr Pro
            420                 425                 430

Asp Pro Ile Leu Leu Met Lys Ser Ala Arg Asn Ser Cys Trp Ser Lys
        435                 440                 445

Asp Ala Glu Tyr Gly Leu Tyr Ser Ile Tyr Gln Gly Gly Ile Phe Glu
    450                 455                 460

Leu Lys Glu Asn Asp Arg Ile Phe Val Ser Val Thr Asn Glu His Leu
465                 470                 475                 480

Ile Asp Met Asp His Glu Ala Ser Phe Phe Gly Ala Phe Leu Val Gly
                485                 490                 495

Gly Pro Gly Ser Ser Ser Ser Ser Ser Gly Ser Cys Asp Lys Thr
            500                 505                 510

His Thr Cys Pro Pro Cys Pro Ala Pro Glu Leu Leu Gly Gly Pro Ser
        515                 520                 525

Val Phe Leu Phe Pro Pro Lys Pro Lys Asp Thr Leu Met Ile Ser Arg
        530                 535                 540

Thr Pro Glu Val Thr Cys Val Val Val Asp Val Ser His Glu Asp Pro
545                 550                 555                 560

Glu Val Lys Phe Asn Trp Tyr Val Asp Gly Val Glu Val His Asn Ala
                565                 570                 575

Lys Thr Lys Pro Arg Glu Glu Gln Tyr Ser Ser Thr Tyr Arg Val Val
            580                 585                 590

Ser Val Leu Thr Val Leu His Gln Asp Trp Leu Asn Gly Lys Glu Tyr
        595                 600                 605

Lys Cys Lys Val Ser Asn Lys Ala Leu Pro Ala Pro Ile Glu Lys Thr
    610                 615                 620

Ile Ser Lys Ala Lys Gly Gln Pro Arg Glu Pro Gln Val Tyr Thr Leu
625                 630                 635                 640

Pro Pro Ser Arg Glu Glu Met Thr Lys Asn Gln Val Ser Leu Thr Cys
                645                 650                 655

Leu Val Lys Gly Phe Tyr Pro Ser Asp Ile Ala Val Glu Trp Glu Ser
            660                 665                 670

Asn Gly Gln Pro Glu Asn Asn Tyr Lys Thr Thr Pro Pro Val Leu Asp
        675                 680                 685
```

```
Ser Asp Gly Ser Phe Phe Leu Tyr Ser Lys Leu Thr Val Asp Lys Ser
    690                 695                 700

Arg Trp Gln Gln Gly Asn Val Phe Ser Cys Ser Val Met His Glu Ala
705                 710                 715                 720

Leu His Asn His Tyr Thr Gln Lys Ser Leu Ser Leu Ser Pro Gly Ser
                725                 730                 735

Ser Ser Ser Ser Ser Ala Trp Ser His Pro Gln Phe Glu Lys
                740                 745                 750

<210> SEQ ID NO 28
<211> LENGTH: 750
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
                20                  25                  30

Asn Ser Trp Glu Ser Ser Arg Ser Gly His Ser Phe Leu Ser Asn Leu
            35                  40                  45

His Leu Arg Asn Gly Glu Leu Val Ile His Glu Lys Gly Phe Tyr Tyr
50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
130                 135                 140

His Leu Ile Asp Met Asp His Glu Ala Ser Phe Phe Gly Ala Phe Leu
145                 150                 155                 160

Val Gly Gly Ser Gly Ser Gly Ser Arg Val Ala Ala His Ile Thr Gly
                165                 170                 175

Thr Arg Gly Arg Ser Asn Thr Leu Ser Ser Pro Asn Ser Lys Asn Glu
            180                 185                 190

Lys Ala Leu Gly Arg Lys Ile Asn Ser Trp Glu Ser Ser Arg Ser Gly
        195                 200                 205

His Ser Phe Leu Ser Asn Leu His Leu Arg Asn Gly Glu Leu Val Ile
    210                 215                 220

His Glu Lys Gly Phe Tyr Tyr Ile Tyr Ser Gln Thr Tyr Phe Arg Phe
225                 230                 235                 240

Gln Glu Glu Ile Lys Glu Asn Thr Lys Asn Asp Lys Gln Met Val Gln
                245                 250                 255

Tyr Ile Tyr Lys Tyr Thr Ser Tyr Pro Asp Pro Ile Leu Leu Met Lys
            260                 265                 270

Ser Ala Arg Asn Ser Cys Trp Ser Lys Asp Ala Glu Tyr Gly Leu Tyr
        275                 280                 285

Ser Ile Tyr Gln Gly Gly Ile Phe Glu Leu Lys Glu Asn Asp Arg Ile
```

```
                290                 295                 300
Phe Val Ser Val Thr Asn Glu His Leu Ile Asp Met Asp His Glu Ala
305                 310                 315                 320
Ser Phe Phe Gly Ala Phe Leu Val Gly Gly Ser Gly Ser Gly Ser Arg
                325                 330                 335
Val Ala Ala His Ile Thr Gly Thr Arg Gly Arg Ser Asn Thr Leu Ser
                340                 345                 350
Ser Pro Asn Ser Lys Asn Glu Lys Ala Leu Gly Arg Lys Ile Asn Ser
                355                 360                 365
Trp Glu Ser Ser Arg Ser Gly His Ser Phe Leu Ser Asn Leu His Leu
                370                 375                 380
Arg Asn Gly Glu Leu Val Ile His Glu Lys Gly Phe Tyr Tyr Ile Tyr
385                 390                 395                 400
Ser Gln Thr Tyr Phe Arg Phe Gln Glu Glu Ile Lys Glu Asn Thr Lys
                405                 410                 415
Asn Asp Lys Gln Met Val Gln Tyr Ile Tyr Lys Tyr Thr Ser Tyr Pro
                420                 425                 430
Asp Pro Ile Leu Leu Met Lys Ser Ala Arg Asn Ser Cys Trp Ser Lys
                435                 440                 445
Asp Ala Glu Tyr Gly Leu Tyr Ser Ile Tyr Gln Gly Gly Ile Phe Glu
                450                 455                 460
Leu Lys Glu Asn Asp Arg Ile Phe Val Ser Val Thr Asn Glu His Leu
465                 470                 475                 480
Ile Asp Met Asp His Glu Ala Ser Phe Phe Gly Ala Phe Leu Val Gly
                485                 490                 495
Gly Pro Gly Ser Ser Ser Ser Ser Ser Gly Ser Cys Asp Lys Thr
                500                 505                 510
His Thr Cys Pro Pro Cys Pro Ala Pro Glu Leu Leu Gly Gly Pro Ser
                515                 520                 525
Val Phe Leu Phe Pro Pro Lys Pro Lys Asp Thr Leu Met Ile Ser Arg
                530                 535                 540
Thr Pro Glu Val Thr Cys Val Val Val Asp Val Ser His Glu Asp Pro
545                 550                 555                 560
Glu Val Lys Phe Asn Trp Tyr Val Asp Gly Val Glu Val His Asn Ala
                565                 570                 575
Lys Thr Lys Pro Arg Glu Glu Gln Tyr Ser Ser Thr Tyr Arg Val Val
                580                 585                 590
Ser Val Leu Thr Val Leu His Gln Asp Trp Leu Asn Gly Lys Glu Tyr
                595                 600                 605
Lys Cys Lys Val Ser Asn Lys Ala Leu Pro Ala Pro Ile Glu Lys Thr
                610                 615                 620
Ile Ser Lys Ala Lys Gly Gln Pro Arg Glu Pro Gln Val Tyr Thr Leu
625                 630                 635                 640
Pro Pro Ser Arg Glu Glu Met Thr Lys Asn Gln Val Ser Leu Thr Cys
                645                 650                 655
Leu Val Lys Gly Phe Tyr Pro Ser Asp Ile Ala Val Glu Trp Glu Ser
                660                 665                 670
Asn Gly Gln Pro Glu Asn Asn Tyr Lys Thr Thr Pro Pro Val Leu Asp
                675                 680                 685
Ser Asp Gly Ser Phe Phe Leu Tyr Ser Lys Leu Thr Val Asp Lys Ser
                690                 695                 700
Arg Trp Gln Gln Gly Asn Val Phe Ser Cys Ser Val Met His Glu Ala
705                 710                 715                 720
```

-continued

```
Leu His Asn His Tyr Thr Gln Lys Ser Leu Ser Leu Ser Pro Gly Ser
            725                 730                 735

Ser Ser Ser Ser Ser Ala Trp Ser His Pro Gln Phe Glu Lys
        740                 745                 750

<210> SEQ ID NO 29
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45

His Leu Arg Asn Gly Glu Leu Val Ile His Glu Lys Gly Phe Tyr Tyr
50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
            85                  90                  95

Tyr Pro Asp Pro Ile Leu Leu Met Lys Ser Ala Arg Asn Ser Cys Trp
        100                 105                 110

Ser Lys Asp Ala Glu Tyr Gly Leu Tyr Ser Ile Tyr Gln Gly Gly Ile
    115                 120                 125

Phe Glu Leu Lys Glu Asn Asp Arg Ile Phe Val Ser Val Thr Asn Glu
130                 135                 140

His Leu Ile Asp Met Asp His Glu Ala Ser Phe Phe Gly Ala Phe Leu
145                 150                 155                 160

Val Gly Gly Ser Gly Ser Gly Asn Gly Ser Arg Val Ala Ala His Ile
                165                 170                 175

Thr Gly Thr Arg Gly Arg Ser Asn Thr Leu Ser Ser Pro Asn Ser Lys
            180                 185                 190

Asn Glu Lys Ala Leu Gly Arg Lys Ile Asn Ser Trp Glu Ser Ser Arg
        195                 200                 205

Ser Gly His Ser Phe Leu Ser Asn Leu His Leu Arg Asn Gly Glu Leu
    210                 215                 220

Val Ile His Glu Lys Gly Phe Tyr Tyr Ile Tyr Ser Gln Thr Tyr Phe
225                 230                 235                 240

Arg Phe Gln Glu Glu Ile Lys Glu Asn Thr Lys Asn Asp Lys Gln Met
                245                 250                 255

Val Gln Tyr Ile Tyr Lys Tyr Thr Ser Tyr Pro Asp Pro Ile Leu Leu
            260                 265                 270

Met Lys Ser Ala Arg Asn Ser Cys Trp Ser Lys Asp Ala Glu Tyr Gly
        275                 280                 285

Leu Tyr Ser Ile Tyr Gln Gly Gly Ile Phe Glu Leu Lys Glu Asn Asp
    290                 295                 300

Arg Ile Phe Val Ser Val Thr Asn Glu His Leu Ile Asp Met Asp His
305                 310                 315                 320
```

-continued

Glu Ala Ser Phe Phe Gly Ala Phe Leu Val Gly Gly Ser Gly Ser Arg
            325                 330                 335

Val Ala Ala His Ile Thr Gly Thr Arg Gly Arg Ser Asn Thr Leu Ser
            340                 345                 350

Ser Pro Asn Ser Lys Asn Glu Lys Ala Leu Gly Arg Lys Ile Asn Ser
            355                 360                 365

Trp Glu Ser Ser Arg Ser Gly His Ser Phe Leu Ser Asn Leu His Leu
            370                 375                 380

Arg Asn Gly Glu Leu Val Ile His Glu Lys Gly Phe Tyr Tyr Ile Tyr
385                 390                 395                 400

Ser Gln Thr Tyr Phe Arg Phe Gln Glu Glu Ile Lys Glu Asn Thr Lys
            405                 410                 415

Asn Asp Lys Gln Met Val Gln Tyr Ile Tyr Lys Tyr Thr Ser Tyr Pro
            420                 425                 430

Asp Pro Ile Leu Leu Met Lys Ser Ala Arg Asn Ser Cys Trp Ser Lys
            435                 440                 445

Asp Ala Glu Tyr Gly Leu Tyr Ser Ile Tyr Gln Gly Gly Ile Phe Glu
            450                 455                 460

Leu Lys Glu Asn Asp Arg Ile Phe Val Ser Val Thr Asn Glu His Leu
465                 470                 475                 480

Ile Asp Met Asp His Glu Ala Ser Phe Phe Gly Ala Phe Leu Val Gly
            485                 490                 495

Gly Pro Gly Ser Ser Ser Ser Ser Ser Gly Ser Cys Asp Lys Thr
            500                 505                 510

His Thr Cys Pro Pro Cys Pro Ala Pro Glu Leu Leu Gly Gly Pro Ser
            515                 520                 525

Val Phe Leu Phe Pro Pro Lys Pro Lys Asp Thr Leu Met Ile Ser Arg
            530                 535                 540

Thr Pro Glu Val Thr Cys Val Val Asp Val Ser His Glu Asp Pro
545                 550                 555                 560

Glu Val Lys Phe Asn Trp Tyr Val Asp Gly Val Glu Val His Asn Ala
            565                 570                 575

Lys Thr Lys Pro Arg Glu Glu Gln Tyr Ser Ser Thr Tyr Arg Val Val
            580                 585                 590

Ser Val Leu Thr Val Leu His Gln Asp Trp Leu Asn Gly Lys Glu Tyr
            595                 600                 605

Lys Cys Lys Val Ser Asn Lys Ala Leu Pro Ala Pro Ile Glu Lys Thr
            610                 615                 620

Ile Ser Lys Ala Lys Gly Gln Pro Arg Glu Pro Gln Val Tyr Thr Leu
625                 630                 635                 640

Pro Pro Ser Arg Glu Glu Met Thr Lys Asn Gln Val Ser Leu Thr Cys
            645                 650                 655

Leu Val Lys Gly Phe Tyr Pro Ser Asp Ile Ala Val Glu Trp Glu Ser
            660                 665                 670

Asn Gly Gln Pro Glu Asn Asn Tyr Lys Thr Thr Pro Pro Val Leu Asp
            675                 680                 685

Ser Asp Gly Ser Phe Phe Leu Tyr Ser Lys Leu Thr Val Asp Lys Ser
            690                 695                 700

Arg Trp Gln Gln Gly Asn Val Phe Ser Cys Ser Val Met His Glu Ala
705                 710                 715                 720

Leu His Asn His Tyr Thr Gln Lys Ser Leu Ser Leu Ser Pro Gly Lys
            725                 730                 735

```
<210> SEQ ID NO 30
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30
```

| | | | | | | | | | | | | | | | |
|---|---|---|---|---|---|---|---|---|---|---|---|---|---|---|---|
| Gln | Arg | Val | Ala | Ala | His | Ile | Thr | Gly | Thr | Arg | Gly | Arg | Ser | Asn | Thr |
| 1 | | | | 5 | | | | | 10 | | | | | 15 | |
| Leu | Ser | Ser | Pro | Asn | Ser | Lys | Asn | Glu | Lys | Ala | Leu | Gly | Arg | Lys | Ile |
| | | | 20 | | | | | 25 | | | | | 30 | | |
| Asn | Ser | Trp | Glu | Ser | Ser | Arg | Ser | Gly | His | Ser | Phe | Leu | Ser | Asn | Leu |
| | | | 35 | | | | 40 | | | | | 45 | | | |
| His | Leu | Arg | Asn | Gly | Glu | Leu | Val | Ile | His | Glu | Lys | Gly | Phe | Tyr | Tyr |
| | 50 | | | | | 55 | | | | | 60 | | | | |
| Ile | Tyr | Ser | Gln | Thr | Tyr | Phe | Arg | Phe | Gln | Glu | Glu | Ile | Lys | Glu | Asn |
| 65 | | | | | 70 | | | | | 75 | | | | | 80 |
| Thr | Lys | Asn | Asp | Lys | Gln | Met | Val | Gln | Tyr | Ile | Tyr | Lys | Tyr | Thr | Ser |
| | | | | 85 | | | | | 90 | | | | | 95 | |
| Tyr | Pro | Asp | Pro | Ile | Leu | Leu | Met | Lys | Ser | Ala | Arg | Asn | Ser | Cys | Trp |
| | | | 100 | | | | | 105 | | | | | 110 | | |
| Ser | Lys | Asp | Ala | Glu | Tyr | Gly | Leu | Tyr | Ser | Ile | Tyr | Gln | Gly | Gly | Ile |
| | | | 115 | | | | | 120 | | | | | 125 | | |
| Phe | Glu | Leu | Lys | Glu | Asn | Asp | Arg | Ile | Phe | Val | Ser | Val | Thr | Asn | Glu |
| | 130 | | | | | 135 | | | | | 140 | | | | |
| His | Leu | Ile | Asp | Met | Asp | His | Glu | Ala | Ser | Phe | Phe | Gly | Ala | Phe | Leu |
| 145 | | | | | 150 | | | | | 155 | | | | | 160 |
| Val | Gly | Gly | Ser | Gly | Ser | Gly | Ser | Arg | Val | Ala | Ala | His | Ile | Thr | Gly |
| | | | | 165 | | | | | 170 | | | | | 175 | |
| Thr | Arg | Gly | Arg | Ser | Asn | Thr | Leu | Ser | Ser | Pro | Asn | Ser | Lys | Asn | Glu |
| | | | 180 | | | | | 185 | | | | | 190 | | |
| Lys | Ala | Leu | Gly | Arg | Lys | Ile | Asn | Ser | Trp | Glu | Ser | Ser | Arg | Ser | Gly |
| | | | 195 | | | | | 200 | | | | | 205 | | |
| His | Ser | Phe | Leu | Ser | Asn | Leu | His | Leu | Arg | Asn | Gly | Glu | Leu | Val | Ile |
| | 210 | | | | | 215 | | | | | 220 | | | | |
| His | Glu | Lys | Gly | Phe | Tyr | Tyr | Ile | Tyr | Ser | Gln | Thr | Tyr | Phe | Arg | Phe |
| 225 | | | | | 230 | | | | | 235 | | | | | 240 |
| Gln | Glu | Glu | Ile | Lys | Glu | Asn | Thr | Lys | Asn | Asp | Lys | Gln | Met | Val | Gln |
| | | | | 245 | | | | | 250 | | | | | 255 | |
| Tyr | Ile | Tyr | Lys | Tyr | Thr | Ser | Tyr | Pro | Asp | Pro | Ile | Leu | Leu | Met | Lys |
| | | | 260 | | | | | 265 | | | | | 270 | | |
| Ser | Ala | Arg | Asn | Ser | Cys | Trp | Ser | Lys | Asp | Ala | Glu | Tyr | Gly | Leu | Tyr |
| | | | 275 | | | | | 280 | | | | | 285 | | |
| Ser | Ile | Tyr | Gln | Gly | Gly | Ile | Phe | Glu | Leu | Lys | Glu | Asn | Asp | Arg | Ile |
| | 290 | | | | | 295 | | | | | 300 | | | | |
| Phe | Val | Ser | Val | Thr | Asn | Glu | His | Leu | Ile | Asp | Met | Asp | His | Glu | Ala |
| 305 | | | | | 310 | | | | | 315 | | | | | 320 |
| Ser | Phe | Phe | Gly | Ala | Phe | Leu | Val | Gly | Gly | Ser | Gly | Ser | Gly | Ser | Arg |
| | | | | 325 | | | | | 330 | | | | | 335 | |
| Val | Ala | Ala | His | Ile | Thr | Gly | Thr | Arg | Gly | Arg | Ser | Asn | Thr | Leu | Ser |
| | | | 340 | | | | | 345 | | | | | 350 | | |
| Ser | Pro | Asn | Ser | Lys | Asn | Glu | Lys | Ala | Leu | Gly | Arg | Lys | Ile | Asn | Ser |
| | | | 355 | | | | | 360 | | | | | 365 | | |

Trp Glu Ser Ser Arg Ser Gly His Ser Phe Leu Ser Asn Leu His Leu
370                 375                 380

Arg Asn Gly Glu Leu Val Ile His Glu Lys Gly Phe Tyr Tyr Ile Tyr
385                 390                 395                 400

Ser Gln Thr Tyr Phe Arg Phe Gln Glu Glu Ile Lys Glu Asn Thr Lys
            405                 410                 415

Asn Asp Lys Gln Met Val Gln Tyr Ile Tyr Lys Tyr Thr Ser Tyr Pro
        420                 425                 430

Asp Pro Ile Leu Leu Met Lys Ser Ala Arg Asn Ser Cys Trp Ser Lys
            435                 440                 445

Asp Ala Glu Tyr Gly Leu Tyr Ser Ile Tyr Gln Gly Gly Ile Phe Glu
        450                 455                 460

Leu Lys Glu Asn Asp Arg Ile Phe Val Ser Val Thr Asn Glu His Leu
465                 470                 475                 480

Ile Asp Met Asp His Glu Ala Ser Phe Phe Gly Ala Phe Leu Val Gly
            485                 490                 495

Gly Pro Gly Ser Ser Ser Ser Ser Ser Gly Ser Cys Asp Lys Thr
        500                 505                 510

His Thr Cys Pro Pro Cys Pro Ala Pro Glu Leu Leu Gly Gly Pro Ser
            515                 520                 525

Val Phe Leu Phe Pro Pro Lys Pro Lys Asp Thr Leu Met Ile Ser Arg
530                 535                 540

Thr Pro Glu Val Thr Cys Val Val Val Asp Val Ser His Glu Asp Pro
545                 550                 555                 560

Glu Val Lys Phe Asn Trp Tyr Val Asp Gly Val Glu Val His Asn Ala
            565                 570                 575

Lys Thr Lys Pro Arg Glu Glu Gln Tyr Ser Thr Tyr Arg Val Val
        580                 585                 590

Ser Val Leu Thr Val Leu His Gln Asp Trp Leu Asn Gly Lys Glu Tyr
            595                 600                 605

Lys Cys Lys Val Ser Asn Lys Ala Leu Pro Ala Pro Ile Glu Lys Thr
610                 615                 620

Ile Ser Lys Ala Lys Gly Gln Pro Arg Glu Pro Gln Val Tyr Thr Leu
625                 630                 635                 640

Pro Pro Ser Arg Glu Glu Met Thr Lys Asn Gln Val Ser Leu Thr Cys
            645                 650                 655

Leu Val Lys Gly Phe Tyr Pro Ser Asp Ile Ala Val Glu Trp Glu Ser
        660                 665                 670

Asn Gly Gln Pro Glu Asn Asn Tyr Lys Thr Thr Pro Pro Val Leu Asp
        675                 680                 685

Ser Asp Gly Ser Phe Phe Leu Tyr Ser Lys Leu Thr Val Asp Lys Ser
        690                 695                 700

Arg Trp Gln Gln Gly Asn Val Phe Ser Cys Ser Val Met His Glu Ala
705                 710                 715                 720

Leu His Asn His Tyr Thr Gln Lys Ser Leu Ser Leu Ser Pro Gly Lys
            725                 730                 735

<210> SEQ ID NO 31
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 31

Asp Glu Val Asp
1
```